(12) United States Patent
Jitsuoka et al.

(10) Patent No.: US 7,960,402 B2
(45) Date of Patent: Jun. 14, 2011

(54) CARBAMOYL-SUBSTITUTED SPIRO DERIVATIVE

(75) Inventors: Makoto Jitsuoka, Moriya (JP); Norikazu Ohtake, Tsukuba (JP); Nagaaki Sato, Tsukuba (JP); Shigeru Tokita, Tsukuba (JP); Daisuke Tsukahara, Tsukuba (JP)

(73) Assignee: Banyu Pharmaceutical Co., Ltd., Kudankita, Chiyoda-ku, Tokyo (JP)

( * ) Notice: Subject to any disclaimer, the term of this patent is extended or adjusted under 35 U.S.C. 154(b) by 923 days.

(21) Appl. No.: 11/662,102

(22) PCT Filed: Sep. 6, 2005

(86) PCT No.: PCT/JP2005/016692
§ 371 (c)(1),
(2), (4) Date: Sep. 10, 2007

(87) PCT Pub. No.: WO2006/028239
PCT Pub. Date: Mar. 16, 2006

(65) Prior Publication Data
US 2008/0171753 A1    Jul. 17, 2008

(30) Foreign Application Priority Data

Sep. 7, 2004    (JP) .................................. 2004-259258
Nov. 29, 2004   (JP) .................................. 2004-344270

(51) Int. Cl.
| A61K 31/44 | (2006.01) |
| A61K 31/34 | (2006.01) |
| A61K 31/335 | (2006.01) |
| C07D 401/00 | (2006.01) |
| C07D 307/00 | (2006.01) |

(52) U.S. Cl. .......... 514/278; 514/462; 546/18; 549/466; 549/468

(58) Field of Classification Search .................. None
See application file for complete search history.

(56) References Cited

U.S. PATENT DOCUMENTS

| 6,191,160 B1 | 2/2001 | Gao et al. |
| 6,313,298 B1 | 11/2001 | Gao et al. |
| 6,326,375 B1 | 12/2001 | Fukami et al. |
| 6,335,345 B1 | 1/2002 | Fukami et al. |
| 6,388,077 B1 | 5/2002 | Fukami et al. |
| 6,462,053 B1 | 10/2002 | Fukami et al. |
| 6,495,559 B2 | 12/2002 | Gao et al. |
| 6,638,942 B1 | 10/2003 | Gao et al. |
| 6,649,624 B2 | 11/2003 | Fukami et al. |
| 6,723,847 B2 | 4/2004 | Fukami et al. |
| 6,803,372 B2 | 10/2004 | Fukami et al. |
| 7,365,079 B2 | 4/2008 | Otake et al. |
| 7,589,096 B2 | 9/2009 | Otake et al. |
| 2002/0052371 A1 | 5/2002 | Fukami et al. |
| 2002/0058813 A1 | 5/2002 | Gao et al. |
| 2002/0165391 A1 | 11/2002 | Fukami et al. |
| 2002/0188124 A1 | 12/2002 | Fukami et al. |
| 2003/0055251 A1 | 4/2003 | Fukami et al. |
| 2003/0220499 A1 | 11/2003 | Fukami et al. |
| 2004/0063942 A1 | 4/2004 | Gao et al. |
| 2005/0026901 A1 | 2/2005 | Janssens et al. |
| 2006/0111380 A1 | 5/2006 | Otake et al. |
| 2008/0188507 A1 | 8/2008 | Otake et al. |
| 2009/0258871 A1* | 10/2009 | Jitsuoka et al. ............. 514/232.8 |

FOREIGN PATENT DOCUMENTS

EP    1795527    9/2005

OTHER PUBLICATIONS

Witjmans et al. Expert Opinion on Investigational Drugs, 2007, 16(7), 967-985.*
Bergquist et al. Acta Physiologica Sinica, 2006, 58(4), 293-304.*
"Association of Clinical Research Professionals—Clinical Trial Updates", http://www.acrpnet.org/MainMenuCategory/Resources/TheWire/ClinicalTrialUpdates.aspx, accessed Jun. 18, 2010.*
Lintunen et al. The FASEB Journal, 2001, pp. 1-20.*
Zarrindast et al. Pharmacology and Toxicology, 2000, 87, pp. 169-173.*
"Type II diabetes", http://diabetes.webmd.com/type-2-diabetes, accessed Jun. 18, 2010.*
Leopold. Chemical Senses, 2002, 27, pp. 611-615.*
Hancoock et al. Expert Opinion on Investigational Drugs, 2004, 13(10), 1237-48.*
Zheng et al. Pharmacological Reviews, 2006, 58(2), 259-79.*
Supplementary European Search Report for EP 05 77 8590, Jan. 8, 2008.

* cited by examiner

*Primary Examiner* — Noble Jarrell
(74) *Attorney, Agent, or Firm* — J. Eric Thies; Gerard M. Devlin

(57) ABSTRACT

A compound represented by, e.g. the formula (I):

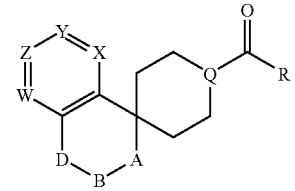

[wherein X, Y, Z, and W each independently represent optionally substituted methine; A, B, and D each independently represent —C(O)—, etc.; Q represents a methine or a nitrogen; and R represents the formula (II-1), optionally substituted with lower alkyl, etc.;

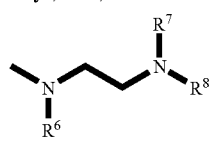

(wherein $R^6$ represents a lower alkyl, etc; and $R^7$ and $R^8$ each independently represents a lower alkyl, etc.)] or a pharmaceutically acceptable salt of the compound. The compounds and salt have antagonistic activity against a histamine H3 receptor or inverse agonistic activity against a histamine H3 receptor. They are useful in the prevention or treatment of metabolic diseases, circulatory diseases, or neurotic diseases.

10 Claims, No Drawings

CARBAMOYL-SUBSTITUTED SPIRO DERIVATIVE

TECHNICAL FIELD

The present invention relates to a carbamoyl-substituted spiro derivative.

CROSS REFERENCE TO RELATED APPLICATIONS

This application is a U.S. National Phase application under 35 U.S.C. §371 of PCT Application No. PCT/JP2005/016692, filed Sep. 6, 2005, which claims priority under 35 U.S.C. §119 from JP Application No. JP2004-344270, filed Nov. 29, 2004, and JP Application No. JP2004-259258, filed Sep. 7, 2004.

BACKGROUND ART

It has been known that, in living things such as mammals, histamine which is a biologically active endogenous factor functions as a neurotransmitter and has a pharmacological activity within a broad range (refer, for example, to *Life Science*, vol. 17, page 503 (1975)).

It has been made clear as a result of immunohistochemical studies that a histaminergic (producing) cell body is present on nodular papillary nucleus of posterior hypothalamus and also that a histaminergic nerve fiber is projected to a very broad range in brain and supports various pharmacological actions of histamine (refer, for example, to *Journal of Comparative Neurology*, volume 273, page 283).

The presence of histaminergic nerve in nodular papillary nucleus of posterior hypothalamus suggests that, in brain function, histamine plays an important role in the control of physiological functions particularly related to the functions of hypothalamus (such as sleeping, awaking rhythm, incretion, behavior of taking food and water and sex behavior) (refer, for example, to *Progress in Neurobiology*, volume 63, page 637 (2001)).

The fact that histaminergic nerve fiber is projected to the region related to maintenance of wakefulness (such as cerebral cortex) suggests the role played by histamine in adjusting the wakefulness or a cycle of awakening and sleeping. In addition, the fact that histaminergic nerve fiber is projected to many marginal structures such as hippocampus and amygdaloid complex suggests the role of histamine in the adjustment of autonomic nerve, in the control of emotion and motivated behavior and in the learning and memorizing process.

When histamine is released from producing cells, it plays its pharmacological actions as a result of action to specific polymer called a receptor on a cell membrane surface or in a target cell and conducts the adjustment of various physical functions. Until now, four kinds of histamine receptors have been found and, particularly as to a receptor participating in central and peripheral nerve functions of histamine, the presence of histamine H3 receptor has been shown by various pharmacological and physiological studies (refer, for example, to *Trends in Pharmacological Science*, volume 8, page 24 (1986)). Further, in recent years, human and rodential histamine H3 receptor gene has been identified and its presence has been clarified (refer, for example, to *Molecular Pharmacology*, volume 55, page 1101 (1999)).

Histamine H3 receptor is present in presynaptic membrane of central or peripheral nerve cells functioning as a self-receptor and controls not only release of histamine but also release of other neurotransmitters. Thus, histamine H3 receptor agonist, antagonist or inverse agonist regulates the liberation of histamine, noradrenaline, serotonin, acetylcholine, dopamine, etc. from nerve terminal. Release of the above-mentioned neurotransmitters is suppressed by a histamine H3 receptor agonist such as (R)-(α)-methylhistamine and is promoted by a histamine H3 receptor antagonist such as thioperamide or inverse agonist (refer, for example, to *Trends in Pharmacological Science*, volume 19, page 177 (1998)).

DISCLOSURE OF THE INVENTION

Under such circumstances, an object of the present invention is to provide a novel substance having an antagonistic action against a histamine H3 receptor (an action which inhibits the bonding of histamine to histamine H3 receptor) or an inverse agonistic action (an action which suppresses a homeostatic activity of histamine H3 receptor) or, in other words, to provide a novel substance acting as a histamine H3 receptor agonist or antagonist in living body.

The present inventors have found that specific carbamoyl-substituted spiro derivatives act as a histamine H3 receptor antagonist or inverse agonist and achieved the present invention.

Thus, the present invention provides the compounds or salts thereof mentioned in the following (1) to (17) in order to achieve the above-mentioned object.

(1) A compound represented by the formula (I) or a pharmaceutically acceptable salt thereof.

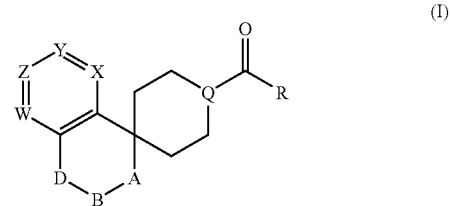

[wherein, X, Y, Z and W each independently represent a methine group optionally having substituent(s) selected from a substituent group α, A represents $-(C(R^3)(R^4))_{m1}-$, $-C(O)-$, $-O-$ or $N(R^5)-$, B represents $-N(SO_2R^1)-$, $-N(COR^2)-$, $-N(R^{50})-$, $-O-$ or $-C(O)-$, D represents $-(C(R^{30})(R^{40}))_{m2}-$, $-O-$, $-N(R^{51})$ or $-C(O)-$, Q represents a methine group or a nitrogen atom, $R^1$, $R^2$ and $R^5$ each independently represent a hydrogen atom, a lower alkyl group, an aralkyl group or an aryl group, $R^3$, $R^4$, $R^{30}$ and $R^{40}$ each independently represent a hydrogen atom, a hydroxyl group, a lower alkyl group, an aralkyl group or an aryl group, $R^{50}$ and $R^{51}$ each independently represent a hydrogen atom or a lower alkyl group, R represents a group of the following formula (II) which may have a substituent selected from the group consisting of a lower alkyl group (the lower alkyl group may be substituted with a halogen atom, an oxo group or an alkoxy group), a cycloalkyl group, a hydroxy group, an alkoxy group (the alkoxy group may be substituted with a halogen atom) and a halogen atom;

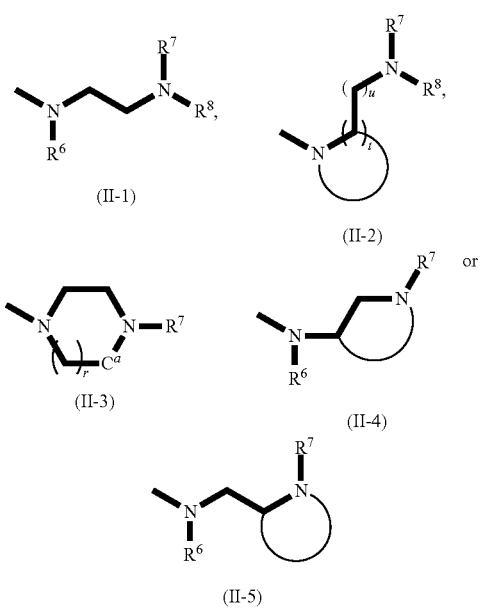

(wherein, $R^6$ represents a hydrogen atom or a lower alkyl group, $R^7$ and $R^8$ each independently represent a lower alkyl group, a cycloalkyl group, an aralkyl group, a heteroaryl alkyl group or $R^7$ and $R^8$ together with the nitrogen atom to which they bond form a four- to eight-membered nitrogen-containing aliphatic heterocyclic group; or when R is the above formula (II-3), $C^a$ and $R^7$ together with the nitrogen atom to which they bond form a four- to eight-membered nitrogen-containing aliphatic heterocyclic group; and the formula

wherein (II-2), (II-4) and (II-5) represent a four- to eight-membered nitrogen-containing aliphatic heterocyclic group), m1 and m2 each independently indicate 0 or 1, r indicates an integer of 0 to 2, t indicates 1 or 2 and u indicates 0 or 1 (with a proviso that t+u is 2)].

The substituent group α:

a halogen atom, a hydroxyl group, a lower alkyl group (the group may be substituted with a halogen atom, a hydroxyl group or an alkoxy group), a cycloalkyl group (the group may be substituted with a halogen atom, a hydroxyl group or an alkoxy group), an alkoxy group (the group may be substituted with a halogen atom or a hydroxyl group), an amino group, a cyano group, a mono- or di-lower alkylamino group, a formyl group, an alkanoyl group, a mono- or di-(lower alkyl)carbamoyl group, an arylcarbamoyl group, a heteroarylcarbamoyl group, an arylalkylcarbamoyl group, a heteroarylalkylcarbamoyl group, a lower alkylsulfonyl group, a lower alkylthio group, an aryloxycarbonylamino group, an arylalkyloxycarbonylamino group, an alkoxycarbonylamino group, an alkanoylamino group, an arylcarbonylamino group, an arylalkylcarbonyl group, a lower alylsulfonylamino group, an arylsulfonylamino group, a lower alkylsulfamoyl group, an arylsulfamoyl group, an aryl group, an aryloxy group, a heteroaryl group and an aralkyl group.

(2) The compound or a pharmaceutically acceptable salt thereof according to the above (1), wherein Q is a methine group.

(3) The compound or a pharmaceutically acceptable salt thereof according to the above (1), wherein Q is a nitrogen atom.

(4) The compound or a pharmaceutically acceptable salt thereof according to the above (1), wherein A is —$C(R^3)(R^4))_{m1}$—, B is —$N(SO_2R^1)$— or —$N(COR^2)$—, D is —$(CH_2)_{m2}$—, m1 is 0 and m2 is 0 or A is —O— or —$N(R^5)$—, B is —C(O)—, D is —$(C(R^3)(R^4))_{m2}$— and m2 is 0 or 1.

(5) The compound or a pharmaceutically acceptable salt thereof according to the above (1), wherein A is —C(O)—, B is —O— or —$N(R^{50})$—, D is —$(C(R^3)(R^4))_{m2}$— and m2 is 0 or 1.

(6) The compound or a pharmaceutically acceptable salt thereof according to the above (1), wherein A is —$(C(R^3)(R^4))_{m1}$, —O— or —$N(R^5)$—, B is —C(O)— and D is —$N(R^{51})$— or —O—.

(7) The compound or a pharmaceutically acceptable salt thereof according to the above (1), wherein A is —$(C(R^3)(R^4))_{m1}$, B is —$N(R^{50})$— or —O— and D is —C(O)—.

(8) The compound or a pharmaceutically acceptable salt thereof according to the above (1), wherein A is —$(C(R^3)(R^4))_{m1}$, B is —O—, D is —$(C(R^3)(R^4))_{m2}$—, m1 is 0 and m2 is 1.

(9) The compound or a pharmaceutically acceptable salt thereof according to the above (1), wherein A is —$(C(R^3)(R^4))_{m1}$—, B is —$N(COR^2)$— or —$N(SO_2R^1)$—, D is —$(C(R^{30})(R^{40}))_{m2}$, m1 is 1 and m2 is 0.

(10) The compound or a pharmaceutically acceptable salt thereof according to the above (1), wherein A is —O— or —$N(R^5)$—, B is —C(O)—, D is —$(C(R^{30})(R^{40}))_{m2}$— and m2 is 0.

(11) The compound or a pharmaceutically acceptable salt thereof according to the above (1), wherein A is —$N(R^5)$— or —O—, B is —C(O)— and D is —O— or —$N(R^{51})$—.

(12) The compound or a pharmaceutically acceptable salt thereof according to the above (1), wherein A is —$(C(R^3)(R^4))_{m1}$, B is —C(O)— and D is —O— or —$N(R^{51})$).

(13) The compound or a pharmaceutically acceptable salt thereof according to the above (1), wherein $R^6$ is a lower alkyl group.

(14) The compound or a pharmaceutically acceptable salt thereof according to any of the above (1) to (13), wherein R is (II-1), (II-2), (II-3) or (II-4) in the formula (II).

(15) The compound or a pharmaceutically acceptable salt thereof according to any of the above (1) to (14), wherein R is (II-1) in the formula (II).

(16) The compound or a pharmaceutically acceptable salt thereof according to the above (1), wherein the compound represented by the formula (I) is trans-5'-(2-fluoroethoxy)-3'-oxo-N-methyl-N-(2-piperidin-1-ylethyl)-spiro[cyclohexane-1,1'-(3'H)-isobenzofuran]-4-carboxamide hydrochloride, trans-3'-oxo-N-methyl-N-(2-piperidin-1-ylethyl)-spiro[cyclohexane-1,1'-(3'H)-isobenzofuran]-4-carboxamide hydrochloride, trans-3'-oxo-N-methyl-N-(2-pyrrolidin-1-ylethyl)-spiro[cyclohexane-1,1'-(3'H)-isobenzofuran]-4-carboxamide hydrochloride, trans-3'-oxo-N-(2-piperidin-1-ylethyl)-spiro[cyclohexane-1,1'-(3'H)-isobenzofuran]-4-carboxamide, trans-3'-oxo-N-(2-pyrrolidin-1-ylethyl)-spiro[cyclohexane-1,1'-(3'H)-isobenzofuran]-4-carboxamide, trans-4-ethylpiperazinyl-(2S)-methyl-3'-oxo-spiro[cyclohexane-1,1'-(3'H)-isobenzofuran]-4-carboxamide,
trans-4-(hexahydropyrrolo[1,2-a]pyrazinyl)-3'-oxo-spiro[cyclohexane-1,1'-(3'H)-isobenzofuran]-4-carboxamide,
trans-3'-oxo-N-methyl-N-(1-cyclopentylpyrrolidin-3-yl)-spiro[cyclohexane-1,1'-(3'H)-isobenzofuran]-4-carboxamide,
trans-5'-methoxy-3'-oxo-N-methyl-N-(2-piperidin-1-ylethyl)-spiro[cyclohexane-1,1'-(3'H)-isobenzofuran]-4-carboxamide hydrochloride,
trans-5'-fluoro-3'-oxo-N-methyl-N-(2-piperidin-1-ylethyl)-spiro[cyclohexane-1,1'-(3'H)-isobenzofuran]-4-carboxamide hydrochloride,
trans-5'-fluoro-2-pyrrolidin-1-ylmethylpyrrolidinyl-3'-oxo-spiro[cyclohexane-1,1'-(3'H)-isobenzofuran]-4-carboxamide hydrochloride,
trans-7'-methoxy-3'-oxo-N-methyl-N-(2-piperidin-1-ylethyl)-spiro[cyclohexane-1,1'-(3'H)-isobenzofuran]-4-carboxamide hydrochloride,
trans-7'-methoxy-3'-oxo-N-methyl-N-(2-pyrrolidin-1-ylethyl)-spiro[cyclohexane-1,1'-(3'H)-isobenzofuran]-4-carboxamide hydrochloride,
trans-6'-methoxy-3'-oxo-N-methyl-N-(2-pyrrolidin-1-ylethyl)-spiro[cyclohexane-1,1'-(3'H)-isobenzofuran]-4-carboxamide,
trans-N-methyl-1'-(methylsulfonyl)-N-(2-piperidin-1-ylethyl)-1',2'-dihydrospiro[cyclohexane-1,3'-indole]-4-carboxamide,
trans-N,2'-dimethyl-3'-oxo-N-(2-piperidin-1-ylethyl)-2',3'-dihydrospiro[cyclohexane-1,1'-isoindole]-4-carboxamide,
cis-N,2'-dimethyl-3'-oxo-N-(2-piperidin-1-ylethyl)-2',3'-dihydrospiro[cyclohexane-1,1'-isoindole]-4-carboxamide,
trans-5'-methoxy-3'-oxo-N-methyl-N-(2-pyrrolidin-1-ylethyl)-spiro[cyclohexane-1,1'-(3'H)-isobenzofuran]-4-carboxamide,
trans-5'-fluoro-3'-oxo-N-methyl-N-(2-pyrrolidin-1-ylethyl)-spiro[cyclohexane-1,1'-(3'H)-isobenzofuran]-4-carboxamide,
trans-5'-hydroxy-3'-oxo-N-methyl-N-(2-pyrrolidin-1-ylethyl)-spiro[cyclohexane-1,1'-(3'H)-isobenzofuran]-4-carboxamide,
1'-(4-piperidin-1-ylbutanoyl)-3H-spiro[2-benzofuran-1,4'-piperidine]-3-one,
trans-5'-methoxy-3'-oxo-N,4-dimethyl-N-(2-pyrrolidin-1-ylethyl)-spiro[cyclohexane-1,1'-(3'H)-isobenzofuran]-4-carboxamide,
trans-5'-hydroxy-3'-oxo-(N-methyl-N-(2-piperidin-1-ylethyl)-spiro[cyclohexane-1,1'-(3'H)-isobenzofuran]-4-carboxamide,
trans-3'-oxo-N-ethyl-N-(2-piperidin-1-ylethyl)-spiro[cyclohexane-1,1'-(3'H)-isobenzofuran]-4-carboxamide hydrochloride,
trans-4-cyclopentylpiperazinyl-3'-oxo-spiro[cyclohexane-1,1'-(3'H)-isobenzofuran]-4-carboxamide,
trans-4-cyclohexylpiperazinyl-3'-oxo-spiro[cyclohexane-1,1'-(3'H)-isobenzofuran]-4-carboxamide,
trans-4-butylpiperazinyl-3'-oxo-spiro[cyclohexane-1,1'-(3'H)-isobenzofuran]-4-carboxamide,
trans-4-(1-ethylpropyl)piperazinyl-3'-oxo-spiro[cyclohexane-1,1'-(3'H)-isobenzofuran]-4-carboxamide,
trans-4-(1-methylpropyl)piperazinyl-3'-oxo-spiro[cyclohexane-1,1'-(3'H)-isobenzofuran]-4-carboxamide,
trans-4-(1-isopropyl)piperazinyl-3'-oxo-spiro[cyclohexane-1,1'-(3'H)-isobenzofuran]-4-carboxamide,
trans-4-propylpiperazinyl-3'-oxo-spiro[cyclohexane-1,1'-(3'H)-isobenzofuran]-4-carboxamide,
trans-5'-fluoromethoxy-3'-oxo-[N-methyl-N-(2-piperidin-1-ylethyl)-spiro[cyclohexane-1,1'-(3'H)-isobenzofuran]-4-carboxamide hydrochloride,
N-methyl-3-oxo-N-(2-piperidin-1-ylethyl)-1'H,3H-spiro[2-benzofuran-1,4'-piperidine]-1'-carboxamide hydrochloride,
N-methyl-N-(2-piperidin-1-ylethyl)-1'H,3H-spiro[2-benzofuran-1,4'-piperidine]-1'-carboxamide hydrochloride,
4-fluoro-N-methyl-3-oxo-N-(2-piperidin-1-ylethyl)-1'H,3H-spiro[2-benzofuran-1,4'-piperidine]-1'-carboxamide,
N,2-dimethyl-3-oxo-N-(2-piperidin-1-ylethyl)-2,3-dihydro-1'H-spiro[isoindole-1,4'-piperidine]-1'-carboxamide,
1-(ethylsulfonyl)-N-methyl-N-(2-piperidin-1-ylethyl)-1,2-dihydro-1'H-spiro[indole-3,4'-piperidine]-1'-carboxamide,
N-methyl-3-(methylsulfonyl)-N-(2-piperidin-1-ylethyl)-2,3-dihydro-1'H-spiro[indene-1,4'-piperidine]-1'-carboxamide,
5-fluoro-N-methyl-N-(2-piperidin-1-ylethyl)-1'H,3H-spiro[2-benzofuran-1,4'-piperidine]-1'-carboxamide,
1-{2-[[(3,3-dimethyl-1'H-3H-spiro[2-benzofuran-1,4'-piperidine]-1'-yl)carbonyl](methyl)amino]ethyl}piperidine trifluoroacetate,
N-methyl-3-oxo-N-(2-piperidin-1-ylethyl)-2,3-dihydro-1'H-spiro[isoindole-1,4'-piperidine]-1'-carboxamide,
N-methyl-3-oxo-N-(2-piperidin-1-ylethyl)-2,3-dihydro-1'H-spiro[indene-1,4'-piperidine]-1'-carboxamide,
trans-5'-methoxy-3'-oxo-N-methyl-N-{2-[(3S)-3-methylpiperidin-1-yl]ethyl}-spiro[cyclohexane-1,1'-(3'H)-isobenzofuran]-4-carboxamide,
trans-5'-methoxy-3'-oxo-N-methyl-N-[2-(dimethylamino)ethyl]-spiro[cyclohexane-1,1'-(3'H)-isobenzofuran]-4-carboxamide,
trans-5'-methoxy-3'-oxo-N-methyl-N-[2-azetidin-1-ylethyl]-spiro[cyclohexane-1,1'-(3'H)-isobenzofuran]-4-carboxamide,
trans-5'-methoxy-3'-oxo-N-methyl-N-{2-[(2R)-2-methylpyrrolidin-1-yl]ethyl}spiro[cyclohexane-1,1'-(3'H)-isobenzofuran]-4-carboxamide,
trans-5'-methoxy-3'-oxo-N-methyl-N-[2-(2-methylpiperidin-1-yl)ethyl]-spiro[cyclohexane-1,1'-(3'H)-isobenzofuran]-4-carboxamide,
trans-5'-methoxy-3'-oxo-N-methyl-N-(2-azepan-1-ylethyl)-spiro[cyclohexane-1,1'-(3'H)-isobenzofuran]-4-carboxamide,
trans-5'-methoxy-3'-oxo-N-methyl-N-(2-azocan-1-ylethyl)-spiro[cyclohexane-1,1'-(3'H)-isobenzofuran]-4-carboxamide,
2-piperidin-1-ylethyl-3-oxo-1'H,3H-spiro[2-benzo-furan-1,4'-piperidine]-1'-carboxylate,
trans-5'-{[(trifluoromethyl)sulfonyl]oxy}-3'-oxo-N-methyl-N-(2-piperidin-1-ylethyl)-spiro[cyclohexane-1,1'-(3'H)-isobenzofuran]-4-carboxamide,
trans-5'-{[(trifluoromethyl)sulfonyl]oxy}-3'-oxo-N-methyl-N-(2-pyrrolidin-1-ylethyl)-spiro[cyclohexane-1,1'-(3'H)-isobenzofuran]-4-carboxamide,
trans-5'-(pyridin-3-yl)-3'-oxo-N-methyl-N-(2-piperidin-1-ylethyl)-spiro[cyclohexane-1,1'-(3'H)-isobenzofuran]-4-carboxamide,
trans-5'-(pyridin-4-yl)-3'-oxo-N-methyl-N-(2-piperidin-1-ylethyl)-spiro[cyclohexane-1,1'-(3'H)-isobenzofuran]-4-carboxamide, trans-5'-(pyridin-5-yl)-3'-oxo-N-methyl-N-(2-piperidin-1-ylethyl)-spiro[cyclohexane-1,1'-(3'H)-isobenzofuran]-4-carboxamide, trans-5'-(2-methoxypyrimidin-5-yl)-3'-oxo-N-methyl-N-(2-pyrrolidin-1-ylethyl)-spiro[cyclohexane-1,1'-(3'H)-isobenzofuran]-4-carboxamide, trans-5'-(pyrazin-2-yl)-3'-oxo-N-methyl-N-(2-piperidin-1-ylethyl)-spiro[cyclohexane-1,1'-(3'H)-isobenzofuran]-4-carboxamide, trans-5'-(pyridin-2-yl)-3'-oxo-N-methyl-N-(2-piperidin-1-ylethyl)-spiro[cyclohexane-1,1'-(3'H)-isobenzofuran]-4-carboxamide, trans-5'-(pyrazin-2-yl)-3'-oxo-N-methyl-N-(2-pyrrolidin-1-ylethyl)-spiro[cyclohexane-1,1'-(3'H)-isobenzofuran]-4-carboxamide, trans-5'-pyridin-2-yl-3'-oxo-N-methyl-N-(2-pyrrolidin-1-ylethyl)-spiro[cyclohexane-1,1'-(3'H)-isobenzofuran]-4-carboxamide, trans-5'-cyclopropyl-3'-oxo-N-methyl-N-(2-pyrrolidin-1-ylethyl)-spiro[cyclohexane-1,1'-(3'H)-isobenzofuran]-4-carboxamide, trans-5'-vinyl-3'-oxo-N-methyl-N-(2-pyrrolidin-1-ylethyl)-spiro[cyclohexane-1,1'-(3'H)-isobenzofuran]-4-carboxamide, trans-5'-ethyl-3'-oxo-N-methyl-N-(2-pyrrolidin-1-ylethyl)-spiro[cyclohexane-1,1'-(3'H)-isobenzofuran]-4-carboxamide, trans-5'-ethoxy-3'-oxo-N-methyl-N-(2-pyrrolidin-1-ylethyl)-spiro[cyclohexane-1,1'-(3'H)-isobenzofuran]-4-carboxamide, trans-5'-isopropoxy-3'-oxo-N-methyl-N-(2-pyrrolidin-1-ylethyl)-spiro[cyclohexane-1,1'-(3'H)-isobenzofuran]-4-carboxamide, trans-5'-[2-fluoro-1-(fluoromethyl)ethoxy]-3'-oxo-N-methyl-N-(2-piperidin-1-ylethyl)-spiro[cyclohexane-1,1'-(3'H)-isobenzofuran]-4-carboxamide, trans-5'-[2-fluoro-1-(fluoromethyl)ethoxy]-3'-oxo-N-methyl-N-(2-pyrrolidin-1-ylethyl)-spiro[cyclohexane-1,1'-(3'H)-isobenzofuran]-4-carboxamide, trans-5'-(pyridin-2-yloxy)-3'-oxo-N-methyl-N-(2-piperidin-1-ylethyl)-spiro[cyclohexane-1,1'-(3'H)-isobenzofuran]-4-carboxamide, trans-5'-(pyrimidin-2-yloxy)-3'-oxo-N-methyl-N-(2-piperidin-1-ylethyl)-spiro[cyclohexane-1,1'-(3'H)-isobenzofuran]-4-carboxamide, trans-5'-(pyrazin-2-yloxy)-3'-oxo-N-methyl-N-(2-piperidin-1-ylethyl)-spiro[cyclohexane-1,1'-(3'H)-isobenzofuran]-4-carboxamide, trans-5'-(pyrimidin-2-yloxy)-3'-oxo-N-methyl-N-(2-pyrrolidin-1-ylethyl)-spiro[cyclohexane-1,1'-(3'H)-isobenzofuran]-4-carboxamide, trans-5'-[(4-methoxypyrimidin-2-yl)oxy]-3'-oxo-N-methyl-N-(2-pyrrolidin-1-ylethyl)-spiro[cyclohexane-1,1'-(3'H)-isobenzofuran]-4-carboxamide, trans-5'-(pyrazin-2-yloxy)-3'-oxo-N-methyl-N-(2-pyrrolidin-1-ylethyl)-spiro[cyclohexane-1,1'-(3'H)-isobenzofuran]-4-carboxamide, trans-5'-[(2-cyanopyrimidin-5-yl)oxy]-3'-oxo-N-methyl-N-(2-pyrrolidin-1-ylethyl)-spiro[cyclohexane-1,1'-(3'H)-isobenzofuran]-4-carboxamide, trans-5'-[(5-fluoropyrimidin-2-yl)oxy]-3'-oxo-N-methyl-N-(2-pyrrolidin-1-ylethyl)-spiro[cyclohexane-1,1'-(3'H)-isobenzofuran]-4-carboxamide, trans-5'-(piperidin-4-yloxy)-3'-oxo-N-methyl-N-(2-piperidin-1-ylethyl)-spiro[cyclohexane-1,1'-(3'H)-isobenzofuran]-4-carboxamide, trans-5'-[(1-acetylpiperidin-4-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-acetylpyrrolidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-acetylpiperidin-4-yl)oxy]-3'-oxo-N-methyl-N-(2-pyrrolidin-1-ylethyl)-spiro[cyclohexane-1,1'-(3'H)-isobenzofuran]-4-carboxamide, trans-5'-[(1-acetylpyrrolidin-3-yl)oxy]-3'-oxo-N-methyl-N-(2-pyrrolidin-1-ylethyl)-spiro[cyclohexane-1,1'-(3'H)-isobenzofuran]-4-carboxamide, trans-5'-4-([1-(diphenylmethyl)azetidin-3-yl]oxy]-3'-oxo-N-methyl-N-(2-piperidin-1-ylethyl)-spiro[cyclohexane-1,1'-(3'H)-isobenzofuran]-4-carboxamide, trans-5'-(azetidin-3-yloxy)-3'-oxo-N-methyl-N-(2-piperidin-1-ylethyl)-spiro[cyclohexane-1,1'-(3'H)-isobenzofuran]-4-carboxamide, trans-5'-[(1-acetylazetidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-methylsulfonyl)piperidin-4-yl]oxy]-3'-oxo-N-methyl-N-(2-piperidin-1-ylethyl)-spiro[cyclohexane-1,1'-(3'H)-isobenzofuran]-4-carboxamide, trans-5'-[(1-methylsulfonyl)-pyrrolidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-methylsulfonyl)-pyrrolidin-3-yl)oxy]-3'-oxo-N-methyl-N-(2-pyrrolidin-1-ylethyl)-spiro[cyclo-hexane-1,1'-(3'H)-isobenzofuran]-4-carboxamide, trans-5'-[(1-methylsulfonyl)-azetidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-formylazetidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-methoxycarbonylazetidin-3-yl)oxy]-3'-oxo-N-methyl-N-(2-piperidin-1-ylethyl)-spiro[cyclohexane-1,1'-(3'H)-isobenzofuran]-4-carboxamide or trans-5'-[(1-propionylazetidin-3-yl)oxy]-3'-oxo-N-methyl-N-(2-piperidin-1-ylethyl)-spiro[cyclohexane-1,1'-(3'H)-isobenzofuran]-4-carboxamide.

The compound or salt mentioned in the above (1) to (16) acts in a living body as a histamine H3 receptor antagonist or inverse agonist. Thus, the present invention also provides a histamine H3 receptor antagonist or inverse agonist comprising the compound or a pharmaceutically acceptable salt thereof mentioned in any of the above (1) to (17).

According to the studies in recent years, it has been shown that a histamine H3 receptor has a very high homeostatic activity (activity observed in the absence of an endogenous ergogenic factor (such as histamine)) in receptor-expressing cells/tissues or membrane fractions derived therefrom or in living body (refer, for example, to *Nature*, volume 408, page 860) and the homeostatic activity as such has been reported to be suppressed by an inverse agonist. For example, thioperamide or ciproxifan suppresses the homeostatic self-receptor activity of the histamine H3 receptor and, as a result, it promotes the release of neurotransmitters (such as histamine) from nerve terminal.

In rats, a highly selective inhibitor for a histamine-synthesizing enzyme (histidine decarboxylase) inhibits their awakening and, therefore, histamine participates in adjustment of behavioral awakening. In cats, administration of (R)-(α)-methylhistamine which is a histamine H3 receptor agonist increases the sleeping with deep slow wave (refer, for example, to *Brain Research*, volume 523, page 325 (1990)).

On the contrary, thioperamide which is a histamine H3 receptor antagonist or inverse agonist increases the awakening state in a dose-dependent manner and thioperamide decreases slow wave and REM sleep (refer, for example, to *Life Science*, volume 48, pages 2397 (1991)). Thioperamide or GT-2331 which is a histamine H3 receptor antagonist or inverse agonist also decreases affective cataplexy and sleep of narcolepsy dogs (refer, for example, to *Brain Research*, volume 793, page 279 (1998)).

Those findings suggest that H3 receptors may participate in control of vigilance sleep and in sleep disorder-associated disease, further suggesting a possibility that selective histamine H3 agonists, antagonists or inverse agonists may be useful for prevention or treatment of sleep disorder and various diseases accompanied by sleep disorder (such as idiopathic hypersomnia, repetitive hypersomnia, true hypersomnia, narcolepsy, sleep periodic limb movement disorder, sleep apnea syndrome, circadian rhythm disorder, chronic fatigue syndrome, REM sleep disorder, senile insomnia, sleep unwholesomeness of night-work laborers, idiopathic insomnia, repetitive insomnia, true insomnia, depression, anxiety and schizophrenia). Accordingly, the compounds mentioned in the above (1) to (16) and salts thereof acting as histamine H3 receptor antagonists or inverse agonists are believed to be effective for prevention or treatment of sleep disorder and various diseases accompanied thereby.

Further, in rats, thioperamide or GT-2331 which are a histamine H3 receptor antagonist or inverse agonist improves the symptoms of learning disability (LD) and attention-deficient/hyperactivity disorder (ADHD) (refer, for example, to *Life Science*, volume 69, page 469 (2001)). Furthermore, in rats, (R)-(α)-methylhistamine which is a histamine H3 receptor agonist lowers a recognizing ability to objective and learning effect in a recognizing test for objective and a passive withdrawal test.

On the other hand, in a test for amnesia induced by scopolamine, thioperamide which is a histamine H3 receptor antagonist or inverse agonist reduces the amnesia on a dose-dependent manner (refer, for example, to *Pharmacology, Biochemistry and Behavior*, volume 68, page 735 (2001)).

Those findings suggest that histamine H3 receptor antagonists or inverse agonists are useful for prevention or treatment of memory and learning disability and various diseases accompanied by that (such as Alzheimer's disease, Parkinson's disease and attention deficit/hyperactivity disorder). Accordingly, the compounds or salts thereof mentioned in the above (1) to (16) are also believed to be effective for prevention or treatment of memory and learning disability and various diseases accompanied by that.

In addition, in rats, eating behavior is suppressed by administration of histamine into a ventricle and, therefore, histamine is suggested to participate in control of eating behavior (refer, for example, to *Journal of Physiology and Pharmacology*, volume 49, page 191 (1998)). Actually, thioperamide which is a histamine H3 receptor antagonist or inverse agonist suppresses the eating behavior on a dose-depending manner while it promotes the liberation of histamine in brain (refer, for example, to *Behavioral Brain Research*, volume 104, page 147 (1999)).

Those findings suggest that histamine H3 receptors participate in control of eating behavior and histamine H3 antagonists or inverse agonists are useful for prevention or treatment of metabolic diseases such as eating disorder, obesity, diabetes, emaciation and hyperlipemia. Accordingly, the compounds or salts thereof mentioned in the above (1) to (16) are also believed to be effective for prevention or treatment of metabolic diseases as such.

Further, in rats, (R)-(α)-methylhistamine which is a histamine H3 receptor agonist lowers a basal diastolic blood pressure on a dose-depending manner. Such an action is antagonized by thioperamide which is a histamine H3 receptor antagonist or inverse agonist (refer, for example, to *European Journal of Pharmacology*, volume 234, page 129 (1993)).

Those findings suggest that histamine H3 receptors participate in control of blood pressure, heart beat and cardiovascular output and that histamine H3 receptor agonists, antagonists or inverse agonists are useful for prevention and treatment of circulatory diseases such as hypertension and various cardiac diseases. Accordingly, the compounds or salts thereof mentioned in the above (1) to (16) are also believed to be effective for prevention or treatment of the circulatory diseases as such.

Further, in mice, thioperamide which is a histamine H3 receptor antagonist or inverse agonist has been shown to suppress spasm which is induced by electric stimulation or epilepsy-like attack induced by pentylenetetrazole (PTZ) on a dose-depending manner (refer, for example, to *European Journal of Pharmacology*, volume 234, page 129 (1993) and *Pharmacology, Biochemistry and Behavior*, volume 68, page 735 (2001)).

Those findings suggest that histamine H3 receptor antagonists or inverse agonists are useful for prevention and treatment of epilepsy or central convulsion. Accordingly, the compounds or salts thereof mentioned in the above (1) to (16) are also believed to be effective for prevention or treatment of epilepsy and central convulsion as such.

Thus, the present invention also provides a preventive or treating agent for metabolic diseases, circulatory diseases or neural diseases which contains a compound mentioned in any of the above (1) to (16) or a pharmaceutically acceptable salt thereof as an effective ingredient.

With regard to the above metabolic disease, at least one which is selected from the group consisting of obesity, diabetes, dysendocrinism, hyperlipemia, gout and fatty liver may be exemplified.

With regard to the above circulatory disease, at least one which is selected from the group consisting of stenocardia, acute congestive cardiac insufficiency, myocardial infarction, coronary sclerosis, hypertension, renal disease and electrolyte imbalance may be exemplified.

With regard to the above neural disease, at least one which is selected from the group consisting of sleep disorder, disease accompanied by sleep disorder, hyperphagia, emotional disturbance, epilepsy, delirium, dementia, attention deficit/hyperactivity disorder, memory disorder, Alzheimer's disease, Parkinson's disease, recognition disorder, motion disorder, paresthesia, dysosmia, resistance to morphine, narcotic dependence, alcoholic dependence and tremor may be exemplified.

With regard to the above neural disease, at least one which is selected from the group consisting of idiopathic hypersomnia, repetitive hypersomnia, true hypersomnia, narcolepsy, sleep periodic limb movement disorder, sleep apnea syndrome, circadian rhythm disorder, chronic fatigue syndrome, REM sleep disorder, senile insomnia, sleep unwholesomeness of night-work laborers, idiopathic insomnia, repetitive insomnia, true insomnia, depression, anxiety and schizophrenia may be also exemplified.

The compounds and the salts thereof mentioned in the above (1) to (16) may also be used together with a co-drug. Thus, the present invention further provides a preventive or treating agent for metabolic diseases, circulatory diseases or neural diseases containing the compound mentioned in the above (1) to (16) or a pharmaceutically acceptable salt thereof and a co-drug as effective ingredients. Examples of the co-drug are a treating agent for diabetes, a treating agent for hyperlipemia, a treating agent for hypertension and an anti-obesity agent. Two or more of each of the co-drugs as such may be used jointly.

With regard to the preventive or treating agent as such, a preventive or treating agent for metabolic diseases, circulatory diseases or neural diseases containing the following (i), (ii) and (iii) may be further provided.

(i) a compound mentioned in any of the aforementioned (1) to (16) or a pharmaceutically acceptable salt thereof;

(ii) at least one member which is selected from the group consisting of the following (a) to (g):

(a) a histamine H3 receptor antagonist or inverse agonist other than (i), (b) a biguanide, (c) a PPAR (peroxisome proliferators-activated receptor) agonist, (d) insulin, (e) somatostatin, (f) α-glucosidase inhibitor and (g) an insulin secretion promoter;

(iii) a pharmaceutically-acceptable carrier.

In addition, compounds which are trans-5-(2-fluoroethoxy)-3-oxo-3H-spiro[2-benzofuran-1,1'-cyclohexane]-4'-carboxylic acid, trans-5-methoxy-3-oxo-3H-spiro[2-benzofuran-1,1'-cyclohexane]-4'-carboxylic acid, trans-6-methoxy-3-oxo-3H-spiro[2-benzofuran-1,1'-cyclohexane]-4'-carboxylic acid, trans-7-methoxy-3-oxo-3H-spiro[2-benzofuran-1,1'-cyclohexane]-4'-carboxylic acid or trans-5-fluoro-3-oxo-3H-spiro[2-benzofuran-1,1'-cyclohexane]-4'-carboxylic acid, trans-5-hydroxy-3-oxo-3H-spiro[2-benzofuran-1,1'-cyclohexane]-4'-carboxylic acid, trans-2'-methyl-3'-oxo-2',3'-dihydrospiro[cyclohexane-1,1'-isoindole]-4'-carboxylic acid and cis-2'-methyl-3'-oxo-2',3'-dihydrospiro[cyclohexane-1,1'-isoindole]-4'-carboxylic acid and trans-5-methoxy-3-oxo-3H-spiro[2-benzofuran-1,1'-cyclohexane]-4'-methyl-4-carboxylic acid and pharmaceutically-acceptable salts thereof are compounds which are used for producing the compound represented by the formula (I) according to the present invention.

BEST MODE FOR CARRYING OUT THE INVENTION

Now the meanings of the terms used in this specification will be described and then the compounds concerning the present invention will be described.

Examples of "aryl group" are a hydrocarbon-ring aryl group having 6 to 14 carbons such as phenyl group, naphthyl group, biphenyl group and anthryl group.

"Heteroaryl group" means a five- or six-membered monocyclic group having 1 to 4 hetero atom(s) selected from the group consisting of oxygen atom, sulfur atom and nitrogen atom in the heteroaryl group or means a bicyclic heteroaryl group in which the above monocyclic heteroaryl group is fused with a benzene ring or a pyridine ring and its examples are furyl group, thienyl group, pyrrolyl group, imidazolyl group, triazolyl group, thiazolyl group, thiadiazolyl group, isothiazolyl group, oxazolyl group, isoxazolyl group, pyridyl group, pyrimidinyl group, pyridazinyl group, pyrazolyl group, pyrazinyl group, quinolyl group, isoquinolyl group, quinazolinyl group, quinolidinyl group, quinoxalinyl group, cinnolinyl group, benzimidazolyl group, imidazopyridyl group, benzofuranyl group, naphthylidinyl group, 1,2-benzoisoxazolyl group, benzoxazolyl group, benzothiazolyl group, oxazolopyridyl group, pyridothiazolyl group, isothiazolopyridyl group and benzothienyl group.

"Lower alkyl group" means a linear or branched alkyl group having 1 to 6 carbon(s) and its examples are methyl group, ethyl group, propyl group, isopropyl group, butyl group, isobutyl group, sec-butyl group, tert-butyl group, pentyl group, isoamyl group, neopentyl group, isopentyl group, 1,1-dimethylpropyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,2,2-trimethylpropyl group and 1-ethyl-2-methylpropyl group.

"Alkoxy group" is a group in which hydrogen atom of hydroxyl group is substituted with the aforementioned lower alkyl group and its examples are methoxy group, ethoxy group and propoxy group.

"Cycloalkyl group" is preferably a cycloalkyl group having 3 to 9 carbons and its examples are cyclopropyl group, cyclobutyl group, cyclopentyl group, cyclohexyl group, cycloheptyl group, cyclooctyl group and cyclononyl group.

"Aralkyl group" means the aforementioned lower alkyl group having the aforementioned aryl group and its examples are benzyl group, 1-phenylethyl group, 2-phenylethyl group, 1-naphthylmethyl group and 2-naphthylmethyl group.

"Heteroarylalkyl group" means a group in which the aforementioned heteroaryl group and the aforementioned alkyl group are bonded and its examples are furan-3-ylmethyl group, furan-2-ylmethyl group, furan-3-ylethyl group, furan-2-ylethyl group, furan-3-ylpropyl group, furan-2-ylpropyl group, thiophen-3-ylmethyl group, thiophen-2-ylmethyl group, thiophen-3-ylethyl group, thiophen-2-ylethyl group, thiophen-3-ylpropyl group, thiophen-2-ylpropyl group, 1H-pyrrol-3-ylmethyl group, 1H-pyrrol-2-ylmethyl group, 1H-pyrrol-3-ylethyl group, 1H-pyrrol-2-ylethyl group, 1H-pyrrol-3-ylpropyl group, 1H-pyrrol-2-ylpropyl group, 1H-imidazol-4-ylmethyl group, 1H-imidazol-2-ylmethyl group, 1H-imidazol-5-ylmethyl group, 1H-imidazol-4-ylethyl group, 1H-imidazol-2-ylethyl group, 1H-imidazol-5-ylethyl group, 1H-imidazol-4-ylpropyl group, 1H-imidazol-2-ylpropyl group, 1H-imidazol-5-ylpropyl group, 1H-[1,2,3]triazol-4-ylmethyl group, 1H-[1,2,3]triazol-5-ylmethyl group, 1H-[1,2,3]triazol-4-ylethyl group, 1H-[1,2,3]triazol-5-ylethyl group, 1H-[1,2,3]triazol-4-ylpropyl group, 1H-[1,2,3]triazol-5-ylpropyl group, 1H-[1,2,4]triazol-3-ylmethyl group, 1H-[1,2,4]triazol-5-ylmethyl group, 1H-[1,2,4]triazol-3-ylethyl group, 1H-[1,2,4]triazol-5-ylethyl group, 1H-[1,2,4]triazol-3-ylpropyl group, 1H-[1,2,4]triazol-5-ylpropyl group, thiazol-4-ylmethyl group, thiazol-3-ylmethyl group, thiazol-2-ylmethyl group, thiazol-4-ylethyl group, thiazol-3-ylethyl group, thiazol-2-ylethyl group, thiazol-4-ylpropyl group, thiazol-3-ylpropyl group, thiazol-2-ylpropyl group, [1,2,4]thiadiazol-3-ylmethyl group, [1,2,4]-thiadiazol-3-ylethyl group, [1,2,4]thiadiazol-3-ylpropyl group, [1,2,4]thiadiazol-5-ylmethyl group, [1,2,4]thiadiazol-5-ylethyl group, [1,2,4]thiadiazol-5-ylpropyl group, [1,3,4]thiadiazol-2-ylmethyl group, [1,3,4]thiadiazol-2-ylethyl group and [1,3,4]thiadiazol-2-ylpropyl group.

"Halogen atom" means, for example, fluorine atom, chlorine atom, bromine atom, iodine atom, etc.

Now, in order to more specifically disclose the compound of the present invention represented by the formula (I), the formula (I)

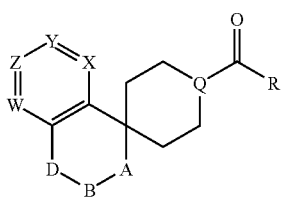 (I)

[wherein, the symbols have the same meanings as above] will be illustrated in more detail as follows.

X, Y, Z and W each independently represent a methine group which may have substituent(s) selected from the group consisting of a substituent group α.

"Methine group which may have substituent(s) selected from the group consisting of a substituent group α" is an unsubstituted methine group or a methine group having a substituent at the position where substitution is possible and the substituent can select one or more being same or different or, preferably, one from the group consisting of a substituent group α.

The substituent group a comprises a halogen atom, a hydroxyl group, a lower alkyl group (the group may be substituted with a halogen atom, a hydroxyl group or an alkoxy group), a cycloalkyl group (the group may be substituted with a halogen atom, a hydroxyl group or an alkoxy group), an alkoxy group (the group may be substituted with a halogen atom or a hydroxyl group), a cycloalkoxy group (one of carbon atoms constituting the cycloalkoxy group may be substituted with a nitrogen atom, and the nitrogen atom may be substituted with an alkanoyl group), an amino group, a cyano group, a mono- or di-lower alkylamino group, a formyl group, an alkanoyl group, a mono- or di-lower alkylcarbamoyl group, an arylcarbamoyl group, a heteroarylcarbamoyl group, an arylalkylcarbamoyl group, a heteroarylalkylcarbamoyl group, a lower alkylsulfonyl group, a lower alkylthio group, an aryloxycarbonylamino group, an arylalkyloxycarbonylamino group, an alkoxycarbonylamino group, an alkanoylamino group, an arylcarbonylamino group, an arylalkylcarbonyl group, a lower alkylsulfonylamino group, an arylsulfonylamino group, a lower alkylsulfamoyl group, an arylsulfamoyl group, an aryl group, an aryloxy group, a heteroaryl group and an aralkyl group.

With regard to the substituent group α, more preferred one is a halogen atom, a hydroxyl group, a lower alkyl group (the group may be substituted with a halogen atom, a hydroxyl group or an alkoxy group), a cycloalkyl group (the group may be substituted with a halogen atom, a hydroxyl group or an alkoxy group), an alkoxy group, a cycloalkoxy group (one of carbon atoms constituting the cycloalkoxy group may be substituted with a nitrogen atom and the nitrogen atom may be substituted with an alkanoyl group), cyano group, an alkanoyl group, a lower alkylsulfonyl group, a lower alkylthio group, an aryl group, an aryloxy group or a heteroaryl group and more preferred one is a halogen atom, a hydroxyl group, a lower alkyl group (the group may be substituted with a halogen atom, a hydroxyl group or an alkoxy group) or an alkoxy group.

With regard to the halogen atom which is the substituent, examples thereof are fluorine atom, chlorine atom, bromine atom and iodine atom.

With regard to the lower alkyl group which is the substituent, examples thereof are methyl group, ethyl group, n-propyl group and isopropyl group.

The lower alkyl group may be substituted with a halogen atom, a hydroxyl group or an alkoxy group.

Examples of the lower alkyl group substituted with halogen atom are fluoromethyl group, chloromethyl group, 2-fluoroethyl group and 2-chloroethyl group.

Examples of the lower alkyl group substituted with hydroxyl group are hydroxymethyl group and 2-hydroxyethyl group.

Examples of the cycloalkyl group of the substituent are cyclopropyl group, cyclobutyl group, cyclopentyl group and cyclohexyl group.

The cycloalkyl group may be substituted with halogen atom, hydroxyl group or an alkoxy group.

Examples of the alkoxy group of the substituent are methoxy group, ethoxy group and isopropoxy group.

The alkoxy group may be substituted with halogen atom or hydroxyl group.

The cycloalkyloxy group of the substituent means a group where the aforementioned cycloalkyl group and oxygen atom are bonded and, to be more specific, its examples are cyclopropyloxy group, cyclobutyloxy group, cyclopentyloxy group and cyclohexyloxy group.

One of carbon atoms constituting the cycloalkyloxy group may be substituted with a nitrogen atom.

The cycloalkyloxy group in which one carbon atom is substituted with a nitrogen atom is preferably a 4- to 7-membered aliphatic ring, concretely including, for example, an azetidin-3-yloxy group, a pyrrolidin-3-yloxy group, a piperidin-4-yloxy group, a homopiperidin-4-yl group et al.

The nitrogen atom in the three- to seven-membered nitrogen-containing aliphatic ring as such may be substituted with an alkanoyl group, a lower alkylsulfonyl group, diphenylmethyl group, formyl group or a lower alkoxycarbonyl group.

Examples of the lower alkanoyl group are acetyl group and propionyl group.

The lower alkylsulfonyl group means a group where the afore-defined lower alkyl group and sulfonyl group are bonded and, to be more specific, its examples are methylsulfonyl group, ethylsulfonyl group, isopropylsulfonyl group, propylsulfonyl group and butylsulfonyl group.

The lower alkoxycarbonyl group means a group where the lower alkoxy group and carbonyl group are bonded and, to be more specific, its examples are methoxycarbonyl group, ethoxycarbonyl group and isopropyloxycarbonyl group.

The mono-(lower alkyl)amino group of the substituent means amino group which is mono-substituted with the aforementioned lower alkyl group and its examples are methylamino group, ethylamino group, propylamino group, isopropylamino group, butylamino group, sec-butylamino group and tert-butylamino group.

The di-(lower alkyl)amino group of the substituent means an amino group is di-substituted with the same or different afore-mentioned lower alkyl groups and its examples are dimethylamino group, diethylamino group, dipropylamino group, methylpropylamino group and diisopropylamine group.

The alkanoyl group of the substituent means a group where the aforementioned alkyl group and carbonyl group are bonded and its examples are methylcarbonyl group, ethylcarbonyl group, propylcarbonyl group and isopropylcarbonyl group.

The mono-(lower alkyl)carbamoyl group of the substituent means a group where carbamoyl group which is mono-substituted with the aforementioned lower alkyl group and its examples are methylcarbamoyl group, ethylcarbamoyl group, propylcarbamoyl group, isopropylcarbamoyl group, butylcarbamoyl group, sec-butylcarbamoyl group and tert-butylcarbamoyl group.

The di-(lower alkyl)carbamoyl group of the substituent means a carbamoyl group which is di-substituted with the same or different aforementioned lower alkyl groups and examples of the "di-lower alkylcarbamoyl group" are dimethylcarbamoyl group, diethylcarbamoyl group, ethylmethylcarbamoyl group, dipropylcarbamoyl group, methylpropylcarbamoyl group and diisopropylcarbamoyl group.

The arylcarbamoyl group of the substituent means a group where one or two aforementioned "aryl group(s)" and carbamoyl group are bonded and its examples are phenylcarbamoyl group, naphthalen-1-ylcarbamoyl group and naphthalen-2-ylcarbamoyl group.

The heteroarylcarbamoyl group of the substituent means a group where one or two "the aforementioned heteroaryl group(s)" and carbamoyl group are bonded and its examples are furan-2-ylcarbamoyl group, furan-3-ylcarbamoyl group, thiopen-2-ylcarbamoyl group, thiophen-3-ylcarbamoyl group, 1H-pyrrol-2-ylcarbamoyl group, 1H-pyrrol-3-ylcarbamoyl group, 1H-imidazol-2-ylcarbamoyl group, 1H-imidazol-4-ylcarbamoyl group, 3H-imidazol-4-ylcarbamoyl group, 4H-[1,3,4]triazol-3-ylcarbamoyl group, 2H-[1,2,4]triazol-3-ylcarbamoyl group, 1H-[1,2,4]triazol-3-ylcarbamoyl group, thiazol-2-ylcarbamoyl group, thiazol-4-ylcarbamoyl group, thiazol-5-ylcarbamoyl group, pyridin-2-ylcarbamoyl group, pyridin-3-ylcarbamoyl group, pyridin-4-ylcarbamoyl group, pyrimidin-2-ylcarbamoyl group, pyrimidin-4-ylcarbamoyl group, pyrimidin-5-ylcarbamoyl group, pyridazin-3-ylcarbamoyl group, pyridazin-4-ylcarbamoyl group, 2H-pyrazol-3-ylcarbamoyl group, 1H-pyrazol-4-ylcarbamoyl group, 1H-pyrazol-3-ylcarbamoyl group, pyrazin-3-ylcarbamoyl group, pyrazin-4-ylcarbamoyl group, quinolin-2-ylcarbamoyl group, quinolin-3-ylcarbamoyl group, quinolin-4-ylcarbamoyl group, isoquinolin-1-ylcarbamoyl group, isoquinolin-3-ylcarbamoyl group, isoquinolin-4-ylcarbamoyl group, quinazolin-2-ylcarbamoyl group, quinazolin-3-ylcarbamoyl group, quinoxalin-2-ylcarbamoyl group, quinoxalin-3-ylcarbamoyl group, cinnolin-3-ylcarbamoyl group, cinnolin-4-ylcarbamoyl group, 1H-benzimidazol-2-ylcarbamoyl group, 1H-imidazo[4,5-b]pyridin-5-ylcarbamoyl group, 1H-imidazo[4,5-b]pyridin-6-ylcarbamoyl group, 1H-imidazo[4,5-b]pyridin-7-ylcarbamoyl group, benzo[d]isoxazol-4-ylcarbamoyl group, benzo[d]isoxazol-5-ylcarbamoyl group, benzo[d]isoxazol-6-ylcarbamoyl group, benzoxazol-4-ylcarbamoyl group, benzoxazol-5-ylcarbamoyl group and benzoxazol-6-ylcarbamoyl group.

The arylalkylcarbamoyl group of the substituent means a group where one or two of the aforementioned "aralkyl group(s)" and carbamoyl group are bonded and its examples are benzylcarbamoyl group, 1-phenylethylcarbamoyl group, 2-phenylethylcarbamoyl group, 1-naphthylmethylcarbamoyl group and 2-naphthylmethylcarbamoyl group.

The heretoarylalkylcarbamoyl group of the substituent means a group where one or two of the aforementioned "heteroarylalkyl group(s)" and carbamoyl group are bonded and its examples are furan-3-ylmethylcarbamoyl group, furan-2-ylmethylcarbamoyl group, furan-3-ylethylcarbamoyl group, furan-2-ylethylcarbamoyl group, furan-3-ylpropylcarbamoyl group, furan-2-ylpropylcarbamoyl group, thiophen-3-ylmethylcarbamoyl group, thiophen-2-ylmethylcarbamoyl group, thiophen-3-ylethylcarbamoyl group, thiophen-2-ylethylcarbamoyl group, thiophen-3-ylpropylcarbamoyl group, thiophen-2-ylpropylcarbamoyl group, 1H-pyrrol-3-ylmethylcarbamoyl group, 1H-pyrrol-2-ylmethylcarbamoyl group, 1H-pyrrol-3-ylethylcarbamoyl group, 1H-pyrrol-2-ylethylcarbamoyl group, 1H-pyrrol-3-ylpropylcarbamoyl group, 1H-pyrrol-2-ylpropylcarbamoyl group, 1H-imidazol-4-ylmethylcarbamoyl group, 1H-imidazol-2-ylmethylcarbamoyl group, 1H-imidazol-5-ylmethylcarbamoyl group, 1H-imidazol-4-ylethylcarbamoyl group, 1H-imidazol-2-ylethylcarbamoyl group, 1H-imidazol-5-ylethylcarbamoyl group, 1H-imidazol-4-ylpropylcarbamoyl group, 1H-imidazol-2-ylpropylcarbamoyl group, 1H-imidazol-5-ylpropylcarbamoyl group, 1H-[1,2,3]triazol-4-ylmethylcarbamoyl group, 1H-[1,2,3]triazol-5-ylmethylcarbamoyl group, 1H-[1,2,3]triazol-4-ylethylcarbamoyl group, 1H-[1,2,3]triazol-5-ylethylcarbamoyl group, 1H-[1,2,3]triazol-4-ylpropylcarbamoyl group, 1H-[1,2,3]triazol-5-ylpropylcarbamoyl group, 1H-[1,2,4]triazol-3-ylmethylcarbamoyl group, 1H-[1,2,4]triazol-5-ylmethylcarbamoyl group, 1H-[1,2,4]triazol-3-ylethylcarbamoyl group, 1H-[1,2,4]triazol-5-ylethylcarbamoyl group, 1H-[1,2,4]triazol-3-ylpropylcarbamoyl group, 1H-[1,2,4]triazol-5-ylpropylcarbamoyl group, thiazol-4-ylmethylcarbamoyl group, thiazol-3-ylmethylcarbamoyl group, thiazol-2-ylmethylcarbamoyl group, thiazol-4-ylethylcarbamoyl group, thiazol-3-ylethylcarbamoyl group, thiazol-2-ylethylcarbamoyl group, thiazol-4-ylpropylcarbamoyl group, thiazol-3-ylpropylcarbamoyl group, thiazol-2-ylpropylcarbamoyl group, [1,2,4]thiadiazol-3-ylmethylcarbamoyl group, [1,2,4]thiadiazol-3-ylethylcarbamoyl group, [1,2,4]thiadiazol-3-ylpropylcarbamoyl group, [1,2,4]thiadiazol-5-ylmethylcarbamoyl group, [1,2,4]thiadiazol-5-ylethylcarbamoyl group, [1,2,4]thiadiazol-5-ylpropylcarbamoyl group, [1,3,4]thiadiazol-2-ylmethylcarbamoyl group, [1,3,4]thiadiazol-2-ylethylcarbamoyl group and [1,3,4]thiadiazol-2-ylpropylcarbamoyl group.

The lower alkylsulfonyl group of the substituent means a group where the aforementioned lower alkyl group and sulfonyl group are bonded and its examples are methylsulfonyl group, ethylsulfonyl group, propylsulfonyl group, isopropylsulfonyl group and butylsulfonyl group.

The lower alkylthio group of the substituent means a group where the aforementioned lower alkyl group and sulfur atom are bonded and its examples are methylthio group, ethylthio group, propylthio group and isopropylthio group.

The aryloxy group of the substituent means a group where the aforementioned aryl group and oxygen atom are bonded and its examples are phenoxy group, naphthalen-1-yloxy group and naphthalen-2-yloxy group.

The aryloxycarbonylamino group of the substituent means a group where the aforementioned aryloxy group and carbonylamino group are bonded and its examples are phenoxycarbonylamino group, etc.

Examples of the arylalkyloxycarbonylamino group of the substituent are benzyloxycarbonylamino group, 1-phenylethyloxycarbonylamino group, 2-phenylethyloxycarbonylamino group, 1-naphthylmethyloxycarbonylamino group and 2-naphthylmethyloxycarbonylamino group.

The alkoxycarbonylamino group of the substituent means a group where the aforementioned alkoxy group and carbonylamino group are bonded and its examples are methoxycarbonylamino group, ethoxycarbonylamino group and propoxycarbonylamino group.

The alkanoylamino group of the substituent means a group where the aforementioned alkanoyl group and amino group are bonded and its examples are methylcarbonylamino group, ethylcarbonylamino group, propylcarbonylamino group, isopropylcarbonylamino group and isobutylcarbonylamino group.

The arylcarbonylamino group of the substituent means a group where the aforementioned aryl group and carbonylamino group are bonded and its examples are phenylcarbonylamino group, naphthalen-1-ylcarbonylamino group and naphthalen-2-ylcarbonylamino group.

The arylalkylcarbonyl group of the substituent means a group where the aforementioned aralkyl group and carbonyl group are bonded and its examples are benzylcarbonyl group, naphthalen-1-ylcarbonyl group and naphthalen-2-ylcarbonyl group.

The lower alkylsulfonylamino group of the substituent means a group where the aforementioned lower alkyl group and sulfonylamino group are bonded and its examples are methylsulfonylamino group, ethylsulfonylamino group, isopropylsulfonylamino group and n-butylsulfonylamino group.

The arylsulfonylamino group of the substituent means a group where the aforementioned aryl group and sulfonylamino group are bonded and its examples are phenylsulfonylamino group, naphthalen-1-ylsulfonylamino group and naphthalen-2-ylsulfonylamino group.

The lower alkylsulfamoyl group of the substituent means a group where one or two of the aforementioned "alkylamino group(s)" and sulfonyl group are bonded and its examples are methylsulfamoyl group, ethylsulfamoyl group, propylsulfamoyl group, isopropylsulfamoyl group, dimethylsulfamoyl group, diethylsulfamoyl group, ethylmethylsulfamoyl group and isopropylmethylsulfamoyl group.

The arylsulfamoyl group of the substituent means a group where the aforementioned aryl group and aminosulfonyl group are bonded and its examples are phenylsulfamoyl group, naphthalen-1-ylsulfamoyl group and naphthalen-2-ylsulfamoyl group.

With regard to the aryl group of the substituent, the same group as the aforementioned aryl group may be listed.

With regard to the heteroaryl group of the substituent, the same group as the aforementioned heteroaryl group may be listed.

With regard to the aralkyl group of the substituent, the same group as the aforementioned aralkyl group may be listed.

A represents —(C(R$^3$)(R$^4$))$_{m1}$—, —C(O)—, —O— or N(R$^5$)—.

R$^3$ and R$^4$ each independently represent a hydrogen atom, a hydroxyl group, a lower alkyl group, an aralkyl group or an aryl group.

R$^5$ represent a hydrogen atom, a lower alkyl group, an aralkyl group or an aryl group.

With regard to —C(R$^3$)(R$^4$)— represented by A, its specific examples are a single bond, a methylene group, —CH(CH$_3$)— and —C(CH$_3$)$_2$, etc. and, among them, a single bond, a methylene group, etc. are preferred.

With regard to —N(R$^5$)— represented by A, its examples are —NH—, a methylamino group, an ethylamino group and an isopropylamino group, etc. and, among them, —NH—, a methylamino group, an ethylamino group, etc. are preferred.

B represents —N(SO$_2$R$^1$)—, —N(COR$^2$)—, —N(R$^{50}$)—, —O— or —C(O)—.

R$^1$ and R$^2$ each independently represent a hydrogen atom, a lower alkyl group, an aralkyl group or an aryl group.

R$^{50}$ represents a hydrogen atom or a lower alkyl group.

Examples of —N(SO$_2$R$^1$)— represented by B are a methanesulfonylamino group, an ethanesulfonylamino group, an isopropylsulfonylamino group, a benzylsulfonylamino group and a phenylsulfonylamino group, etc. and, among them, a methanesulfonylamino group, an ethanesulfonylamino group, etc. are preferred.

Examples of —N(COR$^2$)— represented by B are a methylcarbonylamino group, an ethylcarbonylamino group, an isopropylcarbonylamino group, a phenylcarbonylamino group and a benzylcarbonylamino group, etc. and, among them, a methylcarbonylamino group, an ethylcarbonylamino group, etc. are preferred.

Examples of —N(R$^{50}$)— represented by B are —NH—, a methylamino group, an ethylamino group, an isopropylamino group, a benzylsulfonylamino group and a phenylsulfonylamino group, etc. and, among them, —NH—, a methylamino group and an ethylamino group are preferred.

D represents —(C(R$^{30}$)(R$^{40}$))$_{m2}$—, —O—, —N(R$^{51}$)— or —C(O)—.

R$^{30}$ and R$^{40}$ each independently represent a hydrogen atom, a hydroxyl group, a lower alkyl group, an aralkyl group or an aryl group.

R$^{51}$ represents a hydrogen atom or a lower alkyl group.

Examples of —(C(R$^{30}$)(R$^{40}$))$_{m2}$— represented by D are a single bond, a methylene group, —CH(CH$_3$)— and —C(CH$_3$)$_2$—, etc.

Examples of —N(R$^{51}$)— represented by D are —NH—, a methylamino group, an ethylamino group and an isopropylamino group and, among them, —NH—, a methylamino group and an ethylamino group are preferred.

Q represents a methine group or a nitrogen atom.

With regard to a group represented by the formula (III)

(III)

[wherein, the symbols have the same meanings as above], its specific examples are a group represented by the formula (III-1), (III-1)

(III-1-1) (III-1-2)

(III-1-3) (III-1-4)

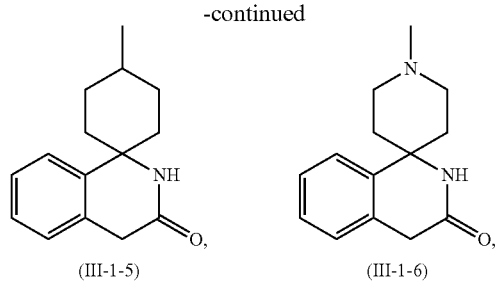
(III-1-5) (III-1-6)
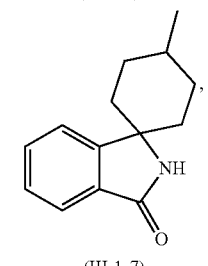 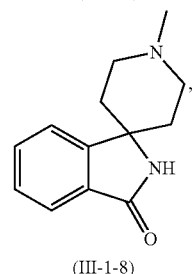
(III-1-7) (III-1-8)
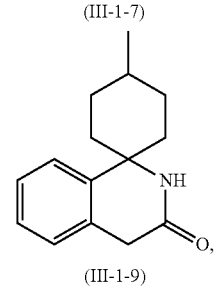 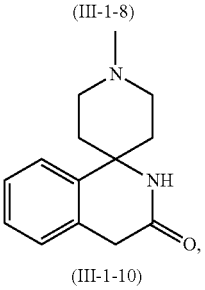
(III-1-9) (III-1-10)
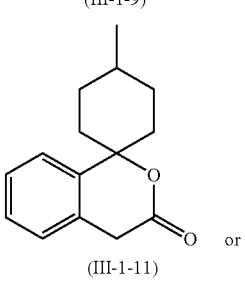 or
(III-1-11) (III-1-12)
a group represented by the formula (III-2),
(III-2)
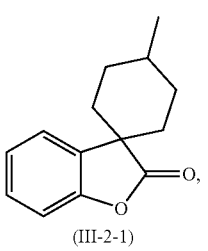 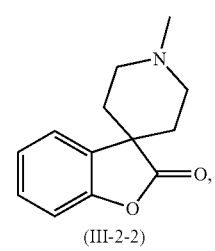
(III-2-1) (III-2-2)
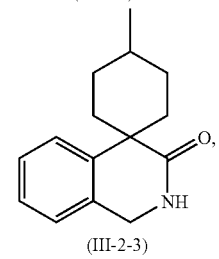 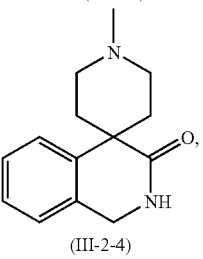
(III-2-3) (III-2-4)
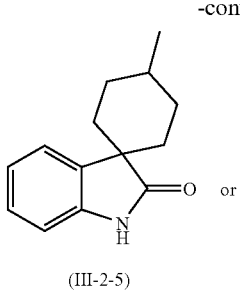 or
(III-2-5) (III-2-6)
a group represented by the formula (III-3),
(III-3)
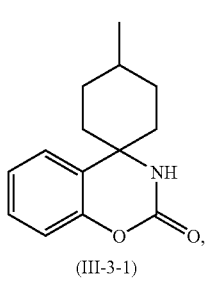 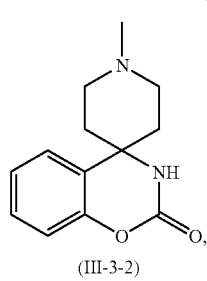
(III-3-1) (III-3-2)
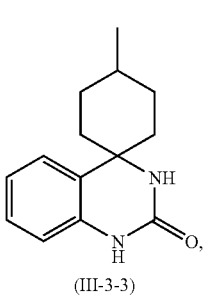 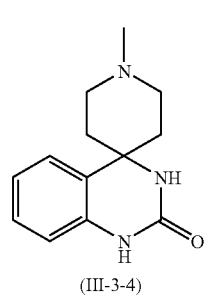
(III-3-3) (III-3-4)
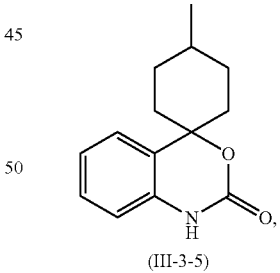 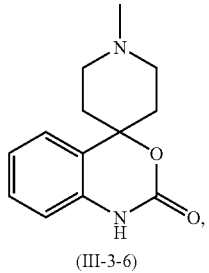
(III-3-5) (III-3-6)
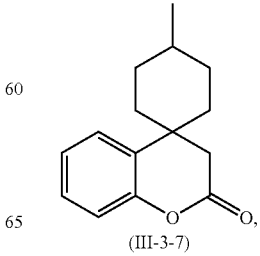 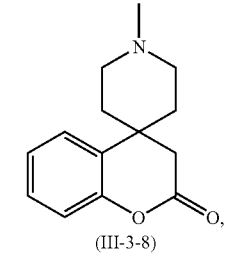
(III-3-7) (III-3-8)

-continued

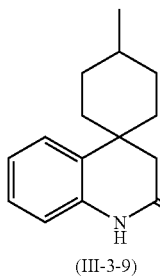
(III-3-9)

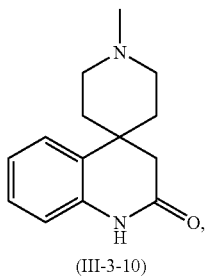
(III-3-10)

a group represented by the formula (III-4),

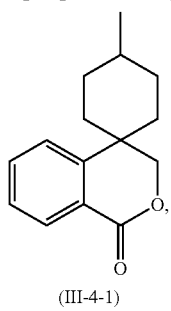
(III-4-1)

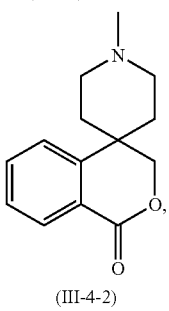
(III-4-2)

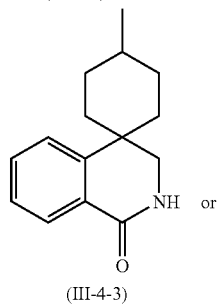
(III-4-3)

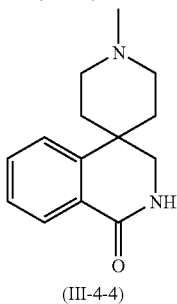
(III-4-4)

or a group represented by the formula (III-5).

(III-5)

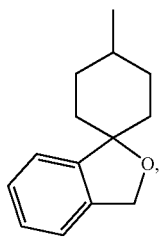
(III-5-1)

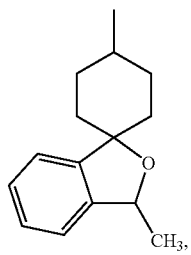
(III-5-2)

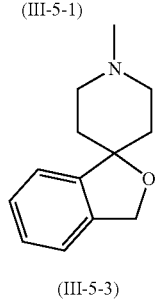
(III-5-3)

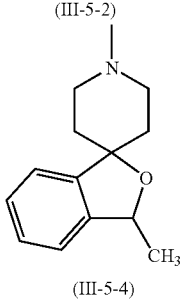
(III-5-4)

Among the groups represented by the above formulae (III-1) to (III-5), the group represented by the formula (III-1), (III-2) or (III-5) is preferred and the group represented by the formula (III-1) is more preferred.

Among the group represented by the above formula (III-1), the group represented by the formula (III-1-1), (III-1-2), (III-1-3), (III-1-4), (III-1-5), (III-1-6), (III-1-7) or (III-1-8), (III-1-9) is preferred and the group represented by (III-1-3), (III-1-4), (III-1-5), (III-1-6) or (III-1-7) is more preferred.

R represents a group of the following formula (II)

(II)

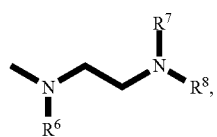
(II-1)

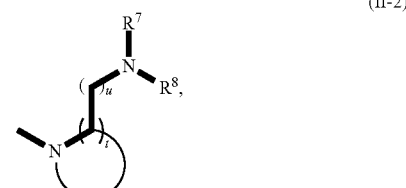
(II-2)

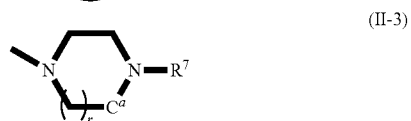
(II-3)

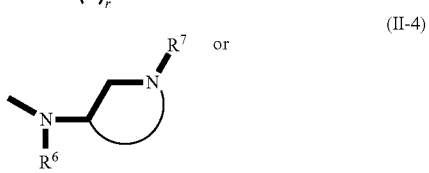
(II-4)

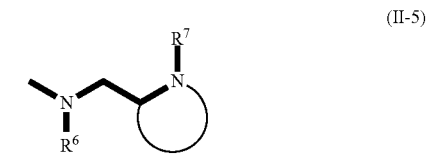
(II-5)

[wherein, the symbols have the same meanings as above].

$R^6$ represents a hydrogen atom or a lower alkyl group.

$R^7$ and $R^8$ each independently represent a lower alkyl group, a cycloalkyl group, an aralkyl group, a heteroarylalkyl group or $R^7$ and $R^8$ together with nitrogen atom to which they bond form a four- to eight-membered nitrogen-containing aliphatic heterocyclic group.

With regard to the "four- to eight-membered nitrogen-containing aliphatic heterocyclic group formed by $R^7$, $R^8$ and nitrogen atom to which they bond" or the "four- to eight-membered nitrogen-containing aliphatic heterocyclic group" shown by a group represented by the formula

[wherein t has the same meaning as above] in the formulae (II-2), (II-4) and (II-5), its specific examples are an azetidinyl group, a pyrrolidinyl group, a piperidinyl group, a homopiperidinyl group and a morpholino group.

With regard to the group represented by the formula (II-1), its specific example is the group represented by the following formula (II-1-1)
(II-1-1)
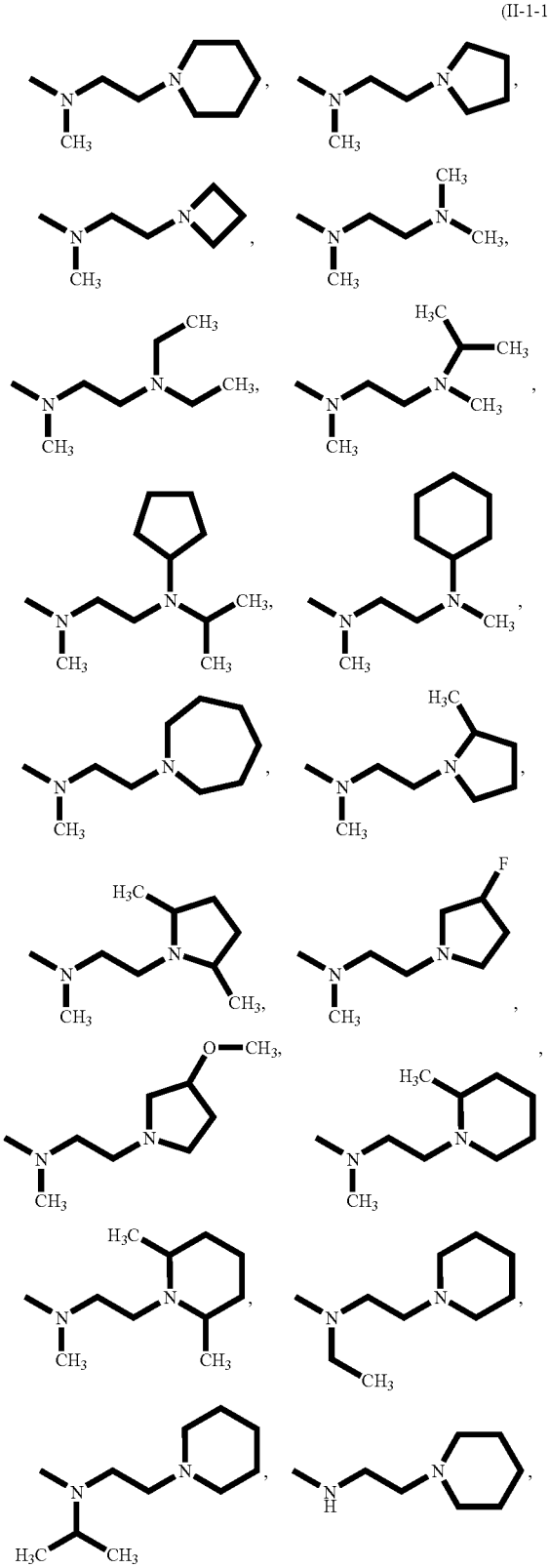
-continued
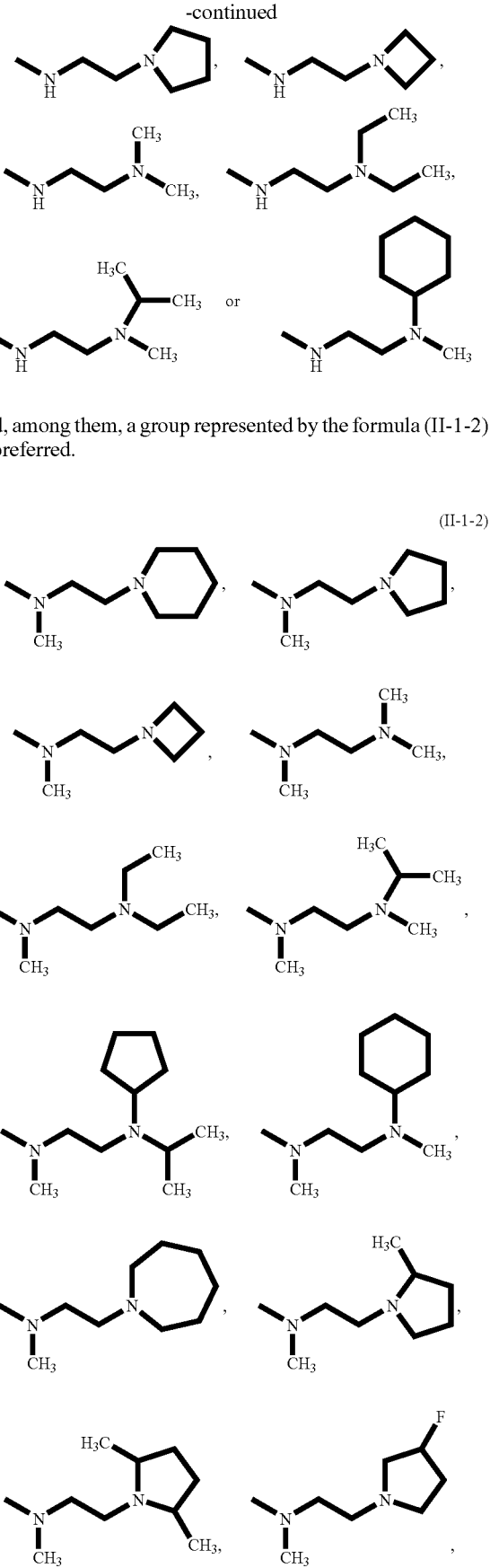
and, among them, a group represented by the formula (II-1-2) is preferred.
(II-1-2)

With regard to the group represented by the formula (II-2), its specific example is the group represented by the formula (II-2-1).

With regard to the group represented by the formula (II-3), its specific example is the group represented by the formula (II-3-1).

With regard to the group represented by the formula (II-4), its specific example is the group represented by the formula (II-4-1)

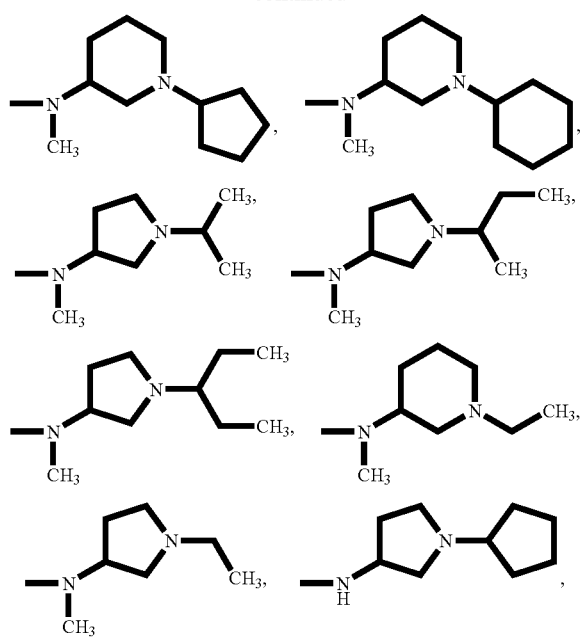

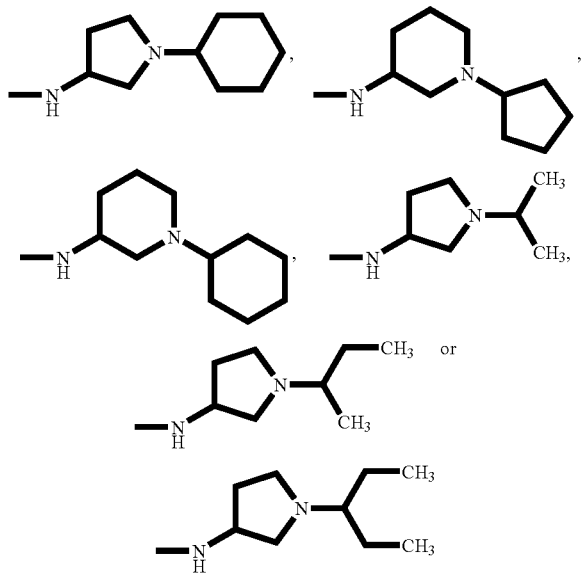

and, among them, the group represented by the formula (II-4-2) is preferred.

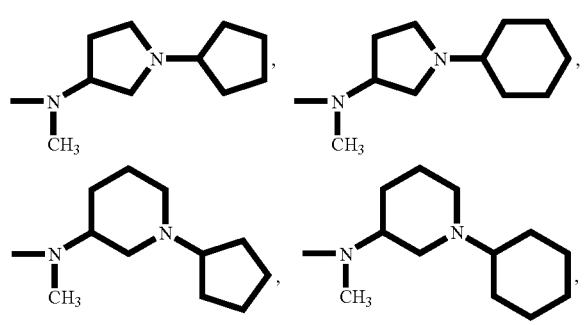

With regard to the group represented by the formula (II-5), its specific example is the group represented by the formula (II-5-1).

(II-5-1)

Among the group represented by the aforementioned formula (II), the group represented by (II-1), (II-2), (II-3) or (II-4) is preferred and the group represented by (II-1) is more preferred.

Incidentally, compounds which are trans-5-(2-fluoroethoxy)-3-oxo-3H-spiro[2-benzofuran-1,1'-cyclohexane]-4'-carboxylic acid, trans-5-methoxy-3-oxo-3H-spiro[2-benzofuran-1,1'-cyclohexane]-4'-carboxylic acid, trans-6-methoxy-3-oxo-3H-spiro[2-benzofuran-1,1'-cyclohexane]-

4'-carboxylic acid, trans-7-methoxy-3-oxo-3H-spiro[2-benzofuran-1,1'-cyclohexane]-4'-carboxylic acid or trans-5-fluoro-3-oxo-3H-spiro[2-benzofuran-1,1'-cyclohexane]-4'-carboxylic acid, trans-5-hydroxy-3-oxo-3H-spiro[2-benzofuran-1,1'-cyclohexane]-4'-carboxylic acid, trans-2'-methyl-3'-oxo-2',3'-dihydrospiro[cyclohexane-1,1'-isoindole]-4'-carboxylic acid and cis-2'-methyl-3'-oxo-2',3'-dihydrospiro[cyclohexane-1,1'-isoindole]-4'-carboxylic acid and trans-5-methoxy-3-oxo-3H-spiro[2-benzofuran-1,1'-cyclohexane]-4'-methyl-4-carboxylic acid and pharmaceutically-acceptable salts thereof are the intermediate which are useful for the production of the compound represented by the formula (I).

Now the process for producing the compound of the present invention will be described.

The compound represented by the formula (I-1)

[wherein, the symbols have the same meanings as above] covered by the formula (I) can be produced by, for example, the following process.

[wherein, Hal represents a halogen atom, $L_1$ represents a methanesulfonyl group, a trifluoromethanesulfonyl group or a p-toluenesulfonyl group, etc. and other symbols have the same meanings as above.]

(Step 1)

This step is a process for producing a compound (2) by the reaction of the compound (1) with 1,4-cyclohexanedione monoethyleneketal in the presence of a base.

Examples of the compound (1) used in the present reaction are 2-bromo-6-methoxybenzoic acid, 2-bromo-5-methoxybenzoic acid, 2-bromo-4-methoxybenzoic acid, 2-bromo-3-methoxybenzoic acid, 2-bromo-6-fluoroethyloxybenzoic acid, 2-bromo-5-fluoroethyloxybenzoic acid, 2-bromo-4-fluoroethyloxybenzoic acid, 2-bromo-3-fluoroethyloxybenzoic acid, 2-bromo-6-fluorobenzoic acid, 2-bromo-5-fluorobenzoic acid, 2-bromo-4-fluorobenzoic acid, 2-bromo-3-fluorobenzoic acid, 2-bromo-6-methylbenzoic acid, 2-bromo-5-methylbenzoic acid, 2-bromo-4-methylbenzoic acid, 2-bromo-3-methylbenzoic acid, 2,5-dibromobenzoic acid, 3-bromo-4-pyridinecarboxylic acid, 3-bromo-2-pyridinecarboxylic acid and 2-fluoro-3-chloro-4-pyridinecarboxylic acid, etc.

Amount of the 1,4-cyclohexanedione monoethyleneketal used in this step to one equivalent of the compound (1) is usually 1 to 5 equivalent(s) and, preferably, 1 to 2 equivalent(s).

Examples of a base used are butyl lithium and lithium 2,2,6,6-tetramethylpiperidide.

Amount of the base used to one equivalent of the compound (1) is usually 2 to 10 equivalents and, preferably, 2 to 4 equivalents.

With regard to a reaction solvent, there is no particular limitation so far as it does not affect the reaction and examples thereof are tetrahydrofuran (THF), diethyl ether and tert-butyl methyl ether, etc. in which THF is preferred.

Reaction temperature is usually from $-100°$ C. to $100°$ C. and, preferably, from $-78°$ C. to $50°$ C.

Reaction time is usually from 1 hour to 48 hours and, preferably, from 1 hour to 24 hours.

The compound (2) prepared as such can be subjected to the next step with or without isolation and purification by a known separation and purification means such as concentration, concentration in vacuo, crystallization, extraction with solvent, reprecipitation and chromatography.

(Step 2)

This step is a process where a ketal group of the compound (2) produced in the above step 1 is removed to produce a compound (3). Removal of the ketal group can be carried out by a method mentioned in a document (such as "Protective Groups in Organic Synthesis" by T. W. Green, second edition, John Wiley & Sons, 1991), by a method similar thereto or by combining those methods with a conventional method.

To be more specific, hydrochloric acid, sulfuric acid, p-toluenesulfonic acid, trifluoroacetic acid, etc. may be used in the removal of the acetal group.

Amount of hydrochloric acid, sulfuric acid, p-toluenesulfonic acid, trifluoroacetic acid, etc. used to 1 equivalent of the compound (1) is usually from 0.1 to 100 equivalent(s) or, preferably, from 0.5 to 50 equivalent(s).

With regard to the reaction solvent in this step, there is no particular limitation so far as it does not affect the reaction and its examples are water and water-containing methanol, ethanol, acetone, THF, 1,4-dioxane and acetic acid where methanol, ethanol, acetone, THF and 1,4-dioxane are preferred.

Reaction temperature is usually from $0°$ C. to $200°$ C. and, preferably, from $20°$ C. to $150°$ C.

Reaction time is usually from 1 hour to 48 hours and, preferably, from 1 hour to 10 hours.

The compound (3) prepared as such can be subjected to the next step with or without isolation and purification by a known separation and purification means such as concentration, concentration in vacuo, crystallization, extraction with solvent, reprecipitation and chromatography.

(Step 3)

This step is a process for producing a compound (4) by subjecting the carbonyl group of the compound (3) produced in the above-mentioned step (2) to a reducing reaction.

Examples of the reducing agent used in this step are sodium borohydride, lithium borohydride, lithium aluminum hydride and diisobutyl aluminum hydride, etc.

Amount of the reducing agent used in this step to 1 equivalent of the compound (3) is usually from 1 to 20 equivalent(s) and, preferably, form 1 to 3 equivalent(s).

There is no particular limitation for the reaction solvent so far as it does not affect the reaction and its examples are THF, a mixed solvent of THF with water, 1,4-dioxane, a mixed solvent of dioxane with water, methanol, ethanol, diethyl ether and dichloromethane, etc. where THF and a mixed solvent of THF with water are preferred.

Reaction temperature is usually from $-100°$ C. to $100°$ C. and, preferably, from $-100°$ C. to $50°$ C.

Reaction time is usually from 5 minutes to 24 hours and, preferably, from 5 minutes to 4 hours.

The compound (4) prepared as such can be subjected to the next step with or without isolation and purification by a known separation and purification means such as concentration, concentration in vacuo, crystallization, extraction with solvent, reprecipitation and chromatography.

(Step 4)

This step is a process for producing the compound (5) by the reaction of the compound (4) produced in the above-mentioned step 3 with a compound $L_1$-Cl in the presence of a base.

Specific examples of the base used in this step are triethylamine, sodium carbonate, potassium carbonate, diisopropylethylamine and pyridine, etc. where triethylamine and diisopropylethylamine are preferred.

Amount of the base used to one equivalent of the compound (4) is usually from 1 to 10 equivalent(s) and, preferably, from 1 to 3 equivalent(s).

Examples of the compound $L_1$-Cl used in this step are methanesulfonyl chloride, trifluoromethanesulfonyl chloride, p-toluenesulfonyl chloride and benzenesulfonium chloride, etc. where methanesulfonyl chloride and p-toluenesulfonyl chloride are preferred.

Amount of the $L_1$-Cl used to one equivalent of the compound (4) is usually from 1 to 10 equivalent(s) and, preferably, from 1 to 3 equivalent(s).

There is no particular limitation for the reaction solvent so far as it does not affect the reaction and its examples are THF, methylene chloride, chloroform and ethyl acetate, etc. where THF, methylene chloride and chloroform are preferred.

Reaction temperature is usually from $0°$ C. to $100°$ C. and, preferably, from $0°$ C. to $50°$ C.

Reaction time is usually from 5 minutes to 12 hours and, preferably, from 5 minutes to 4 hours.

The compound (5) prepared as such can be subjected to the next step with or without isolation and purification by a known separation and purification means such as concentration, concentration in vacuo, crystallization, extraction with solvent, reprecipitation and chromatography.

(Step 5)

This step is a process for producing a compound (6) by the reaction of the compound (5) produced in the above-mentioned step 4 with a CN compound.

Specific examples of the CN compound used in this step are tetraethylammonium cyanide, tetrabutylammonium cyanide, sodium cyanide and potassium cyanide, etc. where tetraethylammonium cyanide and tetrabutylammonium cyanide are preferred.

Amount of the cyano compound to one equivalent of the compound (5) is usually from 1 to 20 equivalent(s) and, preferably, from 1 to 5 equivalent(s).

There is no particular limitation for the reaction solvent so far as it does not affect the reaction and its examples are N,N-dimethylformamide, THF, dimethyl sulfoxide and acetonitrile, etc. where N,N-dimethylformamide is preferred.

Reaction temperature is usually from 0° C. to 150° C. and, preferably, from 50° C. to 100° C.

Reaction time is usually from 1 hour to 48 hours and, preferably, from 1 hour to 24 hours.

The compound (6) prepared as such can be subjected to the next step with or without isolation and purification by a known separation and purification means such as concentration, concentration in vacuo, crystallization, extraction with solvent, reprecipitation and chromatography.

(Step 6)

This step is a process to produce a compound (7) by hydrolysis of the compound (6) produced in the above-mentioned step 5 in the presence of an acid.

Examples of the acid used are sulfuric acid and hydrochloric acid, etc.

Amount of the acid used to one equivalent of the compound (6) is usually from 1 to 100 equivalent(s) and, preferably, from 1 to 50 equivalent(s).

There is no particular limitation for the reaction solvent so far as it does not affect the reaction and its examples are dioxane and water, etc.

Reaction temperature is usually from 20° C. to 200° C. and, preferably, from 50° C. to 150° C.

Reaction time is usually from 1 hour to 72 hours and, preferably, from 1 hour to 24 hours.

The compound (7) prepared as such can be subjected to the next step with or without isolation and purification by a known separation and purification means such as concentration, concentration in vacuo, crystallization, extraction with solvent, reprecipitation and chromatography.

(Step 7)

This step is a process for producing a compound (I-1) of the present invention by the reaction of the compound (7) produced in the above-mentioned step 6 with a compound (IV-1), (IV-2), (IV-3), (IV-4) or (IV-5).

In this reaction, a common amidation reaction is carried out by a method mentioned in documents (such as "Peptide Synthesis—Fundamentals and Experiments" (in Japanese) by Nobuo Izumiya, et al., Maruzen, 1983; "Comprehensive Organic Synthesis", volume 6, Pergamon Press, 1991; etc.), by a method similar thereto or by combination of such methods with a conventional method. Thus, it may be carried out using a condensing agent which has been known among the persons skilled in the art or by means of ester-activating method, mixed acid anhydride method, acid chloride method, carbodiimide method, etc. which can be utilized by the persons skilled in the art. Examples of an amide-forming reagent as such are thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, 2-chloro-1,3-dimethylimidazolinium chloride, ethyl chloroformate, isobutyl chloroformate, O-(7-azabenzotriazol-1-yl)-1,1,3,3-tetramethyluronium hexafluorophosphate (hereinafter, referred to as "HATU") and benzotriazo-1-yloxy-tris(dimethylamino)phosphonium hexafluorophosphate, etc. where thionyl chloride, 1-ethyl-3-(3-dimethylaminopropyl)carbodiimide hydrochloride, 2-chloro-1,3-dimethylimidazolinium chloride, N,N-dicyclohexylcarbodiimide, HATU and benzotriazo-1-yloxy-tris(dimethylamino)phosphonium hexafluorophosphate are preferred. In the amide-forming reaction, it is also possible to use a base and a condensing promoter together with the above-mentioned amide-forming reagent.

Examples of the base used are a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-azabicyclo[4.3.0]non-5-ene (DBN), etc.; an aromatic amine such as pyridine, 4-dimethylaminopyridine, picoline, lutidine, quinoline and isoquinoline; etc. Among them, the tertiary aliphatic amine is preferred and, for example, triethylamine or N,N-diisopropylamine is particularly preferred.

Examples of the condensing promoter used are N-hydroxybenzotriazole hydrate, N-hydroxysuccinimide, N-hydroxy-5-norbornene-2,3-dicarboxylmide and 3-hydroxy-3,4-dihydro-4-oxo-1,2,3-benzotriazole, etc. where N-hydroxybenzotriazole, etc. are preferred.

Amount of the compound (IV-1), (IV-2), (IV-3), (IV-4) or (IV-5) to one equivalent of the carboxylic acid derivative (7) or a reactive derivative thereof is usually from 0.1 to 10 equivalent(s) and, preferably, from 0.5 to 3 equivalent(s).

The compound (IV-1) used means an amino compound corresponding to the aforementioned compound (II-1) and, to be more specific, an amino compound corresponding to the aforementioned (II-1-1) may be exemplified.

The compound (IV-2) used means an amino compound corresponding to the aforementioned compound (II-2) and, to be more specific, an amino compound corresponding to the aforementioned (II-2-1) may be exemplified.

The compound (IV-3) used means an amino compound corresponding to the aforementioned compound (II-3) and, to be more specific, an amino compound corresponding to the aforementioned (II-3-1) may be exemplified.

The compound (IV-4) used means an amino compound corresponding to the aforementioned compound (II-4) and, to be more specific, an amino compound corresponding to the aforementioned (II-4-1) may be exemplified.

The compound (IV-5) used means an amino compound corresponding to the aforementioned compound (II-5) and, to be more specific, an amino compound corresponding to the aforementioned (II-5-1) may be exemplified.

Although the amount of the amide-forming reagent used varies depending upon the compound used, type of the solvent and other reaction conditions, it is usually from 1 to 10 equivalent(s) and, preferably, from 1 to 3 equivalent(s) to one equivalent of the carboxylic acid compound (7) or a reactive derivative thereof.

Although the amount of the condensing promoter used varies depending upon the compound used, type of the solvent and other reaction conditions, it is usually from 1 to 10 equivalent(s) and, preferably, from 1 to 3 equivalent(s) to one equivalent of the carboxylic acid compound (7) or a reactive derivative thereof.

Amount of the base used is usually from 1 to 10 equivalent(s) and, preferably, from 1 to 5 equivalent(s).

With regard to a reaction solvent used in this step, an inert solvent is exemplified and, although there is no particular limitation therefor so far as it does not affect the reaction, its specific examples are methylene chloride, chloroform, 1,2-dichloroethane, N,N-dimethylformamide, ethyl acetate, methyl acetate, acetonitrile, benzene, xylene, toluene, 1,4-dioxane, tetrahydrofuran, dimethoxyethane and mixed solvent thereof. In view of securing the advantageous reaction temperature, examples of the preferred one are methylene chloride, chloroform, 1,2-dichloroethane, acetonitrile and N,N-dimethylformamide, etc.

Reaction temperature in this step is usually from −78° C. to a boiling point of the solvent and, preferably, from 0° C. to 30° C.

Reaction time in this step is usually from 0.5 to 96 hour(s) and, preferably, from 3 hour to 24 hours.

With regard to the base, the amide-forming reagent and a condensing promoter used in this step, one of them or two or more of them in a combination thereof may be able to be used.

The compound (I-1) of the present invention prepared as such can be subjected to isolation and purification by a known separation and purification means such as concentration, concentration in vacuo, crystallization, extraction with solvent, reprecipitation and chromatography.

The compound (I-2) of the present invention is also able to be produced by the following method.

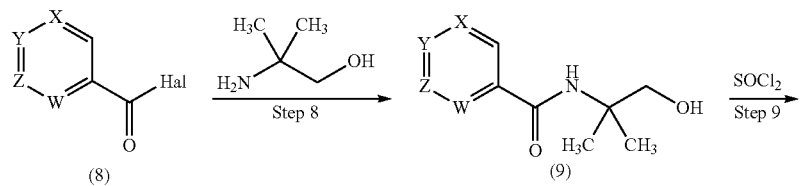

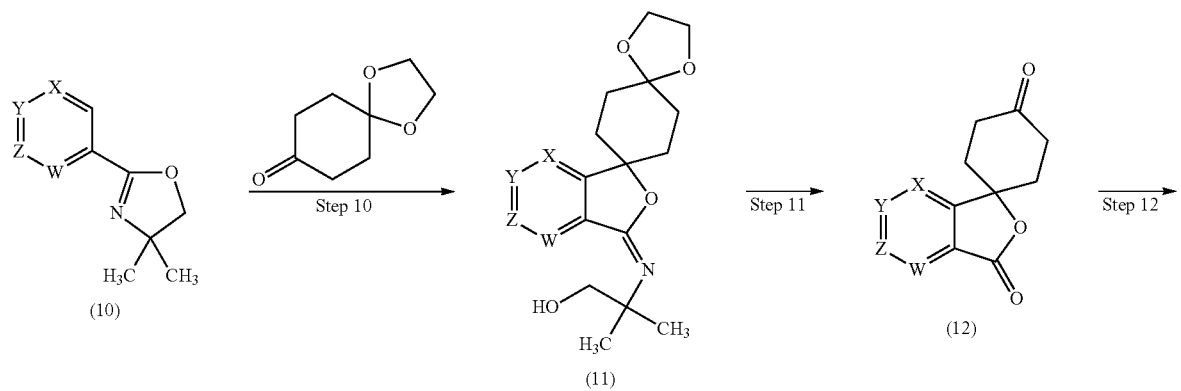

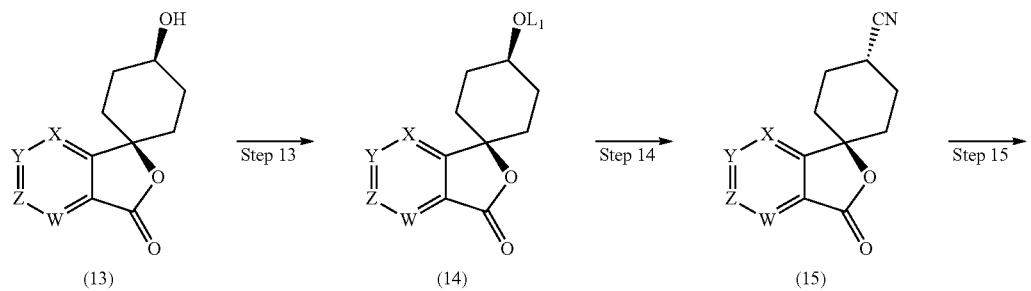

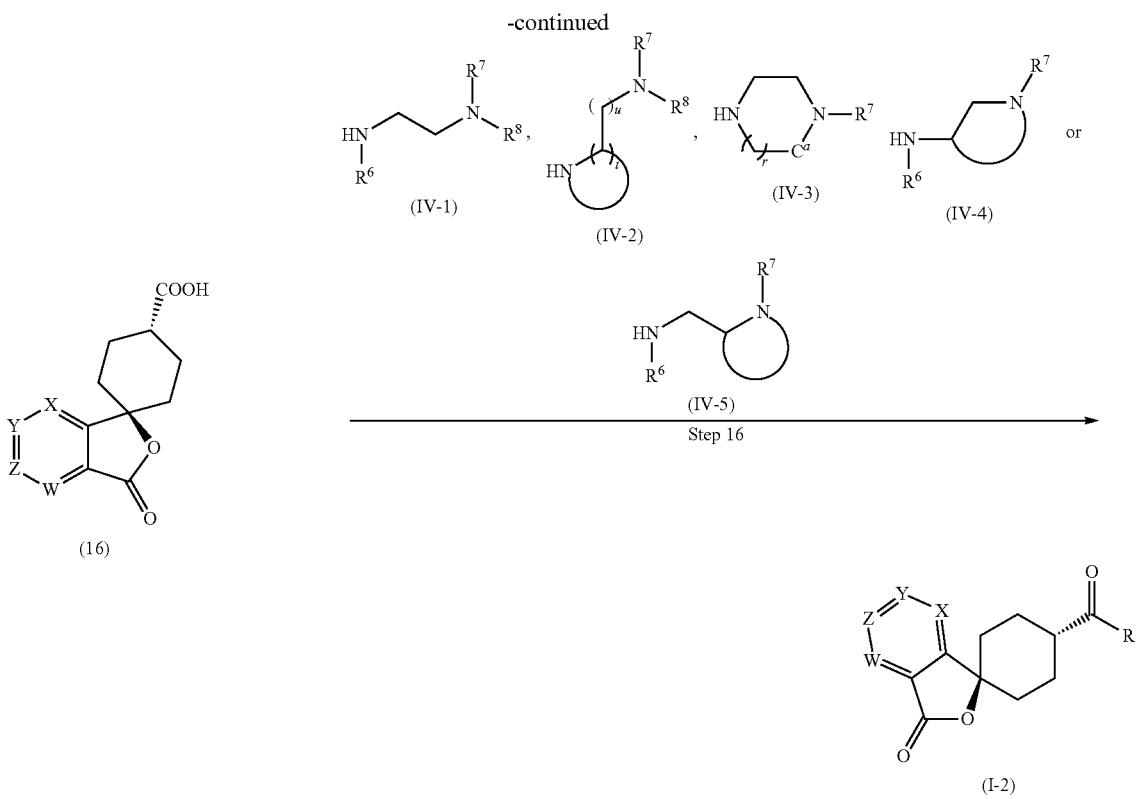

[wherein, the symbols have the same meanings as above.]
(Step 8)

This step is a process for producing a compound (9) by the reaction of a compound (8) with 1,1-dimethyl-2-hydroxyethylamine in the presence of a base.

Examples of the base used in this step are triethylamine, trimethylamine, N,N-diisopropylethylamine, N-methylmorpholine and pyridine, etc. and, among them, triethylamine, N,N-diisopropylamine and pyridine are preferred.

Amount of the base used to one equivalent of the compound (8) is usually from 1 to 10 equivalent(s) and, preferably, from 1 to 3 equivalent(s).

Reaction temperature is usually from −78° C. to 100° C. and, preferably, from 0° C. to 50° C.

Reaction time is usually from 10 minutes to 48 hours and, preferably, from 30 minutes to 24 hours.

There is no particular limitation for the reaction solvent so far as it does not affect the reaction and, to be more specific, its examples are chloroform, methylene chloride, 1,2-dichloroethane, THF, ethyl acetate, acetonitrile, 1,4-dioxane, toluene and dimethoxyethane, etc. where chloroform, methylene chloride and THF are preferred.

The compound (9) prepared as such can be subjected to the next step with or without isolation and purification by a known separation and purification means such as concentration, concentration in vacuo, crystallization, extraction with solvent, reprecipitation and chromatography.

(Step 9)

This step is a process for producing a compound (10) by the reaction of the compound (9) produced in the above-mentioned step 8 with thionyl chloride.

In place of thionyl chloride, it is also possible to use sulfuryl chloride, phosphorus oxychloride, etc.

Amount of thionyl chloride used to one equivalent of the compound (9) is usually from 1 to 10 equivalent(s) and, preferably, from 1 to 3 equivalent(s).

Reaction temperature is usually from 0° C. to 100° C. and, preferably, from 0° C. to 50° C.

Reaction time is usually from 10 minutes to 48 hours and, preferably, from 10 minutes to 24 hours.

With regard to the reaction solvent used in this step, anything may be used so far as it does not affect the reaction and its examples are benzene, methylene chloride and 1,2-dichloroethane, etc.

The compound (10) prepared as such can be subjected to the next step with or without isolation and purification by a known separation and purification means such as concentration, concentration in vacuo, crystallization, extraction with solvent, reprecipitation and chromatography.

(Step 10)

This step is a process to produce a compound (11) by the reaction of the compound (10) prepared in the above-mentioned step 9 with 1,4-cyclohexanedione-monoethylene ketal in the presence of a base.

With regard to the base used in this step, butyl lithium, lithium 2,2,6,6-tetramethylpiperidide, etc. may be exemplified and butyl lithium is preferred.

Amount of the base used to one equivalent of the compound (10) is usually from 1 to 10 equivalent(s) and, preferably, from 1 to 3 equivalent(s).

Amount of 1,4-cyclohexanedione-monoethylene ketal used in this step to one equivalent of the compound (10) is usually from 1 to 10 equivalent(s) and, preferably, from 1 to 3 equivalent(s).

Reaction temperature is usually from −78° C. to 100° C. and, preferably, from −78° C. to 50° C.

Reaction time is usually from 10 minutes to 24 hours and, preferably, from 10 minutes to 12 hours.

With regard to the reaction solvent used in this step, anything may be used so far as it does not affect the reaction and its examples are THF, diethyl ether and tert-butyl methyl ether, etc. where THF is preferred.

The compound (11) prepared as such can be subjected to the next step with or without isolation and purification by a known separation and purification means such as concentration, concentration in vacuo, crystallization, extraction with solvent, reprecipitation and chromatography.

(Step 11)

This step is a process to produce a compound (12) by the reaction of the compound (11) prepared in the above-mentioned step 10 with an acid.

With regard to the acid used in this step, sulfuric acid, hydrochloric acid, p-toluenesulfonic acid, trifluoroacetic acid, etc. are exemplified.

Amount of the acid used to one equivalent of the compound (11) is usually from 0.1 to 100 equivalent(s) and, preferably, from 0.1 to 10 equivalent(s).

Reaction temperature is usually from 0° C. to 200° C. and, preferably, from 20° C. to 100° C.

Reaction time is usually from 1 hour to 72 hours and, preferably, from 1 hour to 48 hours.

With regard to the reaction solvent used in this step, anything may be used so far as it does not affect the reaction and its examples are water, acetone, THF and 1,4-dioxane, etc. where acetone, THF, etc. are preferred.

The compound (12) prepared as such can be subjected to the next step with or without isolation and purification by a known separation and purification means such as concentration, concentration in vacuo, crystallization, extraction with solvent, reprecipitation and chromatography.

(Step 12)

This step is a process for producing a compound (13) by subjecting the compound (12) produced in the above-mentioned step 11 to a reduction reaction.

The reaction in this step may be carried out by the same method as in the aforementioned step 3, by a method similar thereto or by a combination thereof with a conventional method.

The compound (13) prepared as such can be subjected to the next step with or without isolation and purification by a known separation and purification means such as concentration, concentration in vacuo, crystallization, extraction with solvent, reprecipitation and chromatography.

(Step 13)

This step is a process for producing a compound (14) by the reaction of the compound (13) produced in the above-mentioned step 12 with a compound $L_1$-Cl in the presence of a base.

The reaction in this step may be carried out by the same method as in the aforementioned step 4, by a method similar thereto or by a combination thereof with a conventional method.

The compound (14) prepared as such can be subjected to the next step with or without isolation and purification by a known separation and purification means such as concentration, concentration in vacuo, crystallization, extraction with solvent, reprecipitation and chromatography.

(Step 14)

This step is a process for producing a compound (15) by the reaction of the compound (14) produced in the above-mentioned step 13 with a CN compound.

The reaction in this step may be carried out by the same method as in the aforementioned step 5, by a method similar thereto or by a combination thereof with a conventional method.

The compound (15) prepared as such can be subjected to the next step with or without isolation and purification by a known separation and purification means such as concentration, concentration in vacuo, crystallization, extraction with solvent, reprecipitation and chromatography.

(Step 15)

This step is a process for producing a compound (16) by hydrolysis of the compound (15) produced in the above-mentioned step 14.

The reaction in this step may be carried out by the same method as in the aforementioned step 6, by a method similar thereto or by a combination thereof with a conventional method.

The compound (16) prepared as such can be subjected to the next step with or without isolation and purification by a known separation and purification means such as concentration, concentration in vacuo, crystallization, extraction with solvent, reprecipitation and chromatography.

(Step 16)

This step is a process for producing a compound (I-2) of the present invention by the reaction of the compound (16) produced in the above-mentioned step 15 with a compound (IV-1), (IV-2), (IV-3), (IV-4) or (IV-5).

The reaction in this step may be carried out by the same method as in the aforementioned step 7, by a method similar thereto or by a combination thereof with a conventional method.

Examples of the compound (IV-1) are N-methyl-N-(piperidinoethyl)amine, N-methyl-N-(pyrrolidinoethyl)amine, 1-(2-aminoethyl)piperidine, 1-(2-aminoethyl)pyrrolidine, N,N,N'-trimethylethylenediamine, N-cyclohexyl-N,N'-dimethylethylenediamine and N-ethyl-N-(piperidinoethyl)amine, etc.

Examples of the compound (IV-2) are (S)-1-(2-pyrrolidinylmethyl)pyrrolidine, (S)-1-(2-pyrrolidinylmethyl)piperidine, (S)-1-(2-piperidinylmethyl)piperidine and (S)-1-(2-piperidinylmethyl)pyrrolidine, etc.

Examples of the compound (IV-3) are 1-methylpiperazine, 1-isobutylpiperazine, 1-cyclopentylpiperazine, (R)-octahydropyrrolo[1,2-a]pyrazine and 1-ethyl-(3S)-methylpiperazine, etc. Examples of the compound (IV-4) are N-(1-cyclopentyl-3-pyrrolidinyl)-N-methylamine and N-(1-isobutyl-3-pyrrolidinyl)-N-methylamine, etc.

Examples of the compound (IV-5) are 1-(1-isopropylpyrrolidin-2-yl)-N-methyl-methanamine, etc.

The compound (I-2) prepared as such can be isolated and purified by a known separation and purification means such as concentration, concentration in vacuo, crystallization, extraction with solvent, reprecipitation and chromatography.

The compound of the present invention (I-3), (I-4) or (I-5) also can be produced by, for example, the following method.

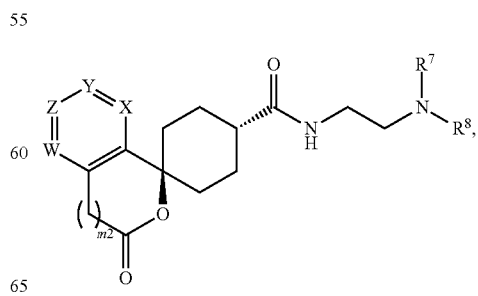

(I-1-1)

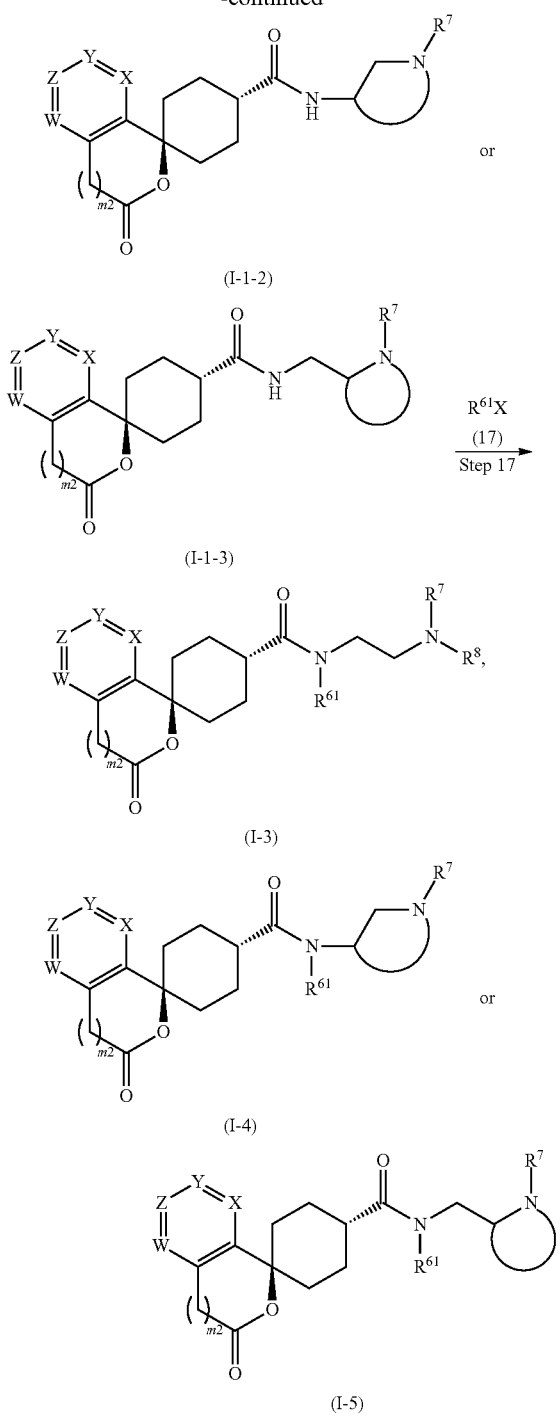

[wherein, R⁶¹ represents a lower alkyl group, X represents a halogen atom and other symbols have the same meanings as above.]

(Step 17)

This step is a process for producing the compound (I-3), (I-4) or (I-5) of the present invention by the reaction of the compound represented by the formula (I-1-1), (I-1-2) or (I-1-3) which is the compound of the present invention covered by the aforementioned formula (I-1) with the compound (17) in the presence of a base.

Examples of the base used are sodium hydride, potassium hydride, calcium hydride and butyl lithium, etc. Among them, NaH is preferred.

Amount of the base used to one equivalent of the compound (I-1-1), (I-1-2) or (I-1-3) is usually form 1 to 10 equivalent(s) and, preferably, from 1 to 3 equivalent(s).

Specific examples of the compound (17) used are ethyl iodide, methyl iodide, methyl trifluoromethylsulfonate, methyl methylsulfonate, methyl p-toluenesulfonate, methyl bromide and ethyl bromide, etc.

Amount of the compound (17) used to one equivalent of the compound (I-1-1), (I-1-2) or (I-1-3) is usually from 1 to 10 equivalent(s) and, preferably, from 1 to 3 equivalent(s).

With regard to the reaction solvent used in this step, there is no particular limitation so far as it does not affect the reaction and its examples are N,N-dimethylformamide and THF, etc.

Reaction temperature is usually from −78° C. to 100° C. and, preferably, from 0° C. to 50° C.

Reaction time is usually from 10 minutes to 48 hours and, preferably, from 10 minutes to 24 hours.

The compound (I-3), (I-4) or (I-5) prepared as such can be isolated and purified by a known separation and purification means such as concentration, concentration in vacuo, crystallization, extraction with solvent, reprecipitation and chromatography.

The compound (I-6) of the present invention can be produced by, for example, the following method.

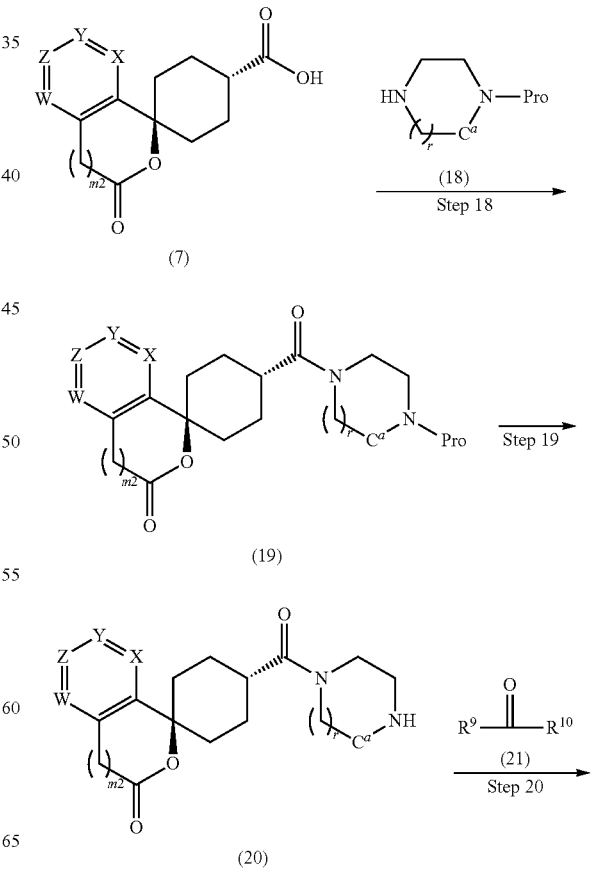

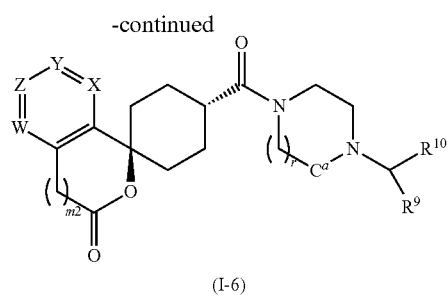

(I-6)

[wherein, Pro represents a protective group for amino group, $R^9$ represents a hydrogen atom or a lower alkyl group, $R^{10}$ represents a hydrogen atom, a lower alkyl group, an aryl group or a heteroaryl group or $R^9$ and $R^{10}$ together form a three- to nine-membered cycloalkyl group and other symbols have the same meanings as above.]

(Step 18)

This step is a process to produce a compound (19) by the reaction of the above-mentioned compound (7) with the compound (18).

In this reaction, a common amidation reaction is carried out by a method mentioned in documents (such as "Peptide Synthesis—Fundamentals and Experiments" (in Japanese) by Nobuo Izumiya, et al., Maruzen, 1983; "Comprehensive Organic Synthesis", volume 6, Pergamon Press, 1991; etc.), by a method similar thereto or by combination of such methods with a conventional method. Thus, it may be carried out using a condensing agent which has been known among the persons skilled in the art or by means of ester-activating method, mixed acid anhydride method, acid chloride method, carbodiimide method, etc. which can be utilized by the persons skilled in the art. Examples of an amide-forming reagent as such are thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, HATU and benzotriazo-1-yloxy-tris (dimethylamino)phosphonium hexafluorophosphate, etc. where thionyl chloride, 1-ethyl-3-(3-dimethylaminopropyl) carbodiimide hydrochloride, N,N-dicyclohexylcarbodiimide, HATU and benzotriazo-1-yloxy-tris(dimethylamino) phosphonium hexafluorophosphate, etc. are preferred. In the amide-forming reaction, it is also possible to use a base and a condensing promoter together with the above-mentioned amide-forming reagent.

Examples of the base used are a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0] undec-7-ene (DBU) and 1,5-azabicyclo[4.3.0]non-5-ene (DBN), etc.; an aromatic amine such as pyridine, 4-dimethylaminopyridine, picoline, lutidine, quinoline and isoquinoline; etc. Among them, the tertiary aliphatic amine is preferred and, for example, triethylamine or N,N-diisopropylethylamine, etc. is particularly preferred.

Examples of the condensing promoter used are N-hydroxybenzotriazole hydrate, N-hydroxysuccinimide, N-hydroxy-5-norbornene-2,3-carboxylmide and 3-hydroxy-3,4-dihydro-4-oxo-1,2,3-benzotriazole, etc. where N-hydroxybenzotriazole, etc. are preferred.

Amount of the compound (18) used to one equivalent of the carboxylic acid derivative (7) or a reactive derivative thereof is usually from 0.1 to 10 equivalent(s) and, preferably, from 0.5 to 3 equivalent(s).

Examples of the compound (18) used are 1-Boc-piperazine, 1-Boc-homopiperazine, 1-benzyloxycarbonylpiperazine, 1-acetylpiperazine, 1-benzoylpiperazine and 1-benzylpiperazine, etc.

Although the amount of the amide-forming reagent used varies depending upon the compound used, type of the solvent and other reaction conditions, it is usually from 1 to 10 equivalent(s) and, preferably, from 1 to 3 equivalent(s) to one equivalent of the carboxylic acid compound (7) or a reactive derivative thereof.

Although the amount of the condensing promoter used varies depending upon the compound used, type of the solvent and other reaction conditions, it is usually from 1 to 10 equivalent(s) and, preferably, from 1 to 3 equivalent(s) to one equivalent of the carboxylic acid compound (7) or a reactive derivative thereof.

Amount of the base used is usually from 1 to 10 equivalent(s) and, preferably, from 1 to 5 equivalent(s).

With regard to a reaction solvent used in this step, an inert solvent is exemplified and, although there is no particular limitation therefor so far as it does not affect the reaction, its specific examples are methylene chloride, chloroform, 1,2-dichloroethane, N,N-dimethylformamide, ethyl acetate, methyl acetate, acetonitrile, benzene, xylene, toluene, 1,4-dioxane, tetrahydrofuran, dimethoxyethane and a mixed solvent thereof. In view of securing the advantageous reaction temperature, examples of the preferred one are methylene chloride, chloroform, 1,2-dichloroethane, acetonitrile and N,N-dimethylformamide, etc.

Reaction temperature in this step is usually from −78° C. to a boiling point of the solvent and, preferably, from 0° C. to 30° C.

Reaction time in this step is usually from 0.5 to 96 hour(s) and, preferably, from 3 hour to 24 hours.

With regard to the base, the amide-forming reagent and a condensing promoter used in this step, one or more thereof may be able to be combined and used.

The compound (19) prepared as such can be subjected to the next step with or without isolation and purification by a known separation and purification means such as concentration, concentration in vacuo, crystallization, extraction with solvent, reprecipitation and chromatography.

(Step 19)

This step is a method to produce a compound (20) by removing the protective group for amino group of the compound (19) produced in the above-mentioned step 18.

Removal of the protective group for amino group can be carried out by a method mentioned in a document (such as "Protective Groups in Organic Synthesis" by T. W. Green, second edition, John Wiley & Sons, 1991), by a method similar thereto or by combining those methods with a conventional method.

The compound (20) prepared as such can be subjected to the next step with or without isolation and purification by a known separation and purification means such as concentration, concentration in vacuo, crystallization, extraction with solvent, reprecipitation and chromatography.

(Step 20)

This step is a method for producing a compound (I-6) of the present invention by the reaction of the compound (20) produced in the above-mentioned step 18 with the compound (21).

The reaction in this step is the so-called reductive alkylation and the compound (I-6) of the present invention can be produced by the reaction of the compound (20) with the compound (21) in the presence of a base and a reducing agent.

Examples of the compound (21) used are cyclobutanone, cyclopentanone, cyclohexanone, cycloheptanone, acetone, 3-pentanone, 2-butanone, 3-methyl-2-butanone, 3-hexanone, formaldehyde, acetaldehyde, propionaldehyde and isobutylaldehyde, etc.

Amount of the compound (21) used to one equivalent of the compound (20) is usually from 1 to 10 equivalent(s) and, preferably, from 1 to 3 equivalent(s).

Examples of the base used are triethylamine, trimethylamine, N,N-diisopropylethylamine, N-methylmorpholine, N-methylpyrrolidine and N-methylpiperidine, etc.

Amount of the base used to one equivalent of the compound (20) is usually from 0 to 5 equivalent(s) and, preferably, from 0 to 2 equivalent(s).

Examples of the reducing agent used are $ZnCl_2$—$NaBH_3CN$, acetic acid-$NaBH_3CN$, acetic acid-$NaBH(OAc)_3$ and sodium borohydride, etc. and, among them, $ZnCl_2$—$NaBH_3CN$, acetic acid-$NaHB_3CN$, etc. are preferred.

Amount of the reducing agent used to one equivalent of the compound (20) is usually from 1 to 20 equivalent(s) and, preferably, from 1 to 5 equivalent(s).

There is no particular limitation for the reaction solvent used in this step so far as it does not affect the reaction and its examples are methanol, ethanol, chloroform, methylene chloride, THF and 1,4-dioxane where methanol, ethanol and methylene chloride are preferred.

Reaction temperature is usually from 0° C. to 100° C. and, preferably, from 0° C. to 50° C.

Reaction time is usually from 10 minutes to 48 hours and, preferably, from 10 minutes to 24 hours.

The compound (I-6) prepared as such can be isolated and purified by a known separation and purification means such as concentration, concentration in vacuo, crystallization, extraction with solvent, reprecipitation and chromatography.

The compound (I-2-1) of the present invention

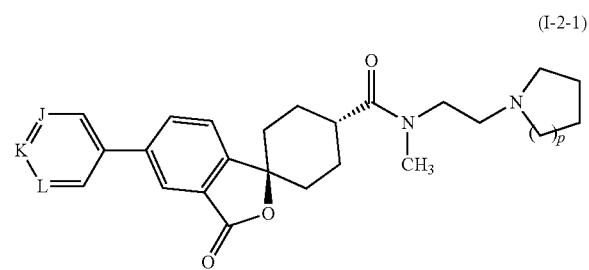

(I-2-1)

[wherein, any one or two of J, K and L is/are nitrogen atom(s) while other(s) is/are carbon atom(s), p is 1 or 2,

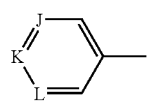

wherein (I-2-1) may be substituted with a lower alkyl group, a lower alkoxy group, a halogen atom, a cyano group, etc. and other symbols have the same meanings as above] or a pharmaceutically acceptable salt thereof can be produced by, for example, the following method

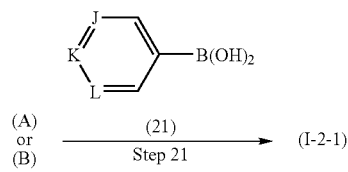

[wherein, the symbols have the same meanings as above] using trans-5'-{[(trifluoromethyl)-sulfonyl]oxy}-3'-oxo-N-methyl-N-(2-pyrrolidin-1-ylethyl)-spiro[cyclohexane-1,1'-(3'H)-isobenzofuran]-4-carboxamide (hereinafter, it may be abbreviated as a compound (A)) which is a compound of Example 52 produced from trans-5'-hydroxy-3'-oxo-N-methyl-N-(2-pyrrolidin-1-ylethyl)-spiro[cyclohexane-1,1'-(3'H)-isobenzofuran]-4-carboxamide (hereinafter, it may be abbreviated as a compound I-A) produced in Example 20 as a starting material or by using trans-5'-{[(trifluoromethyl)-sulfonyl]oxy}-3'-oxo-N-methyl-N-(2-piperidin-1-ylethyl)-spiro[cyclohexane-1,1'-(3'H)-isobenzofuran]-4-carboxamide (hereinafter, it may be abbreviated as a compound (B)) which is a compound of Example 51 produced from trans-5'-hydroxy-3'-oxo-N-methyl-N-(2-piperidin-1-ylethyl)-spiro[cyclohexane-1,1'-(3'H)-isobenzofuran]-4-carboxamide (hereinafter, it may be abbreviated as a compound I-B) produced in Example 23 as a starting material.

(Step 21)

This step is a method for producing the compound (I-2-1) of the present invention by the reaction of the compound (A) or (B) with the compound (21) in the presence of a base and a palladium catalyst.

Examples of the base used are sodium carbonate, cesium carbonate, cesium fluoride, calcium carbonate, sodium hydride, sodium carbonate, potassium carbonate, potassium phosphate, potassium acetate, potassium tert-butoxide and triethylamine, etc.

Amount of the base to one equivalent of the compound (A) or (B) is usually from 0.1 to 20 equivalent(s) and, preferably, from 1 to 5 equivalent(s).

Examples of the palladium catalyst used are tetrakistriphenylphosphine palladium, dichlorobistriphenylphosphine palladium, dichloro(1,1'-bis(diphenylphosphino)ferrocene) palladium and palladium acetate, etc.

Amount of the palladium catalyst to one equivalent of the compound (A) or (B) is usually from 0.01 to 10 equivalent(s) and, preferably, from 0.05 to 5 equivalent(s).

Specific examples of the compound (21) used are pyridin-3-ylboronic acid, pyridin-4-ylboronic acid, pyrimidin-5-ylboronic acid, 2-methoxypyrimidin-5-ylboronic acid, 2-methoxypyridin-5-ylboronic acid and 2-methylpyridin-5-ylboronic acid, etc.

There is no particular limitation for the reaction solvent so far as it does not affect the reaction and examples thereof are ethylene glycol dimethyl ether, N,N-dimethylformamide, toluene, THF, 1,4-dioxane, benzene, acetone and methanol, etc.

Reaction temperature is usually from 0° C. to refluxing temperature of the reaction solvent and, preferably, from room temperature to 150° C. Reaction time is usually from 0.1 hour to 72 hours and, preferably, from 0.5 hour to 12 hours.

The compound (I-2-1) prepared as such can be isolated and purified by a known separation and purification means such as concentration, concentration in vacuo, crystallization, extraction with solvent, reprecipitation and chromatography.

The compound represented by the formula (I-2-2)

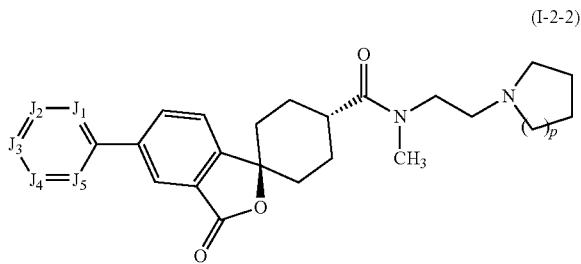

[wherein, one or two of $J_1$ to $J_5$ is/are nitrogen atom(s) while others are carbon atoms (with a proviso that at least one of $J_1$ and $J_2$ is a nitrogen atom),

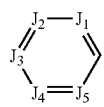

may be substituted by a lower alkyl group, a lower alkoxy group, halogen atom or cyano group and other symbols have the same meanings as above] of the present invention may, for example, be produced by the following method.

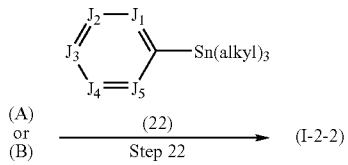

[wherein, the symbols have the same meanings as above.]

(Step 22)

This step is a method for producing the compound (I-2-2) by the reaction of the above-mentioned compound (A) or (B) with the compound (22) in the presence of lithium chloride and a palladium catalyst.

Amount of lithium chloride used to one equivalent of the compound (A) or (B) is usually from 0.01 to 10 equivalent(s) and, preferably, form 0.05 to 5 equivalent(s).

Examples of the palladium catalyst used are tetrakistriphenylphosphine palladium, dichlorobistriphenylphosphine palladium, dichloro(1,1'-bis(diphenylphosphino)ferrocene) palladium and palladium acetate, etc. Amount of the palladium catalyst to one equivalent of the compound (A) or (B) is usually form 0.01 to 10 equivalent(s) and, preferably, from 0.05 to 5 equivalent(s).

Examples of the compound (22) used are 2-(tri-n-butyl tin)pyrazine and 2-(tri-n-butyl tin)pyridine, etc.

Amount of the compound (22) to one equivalent of the compound (A) or (B) is usually from 0.1 to 50 equivalent(s) and, preferably, from 1 to 10 equivalent(s).

There is no particular limitation for the reaction solvent so far as it does not affect the reaction and examples thereof are N,N-dimethylformamide, toluene, THF, 1,4-dioxane, benzene and acetone, etc.

Reaction temperature is usually from 0° C. to refluxing temperature of the reaction solvent and, preferably, from room temperature to 150° C.

Reaction time is usually from 0.1 hour to 72 hours and, preferably, from 0.5 hour to 12 hours.

The compound (I-2-2) prepared as such can be isolated and purified by a known separation and purification means such as concentration, concentration in vacuo, crystallization, extraction with solvent, reprecipitation and chromatography.

The compound of the present invention represented by the formula (I-2-3)

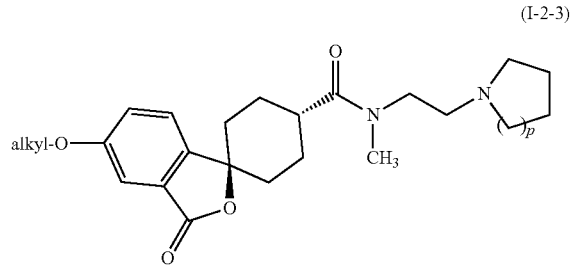

[wherein, alkyl represents a lower alkyl group having 1 to 6 carbon(s) and other symbols have the same meanings as above] can be produced by, for example, the following method.

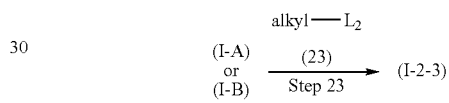

[wherein, alkyl represents a linear or branched alkyl group having 1 to 6 carbon(s) (the alkyl group may be substituted with one to three halogen atom(s) being same or different) and $L_2$ is a leaving group.]

(Step 23)

This step is a method for producing the compound (I-2-3) of the present invention by the reaction of the above-mentioned compound (I-A) or (I-B) with an alkyl halide (23) in the presence of a base.

Examples of the base used are cesium carbonate, potassium carbonate, sodium carbonate and sodium hydride, etc.

Amount of the base to one equivalent of the compound (I-A) or (I-B) is usually from 0.1 to 20 equivalent(s) and, preferably, from 1 to 5 equivalent(s). Examples of the compound (23) used are methyl iodide, ethyl iodide, propyl iodide, butyl iodide and 2-fluoro-1-(fluoromethyl)ethyl methanesulfonate, etc.

Amount of the alkyl halide (23) to one equivalent of the compound (I-A) or (I-B) is usually from 0.1 to 50 equivalent(s) and, preferably, from 1 to 10 equivalent(s).

There is no particular limitation for the reaction solvent so far as it does not affect the reaction and examples thereof are N,N-dimethylformamide, toluene, acetone, 1,4-dioxane and benzene, etc.

Reaction temperature is usually from 0° C. to refluxing temperature of the reaction solvent and, preferably, from room temperature to 150° C.

Reaction time is usually from 0.1 hour to 72 hours and, preferably, from 0.5 hour to 12 hours.

The compound (I-2-3) prepared as such can be isolated and purified by a known separation and purification means such as concentration, concentration in vacuo, crystallization, extraction with solvent, reprecipitation and chromatography.

The compound of the present invention represented by the formula (I-2-4)

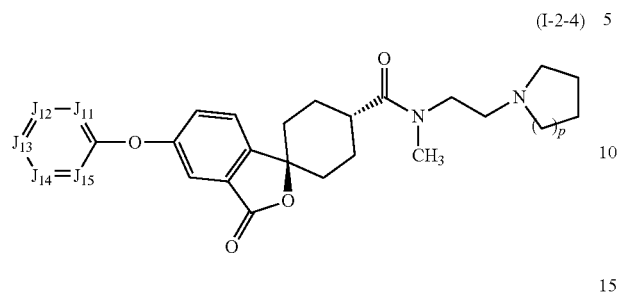
(I-2-4)

[wherein, one or two of $J_{11}$ to $J_{15}$ is/are nitrogen atom(s) while others are carbon atoms,

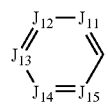

may be substituted with a lower alkyl group, a lower alkoxy group, halogen atom or cyano group and other symbols have the same meanings as above] may be produced by, for example, the following method.

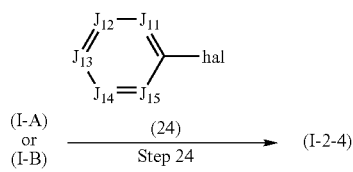

[wherein, hal represents a halogen atom and other symbols have the same meanings as above.]

(Step 24)

This step is a method for producing the compound (I-2-4) of the present invention by the reaction of the above-mentioned compound (I-A) or (I-B) with a compound (25) in the presence of a base.

Examples of the base used are cesium carbonate, potassium carbonate, sodium carbonate, potassium phosphate and sodium hydride, etc.

Amount of the base to one equivalent of the compound (I-A) or (I-B) is usually from 0.1 to 20 equivalent(s) and, preferably, from 1 to 5 equivalent(s).

Examples of the compound (24) used are 2-fluoropyridine, 2-chloropyrimidine, 2-chloropyrazine, 2-chloro-2-methoxypyrimidine, 5-bromopyrimidine-2-carbonitrile and 2-chloro-5-fluoropyrimidine etc.

Amount of the compound (24) to one equivalent of the compound (I-A) or (I-B) is usually from 0.1 to 50 equivalent(s) and, preferably, from 1 to 10 equivalent(s).

There is no particular limitation for the reaction solvent so far as it does not affect the reaction and examples thereof are N,N-dimethylformamide, N-methyl-2-pyrrolidone, toluene, acetone, benzene, 1,4-dioxane and THF, etc.

Reaction temperature is usually from 0° C. to refluxing temperature of the reaction solvent and, preferably, from room temperature to 150° C.

Reaction time is usually from 0.1 hour to 72 hours and, preferably, from 0.5 hour to 12 hours.

The compound (I-2-4) prepared as such can be isolated and purified by a known separation and purification means such as concentration, concentration in vacuo, crystallization, extraction with solvent, reprecipitation and chromatography.

The compound of the present invention represented by the formula (I-2-5)

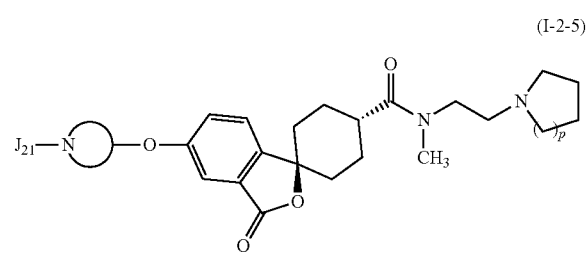
(I-2-5)

[wherein, $J_{21}$ represents a hydrogen atom, an alkanoyl group, a lower alkylsulfonyl group, diphenylmethyl group, formyl group or a lower alkoxycarbonyl group,

represents a four- to six-membered nitrogen-containing alicyclic group and other symbols have the same meanings as above] can be produced by, for example, the following method.

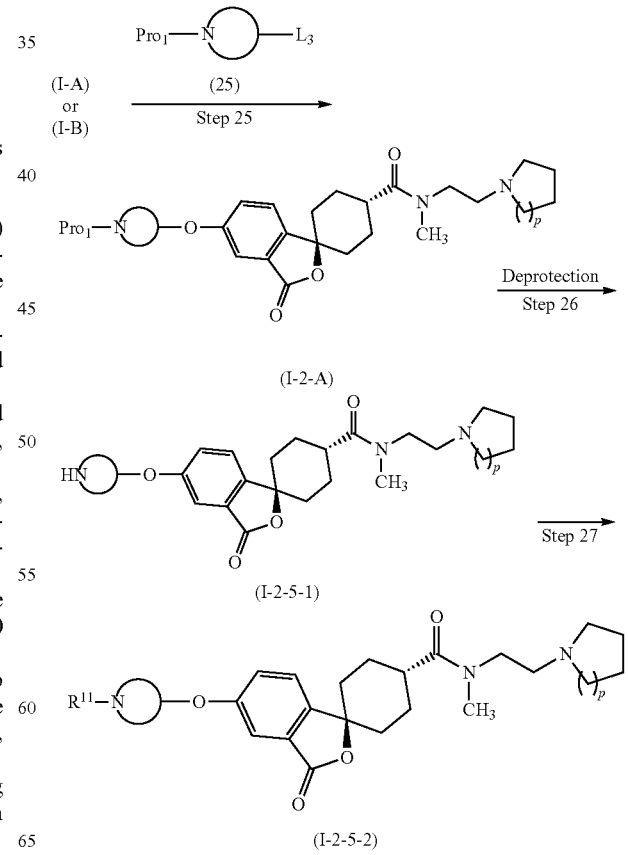

[wherein, Pro represents a protective group for amino group, $L_3$ represents a leaving group and other symbols have the same meanings as above.]

(Step 25)

This step is a method for producing the compound (I-2-A) of the present invention by the reaction of the above-mentioned compound (I-A) or (I-B) with a compound (25) in the presence of a base.

Examples of the base used are potassium carbonate, cesium carbonate, sodium hydride, potassium phosphate and sodium carbonate, etc.

Amount of the base to one equivalent of the compound (I-A) or (I-B) is usually from 0.1 to 20 equivalent(s) and, preferably, from 1 to 5 equivalent(s).

Amount of the compound (25) used to one equivalent of the compound (I-A) or (I-B) is usually from 0.1 to 50 equivalent(s) and, preferably, from 1 to 10 equivalent(s).

There is no particular limitation for the reaction solvent so far as it does not affect the reaction and examples thereof are N,N-dimethylformamide, N-methyl-2-pyrrolidone, toluene, acetone, benzene, 1,4-dioxane and THF, etc.

Reaction temperature is usually from 0° C. to refluxing temperature of the reaction solvent and, preferably, from room temperature to 150° C.

Reaction time is usually from 0.1 hour to 72 hours and, preferably, from 0.5 hour to 12 hours.

The compound (I-2-A) prepared as such can be isolated and purified by a known separation and purification means such as concentration, concentration in vacuo, crystallization, extraction with solvent, reprecipitation and chromatography.

With regard to $Pro_1$ in the compound (25), anything may be used so far as it acts as a protective group of an amino group and can be easily removed in deprotection and examples thereof are the protective groups used in a method mentioned in documents (such as "Protective Groups in Organic Synthesis" by T. W. Green, second edition, John Wiley & Sons, 1991.

With regard to $L_3$ in the compound (25), methanesulfonyloxy group may be exemplified.

The compound (25) can be produced, for example, by the reaction of tert-butyl 4-hydroxypiperidine-1-carboxylate, tert-butyl 2-hydroxypyrrolidine-1-carboxylate, 1-(diphenylmethyl)azetidin-3-ol or the like with methanesulfonyl chloride in the presence of a base such as triethylamine.

(Step 26)

This step is a method to produce a compound (I-2-5-1) of the present invention where $Pro_1$ is hydrogen atom by removing the protective group for amino group of the compound (I-2-A).

The reaction in this step can be carried out by a method mentioned in a document (such as "Protective Groups in Organic Synthesis" by T. W. Green, second edition, John Wiley & Sons, 1991), by a method similar thereto or by combining those methods with a conventional method.

The compound (I-2-5-1) prepared as such can be isolated and purified by a known separation and purification means such as concentration, concentration in vacuo, crystallization, extraction with solvent, reprecipitation and chromatography.

(Step 28)

In this step, $R^{11}$ is introduced into NH of the compound (I-2-5-1) produced in the above-mentioned step 27 whereupon a compound (I-2-5-2) can be produced.

Examples of $R^{11}$ are an alkanoyl group, a lower alkylsulfonyl group, diphenylmethyl group, formyl group or a lower alkoxycarbonyl group and more specific examples are acetyl group, propionyl group, methylsulfonyl group, ethylsulfonyl group, isopropylsulfonyl group, formyl group and methoxycarbonyl group, etc.

With regard to a method for introducing $R^{11}$ into the compound (I-2-5-1), it may be carried out according to a method which has been commonly used in the field of organic chemistry such as that mentioned in a document (such as "Protective Groups in Organic Synthesis" by T. W. Green, second edition, John Wiley & Sons, 1991), by a method similar thereto or by combining those methods with a conventional method.

The compound of the present invention represented by the formula (I-7), (I-8) or (I-9)

[wherein, the symbols have the same meanings as above] can be produced by a method mentioned in a document (such as *Journal of Organic Chemistry*, 1976, volume 41, no. 15, pages 2628 to 2633), by a method similar thereto or by combining those methods with a conventional method.

The compound of the present invention represented by the formula (I-10)

[wherein, the symbols have the same meanings as above] can be produced by a method mentioned in a document (such as WO 95/28389), by a method similar thereto or by combining those methods with a conventional method.

When (I) or (I-1), (I-2), (I-3), (I-4), (I-5), (I-6), (I-7), (I-8), (I-9) or (I-10) covered by the formula (I) have a protective group in X, Y, Z or W in the formula, conversion into an aimed compound is possible by removing the protective group. Removal of the protective group can be carried out by a method mentioned in a document (such as "Protective Groups in Organic Synthesis" by T. W. Green, second edition, John Wiley & Sons, 1991), by a method similar thereto or by combining those methods with a conventional method.

For example, when there is a methoxy group in X, Y, Z or W, boron tribromide is used whereby methoxy group can be converted into hydroxyl group.

Those compounds can be made into a pharmaceutically acceptable salt or ester by a conventional method and, reversely, conversion of salt or ester into a free compound also can be carried out by a conventional method.

The carbamoyl-substituted spiro derivative according to the present invention can be present as a pharmaceutically acceptable salt and can be produced by a conventional method using the compound represented by the above-mentioned formula (I), (I-1), (I-2), (I-3), (I-4), (I-5), (I-6), (I-7), (I-8), (I-9) or (I-10).

Examples of the acid-addition salt are a salt with a hydrogen halide such as hydrochloride, hydrofluoride, hydrobromide and hydroiodide; with an inorganic acid salt such as nitrate, perchlorate, sulfate, phosphate and carbonate; with a lower alkyl sulfonate such as methanesulfonate, trifluoromethanesulfonate and ethanesulfonate; with an arylsulfonate such as benzenesulfonate and p-toluenesulfonate; with an organic acid such as fumarate, succinate, citrate, tartrate, oxalate and maleate; and with an organic acid which is an amino acid such as glutamate and aspartate.

Examples of a base-addition salt are a salt with alkali metal such as sodium and potassium; a salt with alkali earth metal such as calcium and magnesium; an ammonium salt; and a salt with an organic base such as guanidine, triethylamine and dicyclohexylamine. The compound of the present invention may be also present as any hydrate or solvate of a free compound or a salt thereof.

The compound represented by the formula (I) or (I-1), (I-2), (I-3), (14), (I-5), (I-6), (I-7), (I-8), (I-9) or (I-10) covered by the formula (I) may be administered either orally or parenterally.

When the compound of the present invention is clinically used, it may be made into a pharmaceutical preparation by addition of a pharmaceutically acceptable additive thereto depending upon its dosage form. With regard to the additive at that time, various kinds of additives which have been commonly used in the field of pharmaceutical preparations may be used and examples thereof are gelatin, lactose, sucrose, titanium oxide, starch, crystalline cellulose, hydroxypropyl methylcellulose, carboxymethyl cellulose, corn starch, microcrystalline wax, white Vaseline, magnesium metasilicate aluminate, anhydrous calcium phosphate, citric acid, trisodium citrate, hydroxypropyl cellulose, sorbitol, sorbitan fatty acid ester, polysolvate, sucrose fatty acid ester, polyoxyethylene, hydrogenated castor oil, polyvinylpyrrolidone, magnesium stearate, light anhydrous silicic acid, talc, vegetable oil, benzyl alcohol, acacia, propylene glycol, polyalkylene glycol, cyclodextrin and hydroxypropyl cyclodextrin, etc.

Examples of the dosage form prepared as a mixture of such an additive are a solid preparation such as tablets, capsules, granules, diluted powder and suppositories and a liquid preparations such as syrup, elixir and injection and they may be prepared by a common method in the field of pharmaceutical preparations. In the liquid preparation, it may be in a form which is dissolved or suspended in water or other appropriate medium in actual use. Particularly in the case of injection, it may be dissolved or suspended, if necessary, in a physiological saline solution or a glucose solution or buffer and preservative may be further added thereto.

Such a preparation may contain the compound of the present invention in an amount of from 1.0 to 100% by weight and, preferably, from 1.0 to 60.0% by weight.

The compound of the present invention may be made into a pharmaceutical preparation by, for example, the following Preparation Examples.

Preparation Example 1

The compound of Example 1 which will be mentioned later (10 parts), 15 parts of heavy magnesium oxide and 75 parts of lactose are uniformly mixed to give diluted powder in a powdery or finely granular form of not larger than 350 μm. The diluted powder is placed in capsule containers to give a capsule preparation.

Preparation Example 2

The compound of Example 1 which will be mentioned later (45 parts), 15 parts of starch, 16 parts of lactose, 21 parts of crystalline cellulose, 3 parts of polyvinyl alcohol and 30 parts of distilled water are uniformly mixed, disintegrated, granulated, dried and sieved to give a granular preparation where diameter is within 1,410 to 177 μm.

Preparation Example 3

A granular preparation is prepared by the same method as in Preparation Example 2 and 3 parts of calcium stearate is added to 96 parts of the granular preparation followed by subjecting to a compression molding to give tablets of 10 mm diameter.

Preparation Example 4

To 90 parts of the granular preparation prepared by the method of Preparation Example 2 are added 10 parts of crystalline cellulose and 3 parts of calcium stearate followed by subjecting to a compression molding to give tablets of 8 mm diameter. To the tablets are added a mixed suspension of syrup, gelatin and precipitated calcium carbonate to give sugar-coated tablets.

Those preparations may also contain other therapeutically effective medicament as will be mentioned below.

The compound of the present invention can be used in combination with other medicament which is useful for the procedure (prevention or treatment) of metabolic disorder and eating disorder. Each component in such a combination can be administered in divided or single preparation(s) at different time or at the same time during the period for the procedure. The combination of the compound of the present invention with other medicament useful for the procedure of metabolic disorder or eating disorder principally includes a combination with any medicament which is useful for the procedure of metabolic disorder or eating disorder.

The compound of the present invention also can be used in combination with a medicament (hereinafter, it will be referred to as "co-drug") which is effective for hypertension, obesity-related hypertension, hypertension-related diseases, cardiac hypertrophy, left ventricular hypertrophy, metabolic diseases, obesity, obesity-related diseases, etc. In the prevention or treatment of the above-mentioned diseases, such a medicament and the compound of the present invention may be administered simultaneously, separately or successively. When the compound of the present invention is used together with one or more co-drug(s), it can be made into a pharmaceutical composition which is a single dosage form. However, in a combination treatment, a composition containing the compound of the present invention and the co-drug may be administered to the object to be administered simultaneously, separately or successively. In that case, the composition and the co-drug may be separately packed. They may be administered with a difference of time.

Dose of the co-drug may be in accordance with the clinically used dose and may be appropriately selected depending upon the patient to be administered, administering route, disease, combination, etc. There is no particular limitation for the dosage form of the co-drug but the compound of the present invention and the co-drug may be just combined at the stage of administration. Examples of the dosage form as such are 1) administration of a single pharmaceutical preparation prepared by making the compound of the present invention and the co-drug into the preparation simultaneously, 2) a simultaneous administration, by the same administration route, of two kinds of pharmaceutical preparations where the compound of the present invention and the co-drug are made into preparations separately, 3) administration, by the same administration route with difference of time, of two kinds of pharmaceutical preparations where the compound of the present invention and the co-drug are made into preparations separately, 4) a simultaneous administration, by different administration routes, of two kinds of pharmaceutical preparations where the compound of the present invention and the co-drug are made into preparations separately and 5) administration, by different administration routes with difference of time, of two kinds of pharmaceutical preparations where the compound of the present invention and the co-drug are made into preparations separately. Compounding ratio of the compound of the present invention to the co-drug may be appropriately selected depending upon, for example, a patient to be administered, administering route and disease.

Examples of the co-drug used in the present invention are remedy for diabetes, remedy for hyperlipemia, remedy for hypertension and remedy for obesity. With regard to the co-drug as such, two or more kinds thereof may be used jointly.

Examples of the above-mentioned remedy for diabetes are as follows.

1) PPAR (peroxisome proliferator-activated receptors) γ agonist such as glitazones (e.g., ciglitazone, darglitazone, englitazone, isaglitazone (MCC-555), pioglitazone, rosiglitazone, troglitazone, BRL 49653, CLX-0921 and 5-BTZD), GW-0207, LG-100641 and LY-300512, etc.

2) biguanides such as metformin, buformin and phenformin, etc.

3) protein tyrosine phosphatase-1B inhibitor, 4) sulfonylurea such as acetohexamide, chlorpropamide, diabinese, glibenclamide, glipizide, glyburide, glimepiride, gliclazide, glipentide, gliquidone, glisolamide, tolazamide and tolbutamide, etc.

5) meglitinides such as repaglinide and nateglinide, etc.

6) α-glucoside hydrolase inhibitors such as acarbose, adiposine, camiglibose, emiglitate, miglitol, voglibose, pradimicin-Q, salbostatin, CKD-711, MDL-25,673, MDL-73,945 and MOR 14, etc.

7) α-amylase inhibitors such as tendamistat, trestatin and A 13688, etc.

8) insulin secretion promoters such as linogliride and A-4166, etc.

9) fatty acid oxidation inhibitors such as clomoxir and etomoxir, etc.

10) A2 antagonists such as midaglizole, isaglidole, deriglidole, idazoxan, earoxan and fluparoxan, etc.

11) insulin or insulin-mimetics such as biota, LP-100, novarapid, insulin detemir, insulin lispro, insulin glargine, insulin zinc, Lys-Pro-insulin, GLP-1 (73-7) and GLP1 (7-36)-$NH_2$, etc.

12) non-thiadolidinediones such as JT-501 and farglitazar, etc.

13) PPARα/γ dual agonists such as CLX-0940, GW-1536, GW-1929, GW-2433, KRP-297, L-796449, LR-90 and SB 219994, etc.

14) other insulin sensitizers and

15) VPAC 2 receptor agonists.

Examples of the above-mentioned remedy for hyperlipemia are as follows.

1) bile acid absorption promoters such as cholesterylamine, colesvelem, colestipol, dialkylaminoalkyl derivative of crossed dextran, Colestid (registered trade mark), LoCholest (registered trade mark) and Questran (registered trade mark), etc.

2) HMG-CoA reductase inhibitors such as atorvastatin, itavastatin, fluvastatin, lovastatin, pravastatin, rivastatin, rosuvastatin, simvastatin and ZD-4522, etc.

3) HMG-CoA synthase inhibitors, 4) cholesterol absorption inhibitors such as sunatol ester, β-sitosterol, sterol glucoside and ezetimibe, etc.

5) ACAT (acyl-CoA cholesterol acyltransferase) inhibitors such as avasimibe, eflucimibe, KY-505 and SMP-709, etc.

6) CETP inhibitors such as JTT 705, torcetrapib, CP 532632, BAY-63-2149, SC-591 and SC-795, etc.

7) squalene synthetase inhibitors, 8) antioxidants such as probucol,

9) PPARα agonists such as beclofibrat, benzafibrate, ciprofibrate, clofibrate, etofibrate, fenofibrate, gemcabene, gemfibrozil, GW-7647, BM-170744, LY-518674 and fibric acid derivatives (e.g., Atromid (registered trade mark), Lopid (registered trade mark) and Tricor (registered trade mark)), etc.

10) FXR receptor antagonists such as GW4064 and SR-103912, etc.

11) LXR receptor agonists such as GW 3965, T 9013137 and XTCO-179628, etc.

12) lipoprotein synthesis inhibitors such as niacin, 13) renin-angiotensin system inhibitors, 14) PPARδ partial agonists, 15) bile acid re-absorption inhibitors such as BARA 1453, SC 435, PHA 384640, S-435 and AZD 7706, etc.

16) PPARδ agonists such as GW 501516 and GW 590735, etc.

17) triglyceride synthesis inhibitors,

18) MTTP (microsomic triglyceride transportation) inhibitors such as inplitapide, LAB 687 and CP 346086, etc.

19) transcription modification factors, 20) squalene expoxidase inhibitors,

21) LDL (low density lipoprotein) receptor derivatives, 22) platelet aggregation inhibitors, 23) 5-LO (5-lipoxigenase)/FLAP (5-lipoxiganase activated protein) inhibitors and 24) niacin receptor agonists.

Examples of the aforementioned remedy for hypertension are as follows.

1) diuretics such as those of a thiazide type (e.g., chlorothialidone, chlorothiazide, dichlorofenamide, hydrofluorothiazide indapamid and hydrochlorothiazide), a loop type (e.g., bumetanide, ethacrynic acid, furosemide and torsemide), a sodium type (e.g., amiloride and triamterene) and an aldosterone antagonist type (e.g., spironolactone and epirenone), 2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propranolol, sotalol, tertatolol, tilisolol and timolol, etc.

3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemidipine, lercanidipine, nicardipine, nifedipine, nilvadipine, nimodepine, nisoldipine, nitrendipine, manidipine, pranidipine and verapamil, etc.

4) angiotensin converting enzyme inhibitors such as benazepril, captopril, cilazapril, delapril, enalapril, fosinopril, imidapril, rosinopril, moexipril, quinapril, quinaprilat, ramipril, perindopril, perindropril, quanipril, spirapril, tenocapril, trandolapril and zofenopril, etc.

5) neutral endopeptidase inhibitors such as omapatrilat, cadoxatril, ecadotril, fosidotril, sampatrilat, AVE 7688 and ER 4030, etc.

6) endothelin antagonists such as tezosentan, A 308165 and YM 62899, etc.

7) vasodilators such as hydralazine, clonidine, minoxidil and nicotinyl alcohol, etc.

8) angiotensin II receptor antagonists such as candesartan, eprosartan, irbesartan, losartan, pratosartan, tasosartan, telmisartan, valsartan, EXP-3137, FI16828K and RNH 6207, etc.

9) α/β adrenaline blockers such as nipradilol, arotinolol and amosulalol, etc.

10) α1 blockers such as terazosin, urapidil, prazosin, bunazosin, trimazosin, doxazosin, naftopidil, indoramin, WHIP 164 and XEN 010, etc.

11) α2 agonists such as lofexidine, tiamenidine, moxonidine, rilmenidine and guanobenz and 12) aldosterone inhibitors.

Examples of the above-mentioned anti-obesity agent are as follows.

1) 5HT (serotonin) transporter inhibitors such as paroxetine, fluoxetine, fenfluramine, fluvoxamine, sertraline and imipramine, etc.

2) NE (nor-epinephrine) transporter inhibitors such as GW 320659, desipramine, talsupram and nomifensine, etc.

3) CB-1 (cannabinoid 1 receptor) antagonists/inverse agonists such as limonavant (Sanofi Synthelabo), SR-147778 (Sanofi Synthelabo), BAY-65-2520 (Bayer), SLV-319 (Solvay) and other compounds disclosed in U.S. Pat. No. 5,532,237, U.S. Pat. No. 4,973,587, U.S. Pat. No. 5,013,837, U.S. Pat. No. 5,081,122, U.S. Pat. No. 5,112,820, U.S. Pat. No. 5,292,736, U.S. Pat. No. 5,624,941, U.S. Pat. No. 6,028,084, WO 96/33159, WO 98/33765, WO 98/43636, WO 98/43635, WO 01/09120, WO 01/96330, WO 98/31227, WO 98/41519, WO 98/37061, WO 00/10967, WO 00/10968, WO 97/29079, WO 99/02499, WO 01/58869, WO 02/076949, WO 01/64632, WO 01/64633, WO 01/64634, WO 03/006007, WO 03/007887 and EP 658546.

4) ghrelin antagonists such as the compounds disclosed in WO 01/87355, WO 02/08250, etc., 5) histamine (H3) antagonists/inverse agonists such as thioperamide, 3-(1H-imidazol-4-yl)propyl N-(pentenyl)carbonate, clobenpropit, iodofenpropit, imoproxifen, GT 2395, A 331440, the compounds disclosed in WO 02/15905, O-[3-(1H-imidazo-4-yl)propanol] carbamate, piperazine-containing H3 receptor antagonists (Lazewska, D., et al., *Pharmazie*, 56:927-32 (2001)), benzophenone derivatives (Sasse, A., et al., *Arch. Pharm.* (Weinheim), 334:45-52 (2001)), substituted N-phenylcarbomates (Reidemeister, S., et al., *Pharmazie*, 55:83-6 (2000) and proxifeine derivatives (Sasse, A., et al., *J. Med. Chem.*, 43:3335-43 (2000)), 6) MCH-1R (melanin-concentrating hormone receptor 1) antagonists such as T-226296 (Takeda), SNP-7941 (Synaptic) and the compounds disclosed in WO 01/82925, WO 01/87834, WO 02/051809, WO 02/06245, WO 02/076929, WO 02/076947, WO 02/04433, WO 02/51809, WO 02/083134, WO 02/094799, WO 03/004027 and JP-A-2001/226,269, 7) MCH-2R (melanin-concentrating hormone receptor 2) agonists/antagonists, 8) NPY 1 (neuropeptide Y Y1) antagonists such as BIBP 3226, J-115814, BIBO 3304, YL-357897, CP-671906, GI-264879 and compounds disclosed in U.S. Pat. No. 6,001,836, WO 96/14307, WO 01/23387, WO 99/51600, WO 01/85690, WO 01/85098, WO 01/85173 and WO 01/89528, 9) NPY 5 (neuropeptide Y Y5) antagonists such as 152804, GW-569180A, GW-594884A, GW-587081X, GW-548118X, FR 235,208, FR 226928, FR 240662, FR 252384, 1229U91, GI-264879A, CGP 71683A, LY-377897, LY 366377, PD-160170, SR-120562A, SR0120819A, JCF-104, H409/22 and the compounds disclosed, in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,329,395, U.S. Pat. No. 6,340,683, U.S. Pat. No. 6,326,375, U.S. Pat. No. 6,329,395, U.S. Pat. No. 6,337,332, U.S. Pat. No. 6,335,345, EP 01010691, EP 01044970, WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/094789 and Norman, et al., *J. Med. Chem.*, 43:4288-4312 (2000).

10) leptine such as human recombinant leptine (PEG-OB, Hoffmann La Roche) and recombinant methionyl leptine (Amgen), etc.

11) leptine derivatives such as the compounds disclosed in U.S. Pat. No. 5,552,524, U.S. Pat. No. 5,552,523, U.S. Pat. No. 5,552,522, U.S. Pat. No. 5,521,283, WO 96/23513, WO 96/23514, WO 96/23515, WO 96/23516, WO 96/23517, WO 96/23518, WO 96/23519 and WO 96/23520, etc.

12) opioid antagonists such as nalmefene (Revex (registered trade mark), 3-methoxy-naltrexone, naloxone, naltrexone and the compounds disclosed in WO 00/21509, etc.

13) orexin antagonists such as SB-334867A and the compounds disclosed in WO 01/96302, WO 01/68609, WO 02/51232, WO 02/51838 and WO 03/023561, etc.

14) BRS 3 (bombesin receptor subtype 3) agonists,

15) CCK-A (cholecystokinin A) agonists such as AR-R 15849, GI-181771, JMV-180, A-71378, A-71623, SR-146131 and the compounds disclosed in U.S. Pat. No. 5,739,106, etc.

16) CNTF (ciliary neurotrophic factors) such as GI-181711 (Glaxo-Smith Kline), SR 146131 (Sanofi Synthelabo), butabindide, PD 170,292 and PD 149,164 (Pfizer), etc.

17) CNTF derivatives such as axokine (Regeneron) and compounds disclosed in WO 94/09134, WO 98/22128 and WO 99/43813, etc.

18) GHS (growth hormone secretion promoter receptor) agonists such as NN 703, hexarelin, MK-0677, SM-130686, CP424,391, L-692,429, L-163,255 and the compounds disclosed in U.S. Pat. No. 6,358,951, US-PTO Serial Nos. 2002/049196 and 2002/022637, WO 01/56592 and WO 02/32888, etc.

19) 5HT2c (serotonin receptor 2c) agonists such as BVT 933, DPCA 37215, IK 264, PNU 22394, WAY 161503, R-1065, YM 348 and the compounds disclosed in U.S. Pat. No. 3,914,250, WO 02/36596, WO 02/48124, WO 02/10169, WO 01/66548, WO 02/44152, WO 02/51844, WO 02/40456 and WO 02/40457, etc.

20) Mc3r (melanocortin 3 receptor) agonists,

21) Mc4r (melanocortin 4 receptor) agonists such as CHIR 86036 (Chiron), ME-10142 and ME-10145 (Melacure) and the compounds disclosed in WO 99/64002, WO 00/74679, WO 01/991752, WO 01/74844, WO 01/70708, WO 01/70337, WO 01/91752, WO 02/059095, WO 02/059107, WO 02/059108, WO 02/059117, WO 02/12166, WO 01/11715, WO 02/12178, WO 02/15909, WO 02/068387, WO 02/068388, WO 02/067869, WO 03/007949 and WO 03/009847, etc.

22) monoamine reuptake inhibitors such as sibutramine (Meridia (registered trade mark)/Reductil (registered trade mark)) and salts thereof and the compounds disclosed in U.S. Pat. No. 4,746,680, U.S. Pat. No. 4,806,570, U.S. Pat. No. 5,436,272, US-PTO Serial No. 2002/0006964, WO 01/27068 and WO 01/62341, etc.

23) serotonin reuptake inhibitors such as dexfenfluramine, fluoxetine and the compounds disclosed in U.S. Pat. No. 6,365,633, WO 01/27060 and WO 01/162341, etc.

24) GLP 1 (glucagon-like peptide 1) agonists, 25) topiramate (Topamax (registered trade mark)), 26) phytopharm compound 57 (phytopharm) (such as CP 644,673), 27) ACC 2 (acetyl-CoA carboxylase 2) inhibitors, 28) β3 (adrenaline receptor 3) agonists such as AD 9677/TAK 677 (Dainippon Pharmaceutical/Takeda), CL-316,243, SB 418790, BRL-37344, L-796568, BMS-196085, BRL-35135A, CGP 12177A, BTA-243, W 427353, Trecadrine, Zeneca D 7114, SR 59119A and the compounds disclosed in U.S. Pat. No. 5,705,515, U.S. Pat. No. 5,451,677, WO 01/74782 and WO 02/32897, etc.

29) DGAT 1 (diacylglycerol acyltransferase 1) inhibitors,

30) DGAT 2 (diacylglycerol acyltransferase 2) inhibitors,

31) FAS (fatty acid synthase) inhibitors such as Cerulenin and C75, etc.

32) PDE (phosphodiesterase) inhibitors such as theophylline, pentoxifylline, zaprinast, sildenafil, aminone, milrinone, cilostamide, rolipram and cilomilast, etc.

33) thyroid hormone β agonists such as KB-2611 (KaroBioBMS) and the compounds disclosed in WO 02/15845 and JP-A-2000/256,190, etc.

34) UCP (uncoupling protein)-1, 2 or 3 activators such as phytanic acid, 4-[(E)-2-(5,6,7,8-tetrahydro-5,5,8,8-tetramethyl-2-naphthalenyl)-1-propenyl]benzoic acid (TTNPB), retinoic acid and the compounds disclosed in WO 99/00123, etc.

35) acylestrogens such as oleoylestron (del Mar-Grasa, M., et al., *Obesity Research*, 9:202-9 (2001)), 36) glucocorticoid antagonists, 37) 11-β HSD1 (11-β hydroxysteroid dehydrogenase type 1) inhibitors such as BVT 3498, BVT 2733 and the compounds disclosed in WO 01/90091, WO 01/90090 and WO 02/90092, etc.

38) SCD 1 (stearoyl-CoA desaturase 1) inhibitors,

39) DP-IV (dipeptidyl peptidase IV) inhibitors such as isoleucine thiazolidide, valine pyrrolidide, NVP-DPP 728, AF 237, P93/01, TSL 225, TMC-2A/2B/2C, FE 999011, P 9310/K 364, VIP 0177, SDZ 274-444 and the compounds disclosed in WO 03/004498, WO 03/004496, EP 1,258,476, WO 02/083128, WO 02/062764, WO 03/000250, WO 03/002530, WO 03/002531, WO 03/002553, WO 03/002593, WO 03/000180 and WO 03/000181, etc.

40) lipase inhibitors such as tetrahydrolipstatin (orlistat; Xenical (registered trade mark)), Triton WR 1339, RHC 80267, lipstatin, tea saponin, diethylumbelliferyl phosphate, FL-386, WAY-121898, Bay-N-3176, valilactone, esteracin, ebelactone A, ebelactone B, RHC 80267 and the compounds disclosed in WO 01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438 and U.S. Pat. No. 4,242,453, etc.

41) fatty acid transporter inhibitors, 42) dicarboxylate transporter inhibitors, 43) glucose transporter inhibitors, 44) phosphate transporter inhibitors, 45) melanocortin agonists such as melanotan II and the compounds disclosed in WO 99/64002 and WO 00/746799, etc.

46) melanin concentrating hormone antagonists, 47) galanin antagonists,

48) CCK agonists, 49) corticotropin-releasing hormones and

50) PDE 3 (phosphodiesterase 3B) agonists.

The compound of the present invention can be combined with one or more of the above-mentioned co-drugs. Joint use of the compound of the present invention with one or more medicament(s) selected from the group consisting of remedy for diabetes and remedy for hyperlipemia is useful for prevention or treatment of metabolic diseases. Particularly when remedy for diabetes or remedy for hyperlipemia is further combined with the compound of the present invention in addition to remedy for hypertension and remedy for obesity, a preventive or treating effect for metabolic diseases is synergically achieved.

When the compound of the present invention is used in a clinical field, its dose and administering frequency vary depending upon sex, age, body weight and degree of symptom of a patient, type and range of the aimed procedure effect, etc. Usually, in the case of oral administration, 0.01 to 100 mg/kg or, preferably, 0.03 to 1 mg/kg per day for an adult is administered by dividing into one to several times a day. In the case of parenteral administration, 0.001 to 10 mg/kg or, preferably, 0.001 to 0.1 mg/kg is administered by dividing into one to several times a day.

Usual doctors of internal medicine, veterinarians or clinical doctors are easily able to decide an effective dose which is necessary for inhibiting, suppressing or stopping the progress of the disease.

EXAMPLES

Now the present invention will be more specifically described by referring to Examples as follows although the present invention is not limited at all by those Examples.

In a thin-layer chromatography in the Examples, Silicagel 60 $F_{245}$ (Merck) was used as a plate and UV detector was used as a detecting means. As to silica gel for the column, Wako-gel™ C-300 (Wako Pure Chemical), KP-Sil (Biotage) or KP-NH (Biotage) was used; as to silica gel for a reverse-phase column, YMC-GEL™ ProC18 (Yamamura Kagaku Kenkyusho) was used; and, as to a reversed phase HPLC column, YMC-CombiPrep ProC18 (YMC) was used. Mass spectrum is measured by an electrospray ionization method (ESI) using Quattro II (manufactured by Micromass).

With regard to an NMR spectrum, when measurement is carried out in a heavy dimethyl sulfoxide solution, dimethyl sulfoxide is used as an internal standard, measurement is conducted using a spectrophotometer of a type of Gemini-200 (200 MHz; Varian), Gemini-300 (300 MHz; Varian), Mercury 400 (400 MHz; Varian) or Inova 400 (400 MHz; Varian) and the all δ values are shown in ppm.

Meanings of the abbreviations in the following Examples are as shown below.
i-Bu: isobutyl group
n-Bu: n-butyl group
t-Bu: tert-butyl group
Me: methyl group
Et: ethyl group
Ph: phenyl group
i-Pr: isopropyl group
n-Pr: n-propyl group
CDCl$_3$: heavy chloroform
CD$_3$OD: heavy methanol
DMSO-d$_6$: heavy dimethyl sulfoxide As hereunder, meanings of the abbreviations in the nuclear magnetic resonance spectrum are shown.
s: singlet
d: doublet
dd: double doublet
t: triplet
m: multiplet
br: broad
q: quartet
quint: quintet
J: coupling constant
Hz: Herz Example 1 trans-5'-(2-Fluoroethoxy)-3'-oxo-N-methyl-N-(2-piperidin-1-ylethyl)-spiro[cyclohexane-1,1'-(3'H)-iso-benzofuran]-4-carboxamide hydrochloride

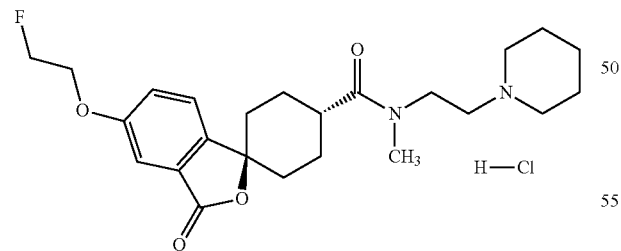

To a solution of trans-5-(2-fluoroethoxy)-3-oxo-3H-spiro [2-benzofuran-1,1'-cyclohexane]-4'-carboxylic acid (70 mg) produced in Reference Example 1-1 in chloroform (2.0 mL) were added triethylamine (0.063 mL), N-methyl-N-(piperidinoethyl)amine (0.032 mL), a 2N solution of 2-chloro-1,3-dimethylimidazolinium chloride in dichloromethane (0.15 mL) and, after that, the mixture was stirred at 0° C. for 30 minutes. A saturated aqueous solution of sodium hydrogen carbonate was added to the reaction solution followed by extracting with ethyl acetate. The organic layer was washed with a saturated saline solution, dried over sodium sulfate, filtered, concentrated in vacuo and purified by a reversed phase HPLC (0.1% TFA acetonitrile:H$_2$O=from 5% to 50%, gradient) to give a colorless oily product (67 mg, 68%). The resulting residue (60 mg) was dissolved in ethyl acetate (2.0 mL) and a 4N solution of hydrogen chloride in ethyl acetate (0.1 mL) was added thereto followed by concentrating in vacuo. Ethyl acetate was added thereto to suspend and the solid separated out therefrom was filtered to give the title compound (45 mg, 69%) as a colorless solid.

$^1$HNMR (400 MHz, DMSO-d$_6$, δ): 1.30-2.04 (14H, m), 2.82-3.90 (9H, m), 2.86 (3H×¼, s), 3.09 (3H×¾), 7.32-7.66 (3H, m), 9.35 (1H×¾, brs), 10.30 (1H×¼, brs); mass spectrum (ESI): 433.3 (M+H)

The compounds of Examples 2 to 22 can be produced using the corresponding carboxylic acid and amine as materials by the same method as in Example 1, by a method similar thereto or by combining such methods with a conventional method.

Example 2 trans-3'-oxo-N-methyl-N-(2-piperidin-1-ylethyl)-spiro[cyclohexane-1,1'-(3'H)-isobenzofuran]-4-carboxamide hydrochloride

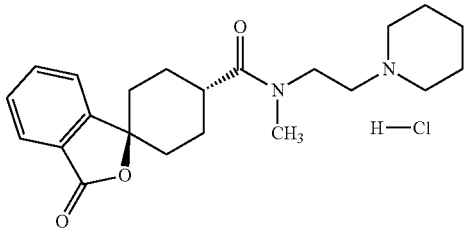

The title compound was prepared by the method according to Example 1 using trans-3-oxo-3H-spiro[2-benzofuran-1,1'-cyclohexane]-4'-carboxylic acid produced in Reference Example 1-2 and N-methyl-N-(piperidinoethyl)amine as materials.

$^1$HNMR (400 MHz, DMSO-d$_6$, δ): 1.30-2.10 (14H, m), 2.82-3.54 (7H, m), 2.86 (3H×¼, s), 3.10 (3H×¾, s), 3.71 (2H×¾, d, J=6.8 Hz), 3.82-3.92 (2H×¼, m), 7.59-7.87 (4H, m), 10.18 (1H×¾, brs), 11.07 (1H×¼, brs); mass spectrum (ESI): 371.3 (M+H)

Example 3 trans-3'-oxo-N-methyl-N-(2-pyrrolidin-1-ylethyl)-spiro[cyclohexane-1,1'-(3'H)-isobenzofuran]-4-carboxamide hydrochloride

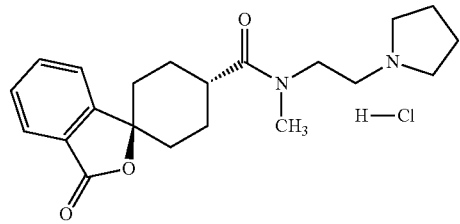

The title compound was prepared by the method according to Example 1 using trans-3-oxo-3H-spiro[2-benzofuran-1,1'- cyclohexane]-4'-carboxylic acid produced in Reference Example 1-2 and N-methyl-N-(pyrrolidinoethyl)amine as materials.

¹HNMR (400 MHz, DMSO-d₆, δ): 1.80-2.10 (12H, m), 2.87 (3H×¼, s), 2.94-3.42 (5H, m), 3.10 (3H×¾, s), 3.47-3.61 (1H, m), 3.67 (2H×¾, d, J=6.6 Hz), 3.76-3.84 (2H×¼, m), 7.59-7.87 (4H, m), 10.62 (1H×¾, brs), 11.38 (1H×¼, brs); mass spectrum (ESI): 357.2 (M+H)

Example 4 trans-3'-oxo-N-(2-piperidin-1-ylethyl)-spiro[cyclohexane-1,1'-(3'H)-isobenzofuran]-4-carboxamide

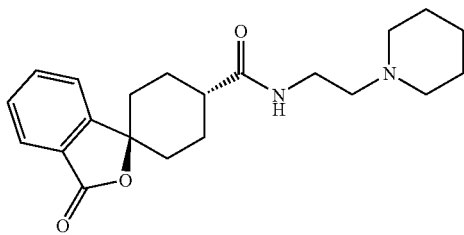

The title compound was prepared by the method according to Example 1 using trans-3-oxo-3H-spiro[2-benzofuran-1,1'-cyclohexane]-4'-carboxylic acid produced in Reference Example 1-2 and 1-(2-aminoethyl)piperidine as materials.

¹HNMR (400 MHz, CDCl₃, δ): 1.40-1.50 (2H, m), 1.53-1.62 (4H, m), 1.75-1.84 (2H, m), 2.04-2.18 (4H, m), 2.21-2.32 (2H, m), 2.33-2.44 (4H, m), 2.47 (2H, t, J=5.9 Hz), 2.51-2.60 (1H, m), 3.34-3.41 (2H, m), 6.37 (1H, brs), 7.46-7.53 (1H, m), 7.56-7.66 (2H, m), 7.86 (1H, dd, J=7.7 Hz); mass spectrum (ESI): 357.4 (M+H)

Example 5 trans-3'-oxo-N-(2-pyrrolidin-1-ylethyl)-spiro[cyclohexane-1,1'-(3'H)-isobenzofuran]-4-carboxamide

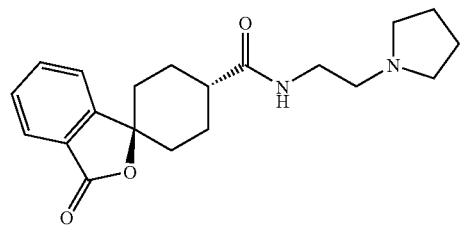

The title compound was prepared by the method according to Example 1 using trans-3-oxo-3H-spiro[2-benzofuran-1,1'-cyclohexane]-4'-carboxylic acid produced in Reference Example 1-2 and 1-(2-aminoethyl)pyrrolidine as materials.

¹HNMR (400 MHz, CDCl₃, δ): 1.75-1.86 (6H, m), 2.05-2.17 (4H, m), 2.22-2.34 (2H, m), 2.52-2.63 (5H, m), 2.64-2.71 (2H, m), 3.38-3.48 (2H, m), 6.42 (1H, brs), 7.48-7.56 (1H, m), 7.58-7.68 (2H, m), 7.88 (1H, d, J=7.6 Hz); mass spectrum (ESI): 343.3 (M+H)

Example 6 trans-4-ethylpiperazinyl-(2S)-methyl-3'-oxo-spiro[cyclohexane-1,1'-(3'H)-isobenzofuran]-4-carboxamide

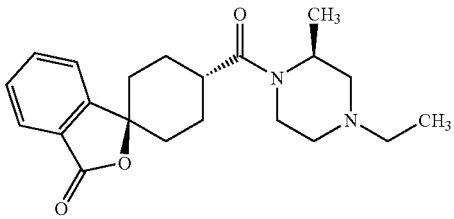

The title compound was prepared by the method according to Example 1 using trans-3-oxo-3H-spiro[2-benzofuran-1,1'-cyclohexane]-4'-carboxylic acid produced in Reference Example 1-2 and 1-ethyl-(3S)-methylpiperazine as materials.

¹HNMR (400 MHz, CDCl₃, δ): 1.04-1.10 (3H, m), 1.20-1.46 (3H, m), 1.76-2.48 (12H, m), 2.72-2.82 (1H, m), 2.84-2.93 (2H, m), 2.94-3.04 (1H×½, m), 3.38-3.52 (1H×½, m), 3.58-3.74 (1H×½, m), 4.02-4.15 (1H×½, m), 4.35-4.50 (1H×1½, m), 4.72-4.88 (1H×½, m), 7.46-7.54 (1H, m), 7.60-7.70 (2H, m), 7.86 (1H, d, J=7.7 Hz); mass spectrum (ESI): 357.3 (M+H)

Example 7 trans-4-(hexahydropyrrolo[1,2-a]pyrazinyl)-3'-oxo-spiro[cyclohexane-1,1'-(3'H)-isobenzofuran]-4-carboxamide

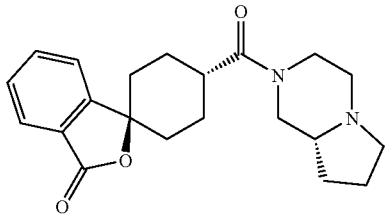

The title compound was prepared by the method according to Example 1 using trans-3-oxo-3H-spiro[2-benzofuran-1,1'-cyclohexane]-4'-carboxylic acid produced in Reference Example 1-2 and (R)-octahydropyrrolo[1,2-a]pyrazine as materials.

¹HNMR (400 MHz, CDCl₃, δ): 1.22-2.36 (15H, m), 2.37-2.48 (1H×½, m), 2.74-2.85 (1H×½, m), 2.88-3.34 (4H, m), 3.88 (1H×½, d, J=13.2 Hz), 3.99 (1H×½, d, J=12.5 Hz), 4.65 (1H×½, d, J=13.2 Hz), 4.78 (1H×½, d, J=12.5 Hz), 7.46-7.55 (1H, m), 7.58-7.68 (2H, m), 7.82-7.90 (1H, m); mass spectrum (ESI): 355.3 (M+H)

Example 8 trans-3'-oxo-N-methyl-N-(1-cyclopentylpyrrolidin-3-yl)-spiro[cyclohexane-1,1'-(3'H)-isobenzofuran]-4-carboxamide

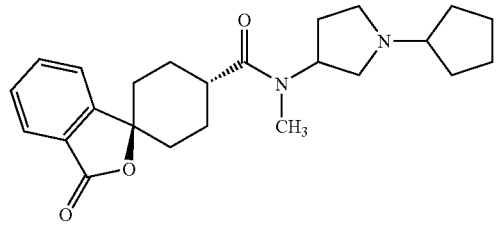

The title compound was prepared by the method according to Example 1 using trans-3-oxo-3H-spiro[2-benzofuran-1,1'-cyclohexane]-4'-carboxylic acid produced in Reference Example 1-2 and N-(1-cyclopentyl-3-pyrrolidinyl)-N-methylamine as materials.

$^1$HNMR (400 MHz, CDCl$_3$, δ): 1.36-3.04 (24H, m), 2.92 (3H×½, s), 3.08 (3H×½, s), 4.52-4.64 (1H×½, m), 5.20-5.32 (1H×½, m), 7.45-7.53 (1H, m), 7.58-7.70 (2H, m), 7.86 (1H, d, J=7.7 Hz); mass spectrum (ESI): 397.2 (M+H)

Example 9 trans-5'-methoxy-3'-oxo-N-methyl-N-(2-piperidin-1-ylethyl)-spiro[cyclohexane-1,1'-(3'H)-isobenzofuran]-4-carboxamide hydrochloride

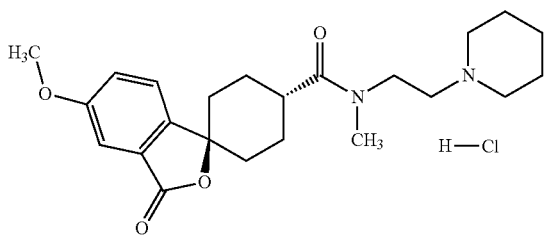

The title compound was prepared by the method according to Example 1 using trans-5-methoxy-3-oxo-3H-spiro[2-benzofuran-1,1'-cyclohexane]-4'-carboxylic acid produced in Reference Example 1-3 and N-methyl-N-(piperidinoethyl)amine as materials.

$^1$HNMR (400 MHz, DMSO-d$_6$, δ): 1.30-2.06 (14H, m), 2.82-3.25 (5H, m), 2.86 (3H×¼, s), 3.10 (3H×¾, s), 3.41-3.54 (2H, m), 3.65-3.90 (2H, m), 3.84 (3H, s), 7.27-7.39 (2H, m), 7.53 (1H×¾, d, J=8.4 Hz), 7.61 (1H×¼, d, J=8.6 Hz), 9.94 (1H×¾, brs), 10.84 (1H×¼, brs); mass spectrum (ESI): 401.3 (M+H)

Example 10 trans-5'-fluoro-3'-oxo-N-methyl-N-(2-piperidin-1-ylethyl)-spiro[cyclohexane-1,1'-(3'H)-isobenzofuran]-4-carboxamide hydrochloride

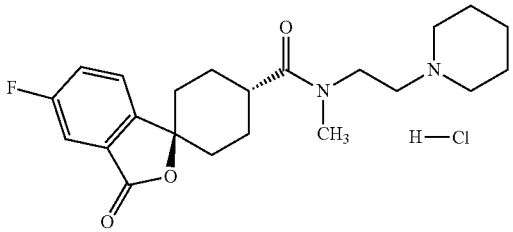

The title compound was prepared by the method according to Example 1 using trans-5-fluoro-3-oxo-3H-spiro[2-benzofuran-1,1'-cyclohexane]-4'-carboxylic acid produced in Reference Example 1-4 and N-methyl-N-(piperidinoethyl)amine as materials.

$^1$HNMR (400 MHz, DMSO-d$_6$, δ): 1.30-2.12 (14H, m), 2.82-3.28 (5H, m), 2.86 (3H×⅕, s), 3.09 (3H×⅘, s), 3.42-3.54 (2H, m), 3.69 (2H×⅘, d, J=6.8 Hz), 3.78-3.88 (2H×⅕, m), 7.62-7.78 (3H, m), 9.78 (1H×⅘, brs), 10.68 (1H×⅕, brs); mass spectrum (ESI): 389.2 (M+H)

Example 11 trans-5'-fluoro-2-pyrrolidin-1-ylmethylpyrrolidinyl-3'-oxo-spiro[cyclohexane-1,1'-(3'H)-isobenzofuran]-4-carboxamide hydrochloride

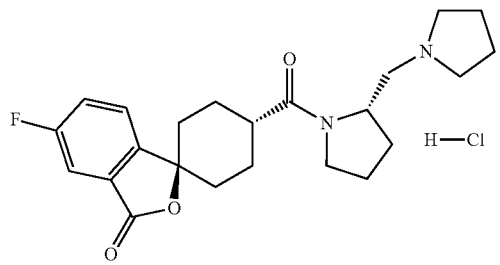

The title compound was prepared by the method according to Example 1 using trans-5-fluoro-3-oxo-3H-spiro[2-benzofuran-1,1'-cyclohexane]-4'-carboxylic acid produced in Reference Example 14 and (S)-(+)-1-(2-pyrrolidinylmethyl)pyrrolidine as materials.

$^1$HNMR (400 MHz, DMSO-d$_6$, δ): 1.80-2.14 (16H, m), 2.78-2.94 (1H, m), 3.00-3.26 (4H, m), 3.48-3.70 (4H, m), 4.22-4.44 (1H, m), 7.62-7.80 (3H, m), 10.30 (1H, brs); mass spectrum (ESI): 401.2 (M+H)

Example 12 trans-7'-methoxy-3'-oxo-N-methyl-N-(2-piperidin-1-ylethyl)-spiro[cyclohexane-1,1'-(3'H)-isobenzofuran]-4-carboxamide hydrochloride

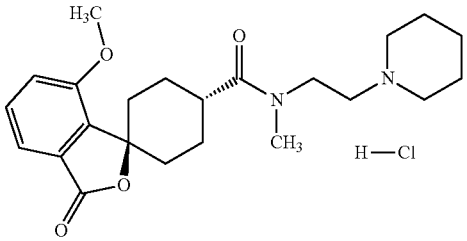

The title compound was prepared by the method according to Example 1 using trans-7-methoxy-3-oxo-3H-spiro[2-benzofuran-1,1'-cyclohexane]-4'-carboxylic acid produced in Reference Example 2-1 and N-methyl-N-(piperidinoethyl)amine as materials.

$^1$HNMR (400 MHz, DMSO-d$_6$, δ): 1.28-1.96 (14H, m), 2.62-2.78 (2H, m), 2.82-2.96 (2H, m), 3.05 (3H, s), 3.14-3.26 (1H, m), 3.42-3.54 (2H, m), 3.65-3.80 (2H, m), 3.85 (3H, s), 7.30-7.40 (2H, m), 7.53 (1H, t, J=7.8 Hz), 9.70 (1H, brs); mass spectrum (ESI): 401.3 (M+H)

Example 13 trans-7'-methoxy-3'-oxo-N-methyl-N-(2-pyrrolidin-1-ylethyl)-spiro[cyclohexane-1,1'-(3'H-isobenzofuran]-4-carboxamide hydrochloride

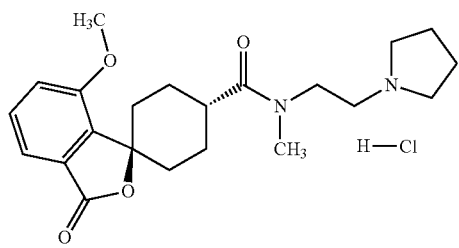

The title compound was prepared by the method according to Example 1 using trans-7-methoxy-3-oxo-3H-spiro[2-benzofuran-1,1'-cyclohexane]-4'-carboxylic acid produced in Reference Example 2-1 and N-methyl-N-(piperazinoethyl) amine as materials.

$^1$HNMR (400 MHz, DMSO-$d_6$, δ): 1.35-2.06 (12H, m), 2.64-3.38 (5H, m), 2.85 (3H×⅕, s), 3.06 (3H×⅘, s), 3.46-3.78 (4H, m), 3.85 (3H, s), 7.32-7.39 (2H, m), 7.50-7.56 (1H, m), 10.54 (1H×⅘, brs), 11.21 (1H×⅕, brs); mass spectrum (ESI): 387.2 (M+H)

Example 14 trans-6'-methoxy-3'-oxo-N-methyl-N-(2-pyrrolidin-1-ylethyl)-spiro[cyclohexane-1,1'-(3'H)-isobenzofuran]-4-carboxamide

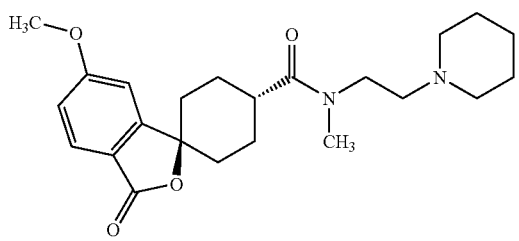

The title compound was prepared by the method according to Example 1 using trans-6-methoxy-3-oxo-3H-spiro[2-benzofuran-1,1'-cyclohexane]-4'-carboxylic acid produced in Reference Example 2-2 and N-methyl-N-(piperazinoethyl) amine as materials.

$^1$HNMR (400 MHz, DMSO-$d_6$, δ): 1.40-2.16 (12H, m), 2.30-2.56 (8H, m), 2.90-3.00 (1H, m), 2.98 (3H×½, s), 3.12 (3H×½, s), 3.46 (2H×½, d, J=6.9 Hz), 3.56 (2H×½, d, J=6.9 Hz), 3.90 (3H×½, s), 3.91 (3H×½, s), 6.98-7.09 (2H, m), 7.77 (1H, d, J=8.8 Hz); mass spectrum (ESI): 401.3 (M+H)

Example 15 trans-N-methyl-1'-(methylsulfonyl)-N-(2-piperidin-1-ylethyl)-1',2'-dihydrospiro[cyclohexane-1,3'-indole]-4-carboxamide

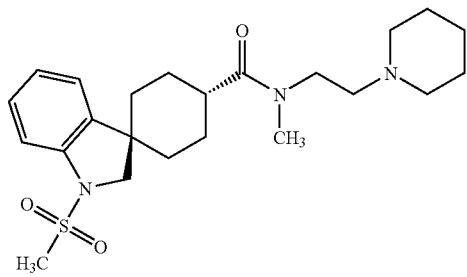

The title compound was prepared by the method according to Example 1 using trans-1'-(methylsulfonyl)-1',2'-dihydrospiro[cyclohexane-1,3'-indole]-4-carboxylic acid and N-methyl-N-(piperidinoethyl)amine as materials.

$^1$HNMR (400 MHz, CDCl$_3$, δ): 1.38-1.77 (8H, m), 2.00-2.18 (4H, m), 2.38-2.50 (6H, m), 2.68-2.80 (1H, m), 2.88 (3H, s), 2.96 (3H×½, s), 3.08 (3H×½, s), 3.40-3.56 (2H×½, m), 3.66-3.72 (2H×½, m), 7.00-7.08 (1H, m), 7.16-7.24 (1H, m), 7.35-7.40 (1H, m), 7.52-7.60 (1H, m); mass spectrum (ESI): 434.4 (M+H)

Example 16 trans-N,2'-dimethyl-3'-oxo-N-(2-piperidin-1-ylethyl)-2',3'-dihydrospiro[cyclohexane-1,1'-isoindole]-4-carboxamide

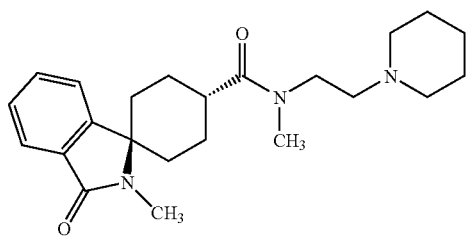

The title compound was prepared by the method according to Example 1 using trans-2'-methyl-3'-oxo-2',3'-dihydrospiro[cyclohexane-1,1'-isoindole]-4-carboxylic acid produced in Reference Example 4 and N-methyl-N-(piperidinoethyl)amine as materials.

$^1$HNMR (400 MHz, CDCl$_3$, δ): 1.36-1.88 (8H, m), 2.01-2.23 (4H, m), 2.30-2.59 (8H, m), 2.94-3.07 (1H, m), 2.98 (3H×½, s), 3.13 (3H×½, s), 3.20 (3H×½, s), 3.23 (3H×½, s), 3.43-3.61 (2H, m), 7.40-7.55 (2H, m), 7.56-7.64 (1H, m), 7.86 (1H, d, J=7.1 Hz); mass spectrum (ESI): 384.4 (M+H)

Example 17 cis-N,2'-dimethyl-3'-oxo-N-(2-piperidin-1-ylethyl)-2',3'-dihydrospiro[cyclohexane-1,1'-isoindole]-4-carboxamide

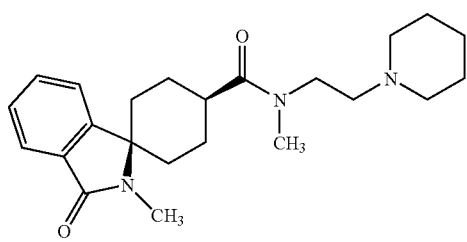

The title compound was prepared by the method according to Example 1 using cis-2'-methyl-3'-oxo-2',3'-dihydrospiro[cyclohexane-1,1'-isoindole]-4-carboxylic acid produced in Reference Example 4 and N-methyl-N-(piperidinoethyl)amine as materials.

$^1$HNMR (400 MHz, CDCl$_3$, δ): 1.36-1.81 (8H, m), 1.82-1.97 (2H, m), 1.97-2.13 (2H, m), 2.22-2.59 (8H, m), 2.65-2.83 (1H, m), 3.01 (3×½H, s), 3.05 (3H, s), 3.16 (3H×½, s), 3.50 (2H×½, t, J=7.1 Hz), 3.57 (2H×½, t, J=7.2 Hz), 7.43-7.59 (2H, m), 7.86-7.91 (1H, m), 7.99 (1H×½, d, J=7.6 Hz), 8.03 (1H×½, d, J=7.6 Hz); mass spectrum (ESI): 384.4 (M+H)

Example 18 trans-5'-methoxy-3'-oxo-N-methyl-N-(2-pyrrolidin-1-ylethyl)-spiro[cyclohexane-1,1'-(3'H)-isobenzofuran]-4-carboxamide

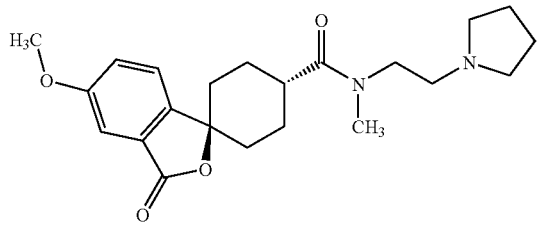

The title compound was prepared by the method according to Example 1 using trans-5-methoxy-3-oxo-3H-spiro[2-benzofuran-1,1'-cyclohexane]-4'-carboxylic acid produced in Reference Example 1-3 and N-methyl-N-(pyrrolidinoethyl)amine as materials.

$^1$HNMR (400 MHz, CDCl$_3$, δ): 1.74-1.92 (6H, m), 1.98-2.12 (4H, m), 2.16-2.26 (2H, m), 2.54-2.74 (6H, m), 2.86-2.95 (1H, m), 2.99 (3H×½, s), 3.13 (3H×½, s), 3.46-3.62 (2H, m), 3.86 (3H, s), 7.16-7.22 (1H, m), 7.30-7.35 (1H, m), 7.57 (1H×½, d, J=8.7 Hz), 7.62 (1H×½, d, J=8.7 Hz); mass spectrum (ESI): 387.3 (M+H)

Example 19 trans-5'-fluoro-3'-oxo-N-methyl-N-(2-pyrrolidin-1-ylethyl)-spiro[cyclohexane-1,1'-(3'H-isobenzofuran]-4-carboxamide

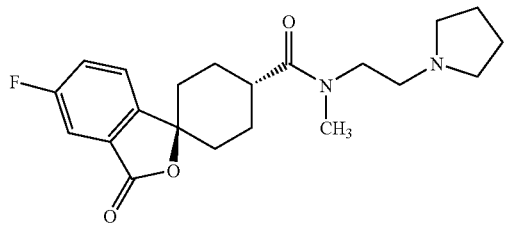

The title compound was prepared by the method according to Example 1 using trans-5-fluoro-3-oxo-3H-spiro[2-benzofuran-1,1'-cyclohexane]-4'-carboxylic acid produced in Reference Example 1-4 and N-methyl-N-(pyrrolidinoethyl)amine as materials.

$^1$HNMR (400 MHz, CDCl$_3$, δ): 1.72-1.92 (6H, m), 1.92-2.15 (4H, m), 2.20-2.38 (2H, m), 2.47-2.74 (6H, m), 2.88-3.00 (1H, m), 2.99 (3H×½, s), 3.12 (3H×½, s), 3.43-3.62 (2H, m), 7.31-7.40 (1H, m), 7.50-7.56 (1H, m), 7.61-7.72 (1H, m); mass spectrum (ESI): 375.4 (M+H)

Example 20 trans-5'-hydroxy-3'-oxo-N-methyl-N-(2-pyrrolidin-1-ylethyl)-spiro[cyclohexane-1,1'-(3'H)-isobenzofuran]-4-carboxamide

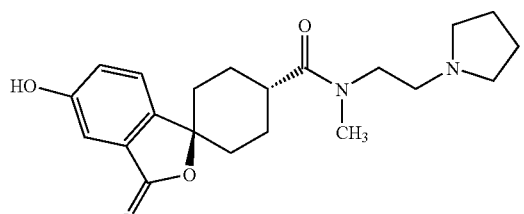

The title compound was prepared by the method according to Example 1 using trans-5-hydroxy-3-oxo-3H-spiro[2-benzofuran-1,1'-cyclohexane]-4'-carboxylic acid produced in Reference Example 3 and N-methyl-N-(pyrrolidinoethyl)amine as materials.

$^1$HNMR (400 MHz, CDCl$_3$, δ): 1.75-2.20 (12H, m), 2.57-2.78 (6H, m), 2.80-2.93 (1H, m), 3.04 (3H×½, s), 3.15 (3H×½, s), 3.54 (2H×½, t, J=7.3 Hz), 3.61 (2H×½, t, J=7.1 Hz), 7.26-7.40 (2H, m), 7.62 (1H×½, d, J=7.8 Hz), 7.70 (1H×½, d, J=8.3 Hz); mass spectrum (ESI): 373.3 (M+H)

Example 21

1'-(4-Piperidin-1-ylbutanoyl)-3H-spiro[2-benzofuran-1,4'-piperidine]-3-one

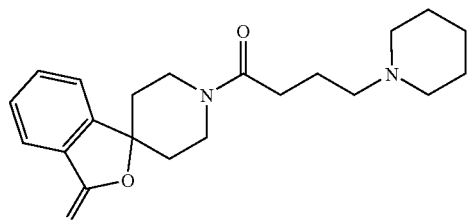

The title compound was prepared by the method according to Example 1 using 3H-spiro[2-benzofuran-1,4'-piperidine]-3-one hydrochloride monohydrate and 4-piperidine-1-butanoic acid as materials.

$^1$HNMR (400 MHz, CDCl3, δ): 1.34-1.50 (2H, m), 1.51-1.66 (4H, m), 1.69-1.82 (2H, m), 1.83-1.96 (2H, m), 1.98-2.14 (2H, m), 2.29-2.54 (8H, m), 3.01-3.16 (1H, m), 3.52-3.66 (1H, m), 3.91-4.07 (1H, m), 4.66-4.85 (1H, m), 7.37 (1H, d, J=7.3 Hz), 7.53-7.60 (1H, m), 7.67-7.74 (1H, m), 7.91 (1H, d, J=7.3 Hz); mass spectrum (ESI): 357.3 (M+H)

Example 22 trans-5'-Methoxy-3'-oxo-N,4-dimethyl-N-(2-pyrrolidin-1-ylethyl)-spiro[cyclohexane-1,1'-(3'H)-isobenzofuran]-4-carboxamide

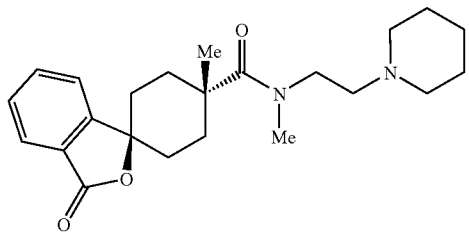

The title compound was prepared by the method according to Example 1 using trans-5-methoxy-3-oxo-3H-spiro[2-benzofuran-1,1'-cyclohexane]-4'-methyl-4'-carboxylic acid produced in Reference Example 5 and N-methyl-N-(pyrrolidinoethyl)amine as materials.

$^1$HNMR (400 MHz, CDCl$_3$, δ): 1.35 (3H, s), 1.64 (2H, d, J=13.7 Hz), 1.72-1.86 (6H, m), 2.08-2.20 (2H, m), 2.36 (2H, d, J=13.7 Hz), 2.55-2.63 (4H, m), 2.64-2.73 (2H, m), 3.14 (3H, s), 3.61 (2H, t, J=7.3 Hz), 3.85 (3H, s), 7.16-7.25 (2H, m), 7.27-7.30 (1H, m); mass spectrum (ESI): 401.3 (M+H)

Example 23 trans-5'-Hydroxy-3'-oxo-N-methyl-N-(2-piperidin-1-ylethyl)-spiro[cyclohexane-1,1'-(3'H)-isobenzofuran]-4-carboxamide

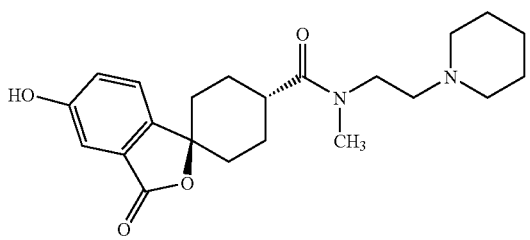

A 1M solution of boron tribromide in dichloromethane (2.0 mL) was added at 0° C. to a solution of trans-5'-methoxy-3'-oxo-N-methyl-N-(2-piperidin-1-ylethyl)-spiro[cyclohexane-1,1'-(3'H)-isobenzofuran]-4-carboxamide (370 mg) produced in Example 9 in dichloromethane (2.0 mL) and the mixture was stirred at 0° C. for 1 hour. A 1M solution of boron tribromide in dichloromethane (6.0 mL) was further added thereto and the mixture was stirred at room temperature for 1 hour. The reaction solution was poured into ice water, neutralized with sodium hydrogen carbonate and extracted with ethyl acetate. The organic layer was washed with a saturated saline solution, dried over sodium sulfate, filtered, concentrated in vacuo and purified by a reversed phase HPLC (0.1% TFA acetonitrile:H$_2$O=5% to 50% gradient) to give the title compound (30 mg, 6%) as a white solid.

$^1$HNMR (400 MHz, CDCl$_3$, δ): 1.40-1.70 (6H, m), 1.88-2.20 (8H, m), 2.38-2.68 (6H, m), 2.82-2.94 (1H, m), 3.03 (3×½, s), 3.16 (3H×½, s), 3.50 (2H×½, d, J=7.2 Hz), 3.61 (2H×½, d, J=7.2 Hz), 7.28-7.42 (2H, m), 7.63 (1H×½, d, J=8.2 Hz), 7.71 (1H×½, d, J=8.2 Hz); mass spectrum (ESI): 387.4 (M+H)

Example 24 trans-3'-Oxo-N-ethyl-N-(2-piperidin-1-ylethyl)-spiro[cyclohexane-1,1'-(3'H)-isobenzofuran]-4-carboxamide hydrochloride

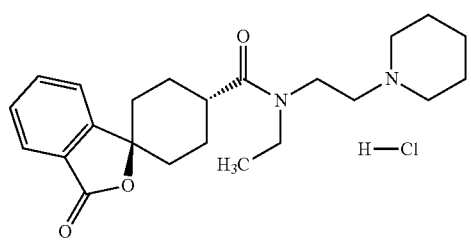

Sodium hydride (4 mg) was added at 0° C. to a solution of trans-3'-oxo-N-(2-piperidin-1-ylethyl)-spiro[cyclohexane-1,1'-(3'H)-isobenzofuran]-4-carboxamide (30 mg) produced in Example 4 in N,N-dimethylformamide (1.0 mL) and the mixture was stirred at 0° C. for 25 minutes. Ethyl iodide (0.008 mL) was added thereto and the mixture was stirred at room temperature for 20 hours. A 10% aqueous solution of phosphoric acid was added to the reaction solution to adjust the pH to about 1 and then a saturated aqueous solution of sodium hydrogen carbonate was added thereto followed by extracting with ethyl acetate. The organic layer was washed with a saturated saline solution, dried over sodium sulfate, filtered, concentrated in vacuo and purified by a reversed phase HPLC (0.1% TFA acetonitrile:H$_2$O=5% to 50% gradient). The resulting residue was dissolved in ethyl acetate (3.0 mL), a 4N hydrogen chloride in ethyl acetate solution (0.1 mL) was added thereto and the mixture was concentrated in vacuo. Ethyl acetate was added thereto to suspend and the solid separated out therefrom was filtered to give the title compound (17 mg, 48%) as a colorless solid.

$^1$HNMR (400 MHz, DMSO-d$_6$, δ): 1.04 (3H×¼, t, J=7.0 Hz), 1.17 (3H×¾, t, J=7.0 Hz), 1.30-2.09 (14H, m), 2.82-3.86 (11H, m), 7.60-7.88 (4H, m), 9.82 (1H×¾, brs), 10.60 (1H×¼, brs); mass spectrum (ESI): 385.4 (M+H)

Example 25 trans-4-Cyclopentylpiperazinyl-3'-oxo-spiro[cyclohexane-1,1'-(3'H)-isobenzofuran]-4-carboxamide

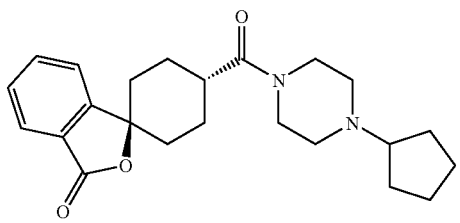

Triethylamine (0.368 mL), tert-butyl 1-piperazine-carboxylate (416 mg) and 2N solution of 2-chloro-1,3-dimethylimidazolinium chloride in dichloromethane (1.10 mL)

were added at 0° C. to a solution of trans-3-oxo-3H-spiro-[2-benzofuran-1,1'-cyclohexane]-4'-carboxylic acid (500 mg) produced in Reference Example 1-2 in chloroform (10 mL) and, after that, the mixture was stirred at 0° C. for 30 minutes. To the reaction solution was added a saturated aqueous solution of sodium hydrogen carbonate and the mixture was extracted with ethyl acetate. The organic layer was washed with a saturated saline solution, dried over sodium sulfate, filtered and concentrated in vacuo. The residue was dissolved in ethyl acetate (5.0 mL), a 4N solution of hydrogen chloride in ethyl acetate (10 mL) was added thereto and the mixture was stirred at room temperature for 2 hours and concentrated in vacuo to give a colorless solid (787 mg). To a solution of the resulting residue (100 mg) in methanol (2.0 mL) were added triethylamine (0.036 mL), cyclopentanone (0.043 mL) and a 0.3 N methanolic solution of zinc chloride-sodium cyanoborohydride in methanol (1.0 mL) at 0° C. and the mixture was stirred at room temperature for 17 hours. A saturated aqueous solution of sodium hydrogen carbonate was added to the reaction solution followed by extracting with ethyl acetate. The organic layer was washed with a saturated saline solution, dried over sodium sulfate, filtered and concentrated in vacuo. The residue was purified by silica gel column chromatography (Biotage NH Column, hexane/ethyl acetate=3/1) to give the title compound (56 mg, 57%) as a colorless solid.

$^1$HNMR (400 MHz, CDCl$_3$, δ): 1.22-1.33 (2H, m), 1.36-1.46 (2H, m), 1.50-1.62 (2H, m), 1.64-1.92 (6H, m), 2.00-2.12 (2H, m), 2.24-2.34 (2H, m), 2.46-2.56 (5H, m), 2.88-2.96 (1H, m), 3.58 (2H, t, J=4.8 Hz), 3.67 (2H, t, J=4.8 Hz), 7.46-7.53 (1H, m), 7.59-7.66 (2H, m), 7.84-7.88 (1H, m); mass spectrum (ESI): 383.3 (M+H)

The compounds of Examples 26 to 31 can be produced by the same method as in Example 25, by a method similar thereto or by a combination of those methods with a conventional method by using the corresponding ketone or aldehyde as materials.

Example 26 trans-4-Cyclohexylpiperazinyl-3'-oxo-spiro[cyclohexane-1,1'-(3'H)-isobenzofuran]-4-carboxamide

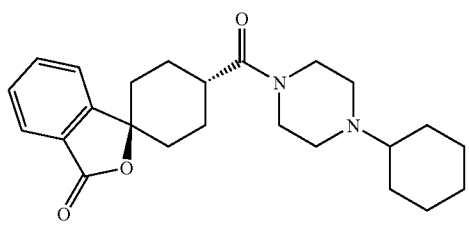

A method according to Example 25 was carried out to produce the title compound using trans-piperazinyl-3'-oxo-spiro[cyclohexane-1,1'-(3'H)-isobenzofuran]-4-carboxamide hydrochloride produced in Example 25 and cyclopentanone as materials.

$^1$HNMR (400 MHz, CDCl$_3$, δ): 1.04-1.94 (14H, m), 1.98-2.12 (2H, m), 2.24-2.36 (2H, m), 2.52-2.70 (5H, m), 2.87-2.96 (1H, m), 3.53 (2H, t, J=4.8 Hz), 3.60-3.70 (2H, m), 7.44-7.54 (1H, m), 7.60-7.66 (2H, m), 7.82-7.88 (1H, m); mass spectrum (ESI): 397.3 (M+H)

Example 27 trans-4-Butylpiperazinyl-3'-oxo-spiro[cyclohexane-1,1'-(3'H)-isobenzofuran]-4-carboxamide

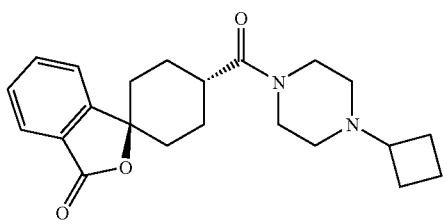

A method according to Example 17 was carried out to produce the title compound using trans-piperazinyl-3'-oxo-spiro[cyclohexane-1,1'-(3'H)-isobenzofuran]-4-carboxamide hydrochloride produced in Example 25 and cyclobutanone as materials.

$^1$HNMR (400 MHz, CDCl$_3$, δ): 1.64-1.94 (6H, m), 1.98-2.12 (6H, m), 2.24-2.38 (6H, m), 2.68-2.78 (1H, m), 2.86-2.96 (1H, m), 3.55 (2H, t, J=4.8 Hz), 3.67 (2H, t, J=4.8 Hz), 7.45-7.52 (1H, m), 7.58-7.66 (2H, m), 7.82-7.88 (1H, m); mass spectrum (ESI): 369.3 (M+H)

Example 28 trans-4-(1-Ethylpropyl)piperazinyl-3'-oxo-spiro[cyclohexane-1,1'-(3'H)-isobenzofuran]-4-carboxamide

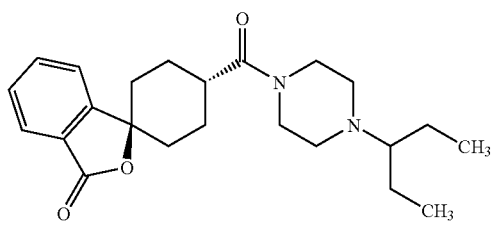

A method according to Example 25 was carried out to produce the title compound using trans-piperazinyl-3'-oxo-spiro[cyclohexane-1,1'-(3'H)-isobenzofuran]-4-carboxamide hydrochloride produced in Example 25 and 3-pentanone as materials.

$^1$HNMR (400 MHz, CDCl$_3$, δ): 0.91 (6H, t, J=7.3 Hz), 1.24-1.38 (2H, m), 1.40-1.52 (2H, m), 1.78-1.88 (2H, m), 2.00-2.12 (4H, m), 2.05-2.24 (1H, m), 2.25-2.34 (2H, m), 2.46-2.58 (4H, m), 2.88-2.96 (1H, m), 3.50 (2H, t, J=4.8 Hz), 3.62 (2H, t, J=4.8 Hz), 7.46-7.54 (1H, m), 7.58-7.66 (2H, m), 7.84-7.88 (1H, m); mass spectrum (ESI): 385.3 (M+H)

Example 29 trans-4-(1-Methylpropyl)piperazinyl-3'-oxo-spiro[cyclohexane-1,1'-(3'H)-isobenzofuran]-4-carboxamide

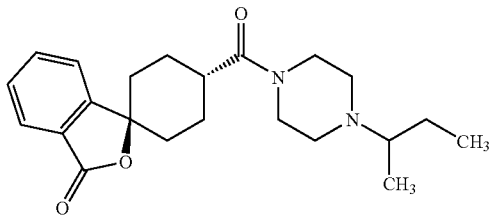

A method according to Example 25 was carried out to produce the title compound using trans-piperazinyl-3'-oxo-spiro[cyclohexane-1,1'-(3'H)-isobenzofuran]-4-carboxamide hydrochloride produced in Example 25 and 2-butanone as materials.

$^1$HNMR (400 MHz, CDCl$_3$, δ): 0.91 (3H, t, J=7.3 Hz), 0.97 (3H, d, J=6.6 Hz), 1.24-1.36 (1H, m), 1.50-1.64 (1H, m), 1.78-1.88 (2H, m), 1.98-2.12 (4H, m), 2.22-2.34 (2H, m), 2.42-2.62 (5H, m), 2.88-2.96 (1H, m), 3.46-3.72 (4H, m), 7.46-7.54 (1H, m), 7.58-7.66 (2H, m), 7.82-7.88 (1H, m); mass spectrum (ESI): 371.3 (M+H)

Example 30 trans-4-Isopropylpiperazinyl-3'-oxo-spiro[cyclohexane-1,1'-(3'H-isobenzofuran]-4-carboxamide

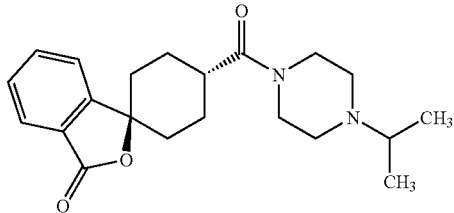

A method according to Example 17 was carried out to produce the title compound using trans-piperazinyl-3'-oxo-spiro[cyclohexane-1,1'-(3'H)-isobenzofuran]-4-carboxamide hydrochloride produced in Example 25 and acetone as materials.

$^1$HNMR (400 MHz, CDCl$_3$, δ): 1.06 (6H, d, J=6.6 Hz), 1.78-1.88 (2H, m), 1.96-2.14 (4H, m), 2.24-2.34 (2H, m), 2.48-2.58 (4H, m), 2.66-2.78 (1H, m), 2.88-2.98 (1H, m), 3.55 (2H, t, J=4.4 Hz), 3.67 (2H, t, J=4.4 Hz), 7.46-7.54 (1H, m), 7.58-7.66 (2H, m), 7.83-7.88 (1H, m); mass spectrum (ESI): 357.2 (M+H)

Example 31 trans-4-Propylpiperazinyl-3'-oxo-spiro[cyclohexane-1,1'-(3'H)-isobenzofuran]-4-carboxamide

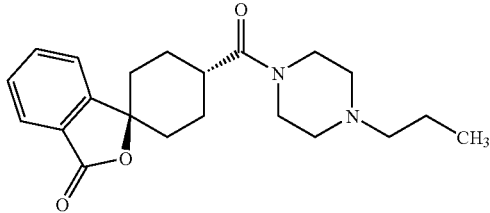

A method according to Example 25 was carried out to produce the title compound using trans-piperazinyl-3'-oxo-spiro[cyclohexane-1,1'-(3'H)-isobenzofuran]-4-carboxamide hydrochloride produced in Example 25 and propionaldehyde as materials.

$^1$HNMR (400 MHz, CDCl$_3$, δ): 0.92 (3H, t, J=7.3 Hz), 1.46-1.58 (2H, m), 1.78-1.96 (2H, m), 1.98-2.12 (4H, m), 2.24-2.37 (4H, m), 2.40-2.52 (4H, m), 2.88-2.96 (1H, m), 3.56 (2H, t, J=4.8 Hz), 3.67 (2H, t, J=4.8 Hz), 7.45-7.55 (1H, m), 7.58-7.68 (2H, m), 7.82-7.88 (1H, m); mass spectrum (ESI): 357.3 (M+H)

Example 32 trans-5'-Fluoromethoxy-3'-oxo-(N-methyl-N-(2-piperidin-1-ylethyl)-spiro[cyclohexane-1,1'-(3'H)-iso-benzofuran]-4-carboxamide hydrochloride

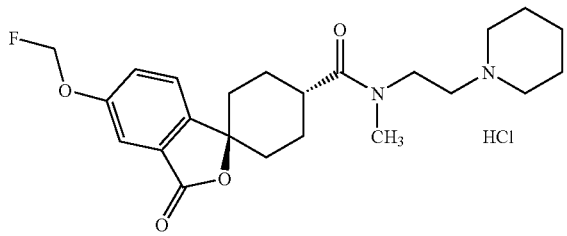

Fluoromethyl tosylate (0.05 mL) and potassium carbonate (50 mg) were added to a solution of trans-5'-hydroxy-3'-oxo-(N-methyl-N-(2-piperidin-1-ylethyl)-spiro[cyclohexane-1,1'-(3'H)-isobenzofuran]-4-carboxamide (50 mg) produced in Example 23 in acetone (0.8 mL) and the mixture was stirred in a sealed tube at 70° C. for 20 hours. After water was added thereto, the mixture was extracted with ethyl acetate. The organic layer was washed with a saturated saline solution, dried over sodium sulfate, filtered, concentrated in vacuo and purified by a reverse phase HPLC (0.1% TFA acetonitrile: H$_2$O=5% to 50%, gradient) to give a free base of the title compound as a colorless oily compound. The resulting free base (40 mg) was dissolved in ethyl acetate (1.0 mL), a 4N solution of hydrogen chloride in ethyl acetate (0.05 mL) was added thereto and the mixture was concentrated in vacuo. Ethyl acetate was added thereto to suspend and the solid separated out therefrom was filtered to give the title compound (30 mg, 69%) as a colorless solid.

$^1$HNMR (400 MHz, DMSO-d$_6$, δ): 1.29-2.10 (14H, m), 2.82-3.30 (5H, m), 2.86 (3H×¼, s), 3.09 (3H×¾), 3.42-3.55 (2H, m), 3.63-3.88 (2H, m), 5.97 (2H, d, J=53.8 Hz), 7.49-7.73 (3H, m), 9.65 (1H×¾, brs), 10.55 (1H×¼, brs); mass spectrum (ESI): 419.2 (M+H)

Example 33

N-Methyl-3-oxo-N-(2-piperidin-1-ylethyl)-1'H,3H-spiro[2-benzofuran-1,4'-piperidine]-1'-carboxamide hydrochloride

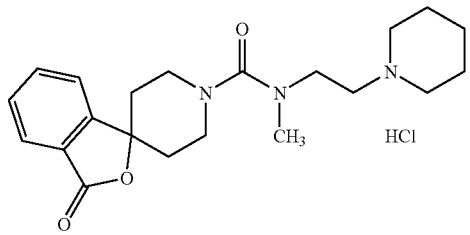

Triethylamine (0.811 mL) was added to a solution of 3H-spiro[2-benzofuran-1,4'-piperazine]-3-one hydrochloride monohydrate (300 mg) in chloroform (5.0 mL), then triphosgene (345 mg) was added thereto at 0° C. and the mixture was stirred at 0° C. for 20 minutes. To the reaction solution was added a saturated aqueous solution of sodium bicarbonate followed by extracting with ethyl acetate. The organic layer was washed with a saturated saline solution, dried over sodium sulfate, filtered and concentrated in vacuo. The resulting residue was dissolved in chloroform (5.0 mL), then N-methyl-N-(piperidinoethyl)amine (215 mg) and triethylamine (0.811 mL) were added thereto and, after that, the mixture was stirred for 3 hours at 70° C. in a nitrogen atmosphere. A saturated sodium bicarbonate solution was added to the reaction solution and the mixture was extracted with ethyl acetate. The organic layer was washed with a saturated saline solution, dried over sodium sulfate, filtered and concentrated in vacuo. This was purified by a silica gel column chromatography (ethyl acetate→chloroform/methanol=9/1), the resulting residue was dissolved in ethyl acetate (2.0 mL), a 4N solution of hydrogen chloride in ethyl acetate (1.0 mL) was added thereto and the mixture was concentrated in vacuo. This was suspended by addition of ethyl acetate thereto and the solid separated out therefrom was filtered to give the title compound (384 mg, 81%) as a colorless solid.

$^1$HNMR (400 MHz, DMSO-d$_6$, δ): 1.58-1.84 (6H, m), 2.17-2.30 (2H, m), 2.82-2.96 (2H, m), 2.89 (3H, s), 3.04-3.24 (4H, m), 3.38-3.57 (4H, m), 3.58-3.78 (4H, m), 7.58-7.65 (1H, m), 7.76-7.81 (2H, m), 7.83 (1H, d, J=7.6 Hz), 10.26 (1H, brs); mass spectrum (ESI): 372.3 (M+H)

The compounds of Examples 34 to 42 can be produced using the corresponding amine as a material by the same method as in Example 33, by a method similar thereto or by combining such methods with a conventional method.

Example 34

N-Methyl-N-(2-piperidin-1-ylethyl)-1'H,3H-spiro[2-benzofuran-1,4'-piperidine]-1'-carboxamide hydrochloride

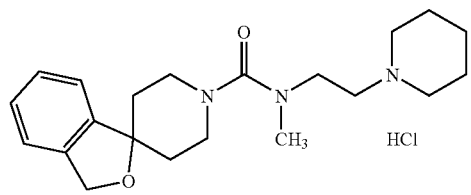

The title compound was prepared by the method according to Example 33 using 3H-spiro[2-benzofuran-1,4'-piperidine]-3-one hydrochloride and methyl-N-(piperidinoethyl)amine as materials.

$^1$HNMR (400 MHz, DMSO-d$_6$, δ): 1.24-1.95 (10H, m), 2.81-2.97 (2H, m), 2.86 (3H, s), 2.99-3.28 (4H, m), 3.31-3.66 (6H, m), 4.99 (2H, s), 7.23-7.31 (4H, m), 10.55 (1H, brs); mass spectrum (ESI): 358.4 (M+H)

Example 35

4-Fluoro-N-methyl-3-oxo-N-(2-piperidin-1-ylethyl)-1'H,3H-spiro[2-benzofuran-1,4'-piperidine]-1'-carboxamide

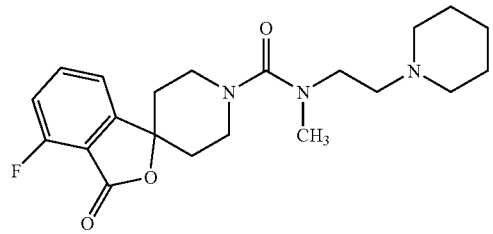

The title compound was prepared by the method according to Example 33 using 4-fluoro-3H-spiro[2-benzofuran-1,4'-piperidine]-3-one hydrochloride and methyl-N-(piperidinoethyl)amine as materials.

$^1$HNMR (400 MHz, CDCl$_3$, δ): 1.42-1.52 (2H, m), 1.54-1.78 (6H, m), 2.21 (2H, dt, J=4.7 Hz, 13.7 Hz), 2.40-2.60 (6H, m), 2.94 (3H, s), 3.30-3.44 (4H, m), 3.76-3.86 (2H, m), 7.17-7.24 (2H, m), 7.66-7.74 (1H, m); mass spectrum (ESI): 390.2 (M+H)

Example 36

N,2-Dimethyl-3-oxo-N-(2-piperidin-1-ylethyl)-2,3-di-hydro-1'H-spiro[isoindole-1,4'-piperidine]-1'-carboxamide

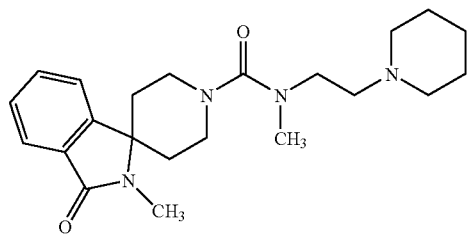

The title compound was prepared by the method according to Example 33 using 2-methyl-spiro[isoindole-1,4'-piperidine]-3(2H)-one hydrochloride and methyl-N-(piperidinoethyl)amine as materials.

$^1$HNMR (400 MHz, CDCl$_3$, δ): 1.21-1.68 (8H, m), 2.24 (2H, dt, J=4.9 Hz, 13.1 Hz), 2.42-2.64 (6H, m), 2.96 (3H, s), 3.05 (3H, s), 3.38-3.54 (4H, m), 3.76-3.86 (2H, m), 7.47-7.57 (2H, m), 7.84 (1H, d, J=6.8 Hz), 7.90 (1H, dd, J=6.8 Hz, 1.8 Hz); mass spectrum (ESI): 385.4 (M+H)

Example 37

1-(Ethylsulfonyl)-N-methyl-N-(2-piperidin-1-ylethyl)-1,2-dihydro-1'H-spiro[indole-3,4'-piperidine]-1'-carboxamide

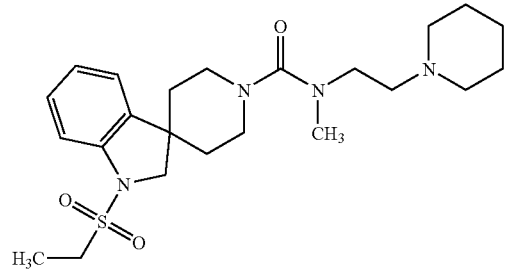

The title compound was prepared by the method according to Example 33 using 2-(ethylsulfonyl)-1,2-dihydrospiro-[indole-3,4'-piperidine] and methyl-N-(piperidinoethyl)amine as materials.

$^1$HNMR (400 MHz, CDCl$_3$, δ): 1.39-1.48 (2H, m), 1.42 (3H, t, J=7.4 Hz), 1.54-1.62 (4H, m), 1.68 (2H, d, J=13.6 Hz), 1.87-1.97 (2H, m), 2.44 (4H, brs), 2.52 (2H, t, J=7.1 Hz), 2.83-2.94 (2H, m), 2.90 (3H, s), 3.15 (2H, q, J=7.4 Hz), 3.35 (2H, t, J=7.1 Hz), 3.69 (2H, d, J=7.1 Hz), 3.92 (2H, s), 7.03 (1H, t, J=7.4 Hz), 7.17 (1H, d, J=7.4 Hz), 7.19-7.23 (1H, m), 7.35 (1H, d, J=8.0 Hz); mass spectrum (ESI): 449.2 (M+H)

Example 38

N-Methyl-3-(methylsulfonyl)-N-(2-piperidin-1-yl-ethyl)-2,3-dihydro-1'H-spiro[indene-1,4'-piperidine]-1'-carboxamide

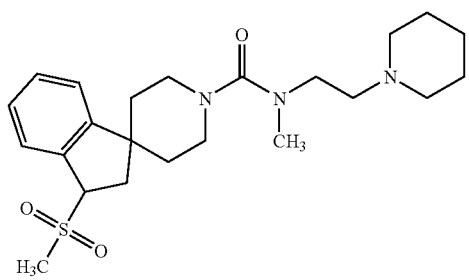

The title compound was prepared by the method according to Example 33 using 3-(methylsulfonyl)-2,3-dihydrospiro[indene-1,4'-piperidine] and methyl-N-(piperidinoethyl)-amine as materials.

$^1$HNMR (400 MHz, CDCl$_3$, δ): 1.39-1.47 (3H, m), 1.54-1.64 (4H, m), 1.76-1.86 (2H, m), 2.00-2.08 (1H, m), 2.38-2.72 (8H, m), 2.80 (3H, s), 2.90 (3H, s), 2.90-3.01 (2H, m), 3.35-3.38 (2H, m), 3.65-3.75 (2H, m), 4.63-4.73 (1H, m), 7.24-7.28 (1H, m), 7.30-7.34 (1H, m), 7.38-7.42 (1H, m), 7.68 (1H, d, J=7.6 Hz); mass spectrum (ESI): 434.3 (M+H)

Example 39

5-Fluoro-N-methyl-N-(2-piperidin-1-ylethyl)-1'H,3H-spiro[2-benzofuran-1,4'-piperidine]-1'-carboxamide

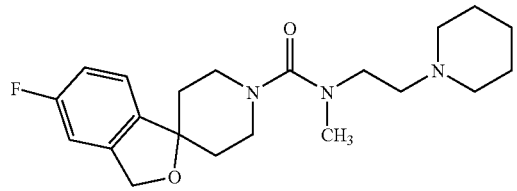

The title compound was prepared by the method according to Example 33 using 5-fluoro-3H-spiro[2-benzofuran-1,4'-piperidine] and methyl-N-(piperidinoethyl)amine as materials.

$^1$HNMR (400 MHz, CDCl$_3$, δ): 1.39-1.47 (2H, m), 1.53-1.61 (4H, m), 1.71 (2H, d, J=12.5 Hz), 1.80-1.94 (2H, m), 2.42 (4H, brs), 2.51 (2H, t, J=7.1 Hz), 2.88 (3H, s), 3.17-3.28 (2H, m), 3.34 (2H, t, J=7.1 Hz), 3.64-3.69 (2H, m), 5.04 (2H, s), 6.89-7.00 (2H, m), 7.03-7.06 (1H, m); mass spectrum (ESI): 376.3 (M+H)

Example 40

1-{2-[[(3,3-Dimethyl-1'H,3H-spiro[2-benzofuran-1,4'-piperidine]-1'-yl)carbonyl](methyl)amino]ethyl}piperidine trifluoroacetate

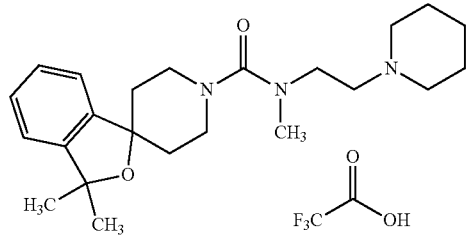

The title compound was prepared by the method according to Example 33 using 3,3-dimethyl-3H-spiro[2-benzofuran-1,4'-piperidine] and methyl-N-(piperidinoethyl)amine as materials.

$^1$HNMR (400 MHz, CDCl$_3$, δ): 1.35-2.09 (10H, m), 1.50 (6H, s), 2.62-2.77 (2H, m), 2.93 (3H, s), 3.23-3.37 (4H, m), 3.57 (3H, t, J=7.1 Hz), 3.61-3.70 (3H, m), 7.05-7.14 (2H, m), 7.25-7.33 (2H, m); mass spectrum (ESI): 386.6 (M+H)

Example 41

N-Methyl-3-oxo-N-(2-piperidin-1-ylethyl)-2,3-dihydro-1'H-spiro[isoindole-1,4'-piperidine]-1'-carboxamide

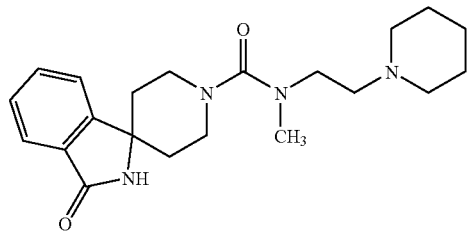

The title compound was prepared by the method according to Example 33 using spiro[isoindole-1,4'-piperidine]-3(2H)-one and methyl-N-(piperidinoethyl)amine as materials.

$^1$HNMR (400 MHz, CDCl$_3$, δ): 1.37-1.50 (2H, m), 1.53-1.65 (6H, m), 2.13-2.26 (2H, m), 2.35-2.65 (6H, m), 2.94 (3H, s), 3.08-3.20 (2H, m), 3.40 (2H, t, J=7.1 Hz), 3.77-3.87 (2H, m), 7.43 (1H, d, J=7.3 Hz), 7.46-7.51 (1H, m), 7.56-7.62 (1H, m), 7.85 (1H, d, J=7.3 Hz), 8.03 (1H, s); mass spectrum (ESI): 371.3 (M+H)

Example 42

N-Methyl-3-oxo-N-(2-piperidin-1-ylethyl)-2,3-dihydro-1'H-spiro[indene-1,4'-piperidine]-1'-carboxamide

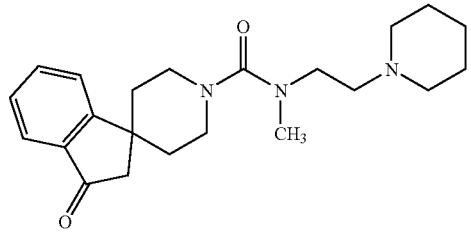

The title compound was prepared by the method according to Example 33 using spiro[indene-1,4'-piperidine]-3(2H)-one and methyl-N-(piperidinoethyl)amine as materials.

$^1$HNMR (400 MHz, CDCl$_3$, δ): 1.37-1.47 (2H, m), 1.52-1.63 (6H, m), 2.01-2.13 (2H, m), 2.35-2.57 (6H, m), 2.65 (2H, s), 2.80-3.00 (5H, m), 3.33-3.41 (2H, m), 3.70-3.80 (2H, m), 7.37-7.46 (1H, m), 7.49-7.57 (1H, m), 7.61-7.69 (1H, m), 7.71-7.78 (1H, m); mass spectrum (ESI): 370.3 (M+H)

Example 43 trans-5'-Methoxy-3'-oxo-N-methyl-N-{2-[(3S)-3-methylpiperidin-1-yl]ethyl}-spiro[cyclohexane-1,1'-(3'H)-isobenzofuran]-4-carboxamide

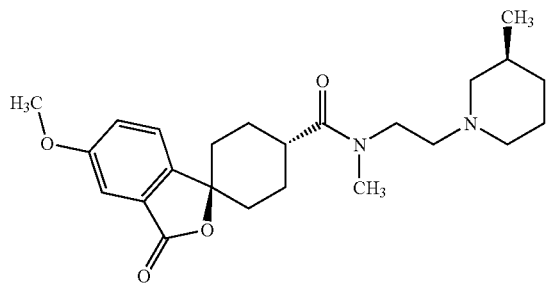

N,N-Diisopropylethylamine (2.27 mL), trans-5-methoxy-3-oxo-3H-spiro[2-benzofuran-1,1'-cyclohexane]-4'-carboxylic acid (3.00 g) produced in Reference Example 1-3 and HATU (4.96 g) were added to a solution of N-methylethanolamine (816 mg) in chloroform (20 mL) at 0° C. and then stirred for 15 hours at room temperature in a nitrogen atmosphere. To the reaction solution was added a saturated aqueous solution of ammonium chloride followed by extracting with ethyl acetate. The organic layer was washed with a saturated sodium bicarbonate solution and a saturated saline solution successively, dried over sodium sulfate, filtered and concentrated in vacuo. The resulting residue was purified by a silica gel column chromatography (hexane/ethyl acetate=¼) to give a colorless solid (2.89 g, 80%). The resulting residue (300 mg) was dissolved in dimethyl sulfoxide (5.0 mL), a complex of sulfur trioxide pyridine complex (286 mg) was added thereto and the mixture was stirred for 2 days at room temperature in a nitrogen atmosphere. Water was added to the reaction solution followed by extracting with ethyl acetate. The organic layer was washed with a saturated saline solution, dried over sodium sulfate, filtered and concentrated in vacuo. The resulting residue was dissolved in dichloromethane (5.0 mL), then (3S)-3-methylpiperidine (2S)-2-phenylpropionate (451 mg), acetic acid (0.103 mL) and sodium triacetoxyborohydride (570 mg) were added thereto and the mixture was stirred for 17 hours at room temperature in a nitrogen atmosphere. A saturated sodium bicarbonate solution was added to the reaction solution followed by extracting with ethyl acetate. The organic layer was washed with a saturated saline solution, dried over sodium sulfate, filtered and concentrated in vacuo. This was purified by a silica gel column chromatography (Biotage Column NH, hexane/ethyl acetate=3/1) to give the title compound (345 mg, 92%) as a colorless oily substance.

$^1$HNMR (400 MHz, CDCl$_3$, δ): 0.80-0.95 (3H, m), 1.45-2.12 (13H, m), 2.16-2.28 (2H, m), 2.44-2.52 (2H, m), 2.75-2.96 (3H, m), 2.98 (3H×½, s), 3.12 (3H×½, s), 3.42-3.60 (2H, m), 3.86 (3H, s), 7.18-7.23 (1H, m), 7.30-7.33 (1H, m), 7.58 (1H×½, d, J=8.4 Hz), 7.63 (1H×½, d, J=8.4 Hz); mass spectrum (ESI): 415.3 (M+H)

The compounds of Examples 44 to 49 can be produced using the corresponding amine as a material by the same method as in Example 43, by a method similar thereto or by combining such methods with a conventional method.

Example 44 trans-5'-Methoxy-3'-oxo-N-methyl-N-[2-(dimethylamino)ethyl]-spiro[cyclohexane-1,1'-(3'H)-isobenzofuran]-4-carboxamide

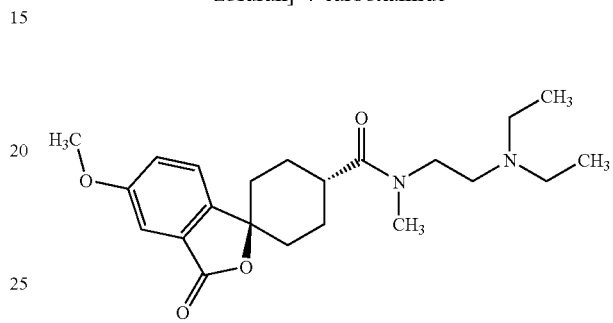

A method according to Example 43 was carried out to produce the title compound using trans-5-methoxy-3-oxo-3H-spiro[2-benzofuran-1,1'-cyclohexane]-4'-carboxylic acid produced in Reference Example 1-3 and diethylamine as materials.

$^1$HNMR (400 MHz, CDCl$_3$, δ): 1.05 (6H, t, J=7.1 Hz), 1.80-1.93 (2H, m), 1.98-2.12 (4H, m), 2.16-2.28 (2H, m), 2.51-2.65 (6H, m), 2.76-2.98 (1H, m), 2.99 (3H×½, s), 3.14 (3H×½, s), 3.38-3.55 (2H, m), 3.87 (3H, s), 7.18-7.24 (1H, m), 7.30-7.34 (1H, m), 7.60 (1H×½, d, J=8.4 Hz), 7.64 (1H×½, d, J=8.4 Hz); mass spectrum (ESI): 389.3 (M+H)

Example 45 trans-5'-Methoxy-3'-oxo-N-methyl-N-[2-azeditin-1-ylethyl]-spiro[cyclohexane-1,1'-(3'H)-isobenzofuran]-4-carboxamide

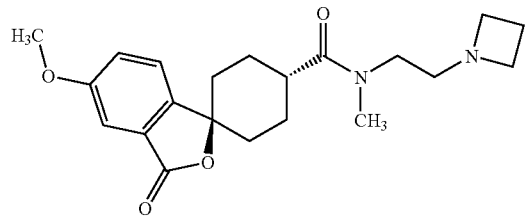

A method according to Example 43 was carried out to produce the title compound using trans-5-methoxy-3-oxo-3H-spiro[2-benzofuran-1,1'-cyclohexane]-4'-carboxylic acid produced in Reference Example 1-3 and azetidine as materials.

$^1$HNMR (400 MHz, CDCl$_3$, δ): 1.77-2.16 (8H, m), 2.16-2.32 (2H, m), 2.53-2.67 (2H, m), 2.83-2.95 (1H, m), 2.97 (3H×½, s), 3.11 (3H×½, s), 3.24 (4H, t, J=6.8 Hz), 3.29-3.42

(2H, m), 3.86 (3H, s), 7.17-7.24 (1H, m), 7.30-7.34 (1H, m), 7.59 (1H×½, d, J=8.3 Hz), 7.62 (1H×½, d, J=8.3 Hz); mass spectrum (ESI): 373.3 (M+H)

Example 46 trans-5'-Methoxy-3'-oxo-N-methyl-N-{2-[(2R)-2-methylpyrrolidin-1-yl]ethyl}-spiro[cyclohexane-1,1'-(3'H)-isobenzofuran]-4-carboxamide

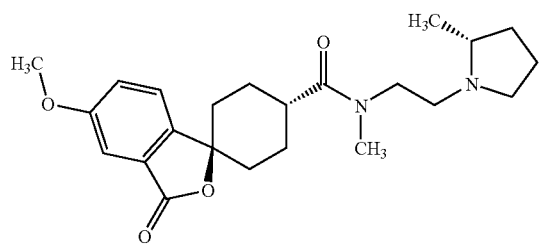

A method according to Example 43 was carried out to produce the title compound using trans-5-methoxy-3-oxo-3H-spiro[2-benzofuran-1,1'-cyclohexane]-4'-carboxylic acid produced in Reference Example 1-3 and (2R)-2-methylpyrrolidine hydrobromide as materials.

$^1$HNMR (400 MHz, CDCl$_3$, δ): 1.02-1.16 (3H, m), 1.30-2.50 (15H, m), 2.83-3.03 (3H, m), 3.00 (3H×½, s), 3.13 (3H×½, s), 3.13-3.75 (2H, m), 3.86 (3H, s), 7.16-7.26 (1H, m), 7.30-7.34 (1H, m), 7.58 (1H×½, d, J=8.8 Hz), 7.64 (1H×½, d, J=8.8 Hz); mass spectrum (ESI): 401.2 (M+H)

Example 47 trans-5'-Methoxy-3'-oxo-N-methyl-N-[2-(2-methylpiperidin-1-yl)ethyl]-spiro[cyclohexane-1,1'-(3'H)-isobenzofuran]-4-carboxamide

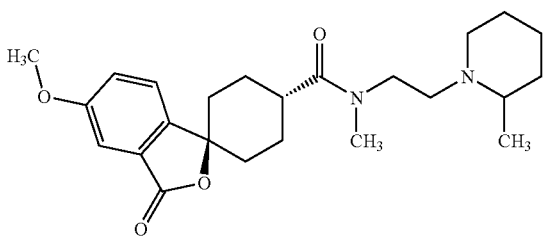

A method according to Example 43 was carried out to produce the title compound using trans-5-methoxy-3-oxo-3H-spiro[2-benzofuran-1,1'-cyclohexane]-4'-carboxylic acid produced in Reference Example 1-3 and 2-methylpiperidine as materials.

$^1$HNMR (400 MHz, CDCl$_3$, δ): 0.99-1.14 (3H, m), 1.16-2.51 (17H, m), 2.82-2.97 (3H, m), 2.98 (3H×½, s), 3.13 (3H×½, s), 3.31-3.66 (2H, m), 3.86 (3H, s), 7.17-7.24 (1H, m), 7.30-7.33 (1H, m), 7.59 (1H×½, d, J=8.8 Hz), 7.64 (1H×½, d, J=8.3 Hz); mass spectrum (ESI): 415.3 (M+H)

Example 48 trans-5'-Methoxy-3'-oxo-N-methyl-N-[2-(2-azepan-1-ylethyl)-spiro[cyclohexane-1,1'-(3'H)-isobenzofuran]-4-carboxamide

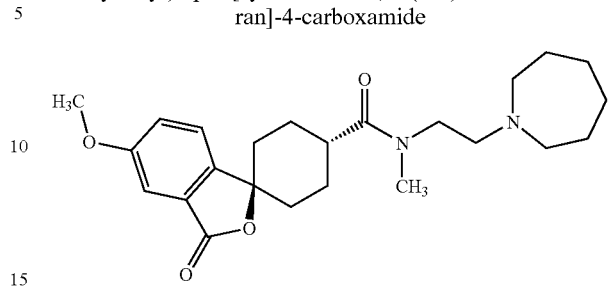

A method according to Example 43 was carried out to produce the title compound using trans-5-methoxy-3-oxo-3H-spiro[2-benzofuran-1,1'-cyclohexane]-4'-carboxylic acid produced in Reference Example 1-3 and azepan as materials.

$^1$HNMR (400 MHz, CDCl$_3$, δ): 1.48-1.93 (10H, m), 1.96-2.31 (6H, m), 2.61-2.75 (6H, m), 2.85-2.97 (1H, m), 2.99 (3H×½, s), 3.13 (3H×½, s), 3.42 (2H×½, t, J=6.8 Hz), 3.50 (2H×½, t, J=6.8 Hz), 3.86 (3H, s), 7.16-7.24 (1H, m), 7.29-7.34 (1H, m), 7.58 (1H×½, d, J=8.3 Hz), 7.63 (1H×½, d, J=8.3 Hz); mass spectrum (ESI): 415.3 (M+H)

Example 49 trans-5'-Methoxy-3'-oxo-N-methyl-N-(2-azocan-1-ylethyl)-spiro[cyclohexane-1,1'-(3'H)-isobenzofuran]-4-carboxamide

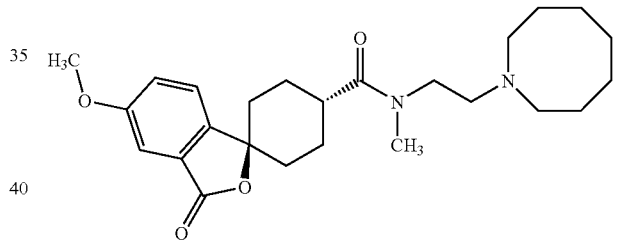

A method according to Example 43 was carried out to produce the title compound using trans-5-methoxy-3-oxo-3H-spiro[2-benzofuran-1,1'-cyclohexane]-4'-carboxylic acid produced in Reference Example 1-3 and azocan as materials.

$^1$HNMR (400 MHz, CDCl$_3$, δ): 1.50-1.82 (12H, m), 1.94-2.28 (6H, m), 2.52-2.74 (6H, m), 2.84-2.95 (1H, m), 2.99 (3H×½, s), 3.12 (3H×½, s), 3.36-3.52 (2H, m), 3.86 (3H, s), 7.17-7.24 (1H, m), 7.30-7.34 (1H, m), 7.54-7.65 (1H, m); mass spectrum (ESI): 429.3 (M+H)

Example 50

2-Piperidin-1-ylethyl 3-oxo-1'H,3H-spiro[2-benzofuran-1,4'-piperidine]-1'-carboxylate

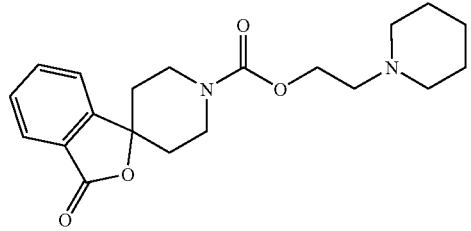

Triphosgene (248 mg) was dissolved in chloroform (8 ml) and, under cooling with ice, N,N-diisopropylethylamine (0.87 mL) and 3H-spiro[2-benzofuran-1,4'-piperidine]-3-one hydrochloride monohydrate (400 mg) were added thereto successively. After the mixture was stirred for 1.5 hours at room temperature, the reaction solution was diluted with ethyl acetate followed by washing with a saturated aqueous solution of sodium hydrogen carbonate. The organic layer was dried over sodium sulfate, filtered and concentrated in vacuo. The residue was dissolved in tetrahydrofuran (4 mL) (this will be called a solution A). 1-Piperidinemethanol (0.44 mL) was dissolved in tetrahydrofuran (8 mL), sodium hydride (134 mg) was added thereto under cooling with ice and the mixture was stirred for 30 minutes under cooling with ice. The solution A was added to the reaction solution at room temperature followed by stirring at room temperature for 2 days. The reaction solution was diluted with ethyl acetate and washed with a saturated aqueous solution of sodium bicarbonate. The organic layer was dried over sodium sulfate, filtered and concentrated in vacuo. The residue was purified by a reversed phase HPLC (0.1% TFA acetonitrile:H$_2$O=10% to 70%, gradient) to give the title compound (226 mg, 44%) as a colorless oily substance.

$^1$HNMR (400 MHz, CDCl$_3$, δ): 1.35-1.49 (2H, m), 1.51-1.65 (4H, m), 1.67-1.78 (2H, m), 2.00-2.18 (2H, m), 2.36-2.55 (4H, m), 2.58-2.75 (2H, m), 3.21-3.43 (2H, m), 4.12-4.40 (4H, m), 7.38 (1H, d, J=7.8 Hz), 7.51-7.59 (1H, m), 7.65-7.73 (1H, m), 7.91 (1H, d, J=7.8 Hz); mass spectrum (ESI): 359.3 (M+H)

Example 51 trans-5'-{[(Trifluoromethyl)sulfonyl]oxy}-3'-oxo-N-methyl-N-(2-piperidin-1-ylethyl)-spiro[cyclohexane-1,1'-(3'H)-isobenzofuran]-4-carboxamide

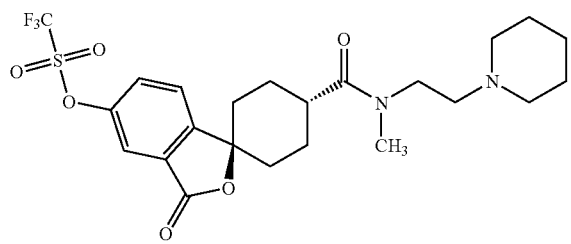

Pyridine (1 mL) and trifluoromethane sulfonic acid anhydride (0.52 mL) were successively added at room temperature to a solution of trans-5'-hydroxy-3'-oxo-N-methyl-N-(2-piperidin-1-ylethyl)-spiro[cyclohexane-1,1'-(3'H)-isobenzofuran-4-carboxamide (1.00 g) prepared in Example 23 in chloroform (20 mL) and the mixture was stirred throughout the night at room temperature. The reaction solution was diluted with ethyl acetate and washed with a saturated aqueous solution of sodium bicarbonate. The organic layer was dried over sodium sulfate, filtered and concentrated in vacuo. The residue was purified by a silica gel column chromatography (Biotage Column NH, hexane/ethyl acetate=10% to 80%, gradient) to give the title compound (1.30 mg, 97%) as a light yellow oily substance $^1$HNMR (400 MHz, CDCl$_3$, δ): 1.38-1.50 (2H, m), 1.52-1.63 (4H, m), 1.77-1.90 (2H, m), 1.96-2.14 (4H, m), 2.30-2.54 (8H, m), 2.92-3.03 (1H, m), 2.98 (3H×½, s), 3.12 (3H×½, s), 3.45 (2H×½, t, J=6.8 Hz), 3.54 (2H×½, t, J=6.8 Hz), 7.52-7.57 (1H, m), 7.73-7.83 (2H, m); mass spectrum (ESI): 519.2 (M+H)

Example 52 trans-5'-{[(Trifluoromethyl)sulfonyl]oxy}-3'-oxo-N-methyl-N-(2-pyrolidin-1-ylethyl)-spiro[cyclohexane-1,1'-(3'H-isobenzofuran]-4-carboxamide

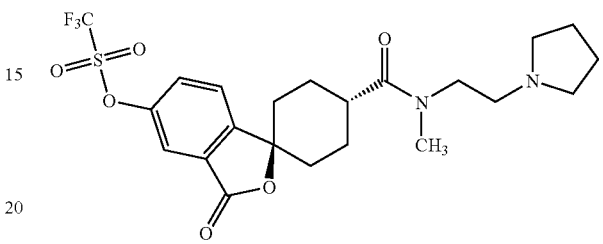

Pyridine (4 mL) and trifluoromethane sulfonic acid anhydride (0.90 mL) were successively added at room temperature to a solution of trans-5'-hydroxy-3'-oxo-N-methyl-N-(2-pyrrolidin-1-ylethyl)-spiro[cyclohexane-1,1'-(3'H)-isobenzofuran]-4-carboxamide (2.00 g) prepared in Example 20 in chloroform (40 mL) and the mixture was stirred throughout the night at room temperature. Trifluoromethane sulfonic acid anhydride (0.90 mL) was added at room temperature to the reaction solution to be stirred for one hour. The reaction solution was diluted with ethyl acetate and washed with a saturated aqueous solution of sodium bicarbonate and a saturated saline solution. The organic layer was dried over sodium sulfate, filtered and concentrated in vacuo. The residue was purified by a silica gel column chromatography (Biotage Column NH, hexane/ethyl acetate=0% to 80%, gradient) to give the title compound (2.38 mg, 88%) as a light yellow oily substance $^1$HNMR (400 MHz, CDCl$_3$, δ): 1.74-1.91 (6H, m), 1.96-2.14 (4H, m), 2.30-2.42 (2H, m), 2.51-2.74 (6H, m), 2.93-3.04 (1H, m), 2.99 (3H×½, s), 3.13 (3H×½, s), 3.45-3.62 (2H, m), 7.50-7.58 (1H, m), 7.72-7.82 (2H, m); mass spectrum (ESI): 505.2 (M+H)

Example 53 trans-5'-(Pyridin-3-yl)-3'-oxo-N-methyl-N-(2-piperidin-1-ylethyl)-spiro[cyclohexane-1,1'-(3'H)-isobenzofuran]-4-carboxamide

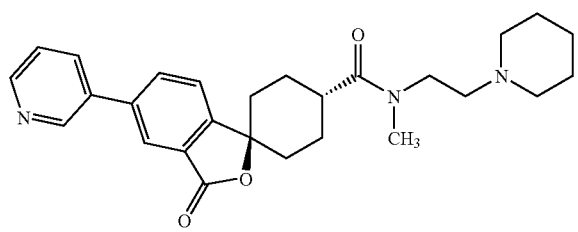

Tetrakistriphenylphosphine palladium (66.9 mg), pyridin-3-ylboronic acid (47.4 mg), sodium carbonate (123 mg) and water (2.0 mL) were successively added at room temperature to a solution of trans-5'-{[(trifluoromethyl)sulfonyl]oxy}-3'- oxo-N-methyl-N-(2-piperidin-1-ylethyl)-spiro[cyclohexane-1,1'-(3'H)-isobenzofuran]-4-carboxamide (100 m g) prepared in Example 51 in ethylene glycol dimethyl ether (3 mL) and stirred at 80° C. for 1 hours. The reaction solution was diluted with ethyl acetate and washed with a saturated saline solution. The organic layer was dried over sodium sulfate, filtered and concentrated in vacuo. The residue was purified by a silica gel column chromatography (Biotage Column NH, hexane/ethyl acetate=0% to 80%, gradient) to give the title compound (53.3 mg, 62%) as a light yellow oily substance $^1$HNMR (400 MHz, CDCl$_3$, δ): 1.40-1.50 (2H, m), 1.53-1.64 (4H, m), 1.83-1.97 (2H, m), 2.03-2.14 (4H, m), 2.29-2.58 (8H, m), 2.92-3.00 (1H, m), 3.00 (3H×½, s), 3.14 (3H×½, s), 3.48 (2H×½, t, J=6.8 Hz), 3.57 (2H×½, t, J=7.1 Hz), 7.40-7.46 (1H, m), 7.77-7.94 (3H, m), 8.08 (1H, s), 8.63-8.69 (1H, m), 8.85-8.91 (1H, m); mass spectrum (ESI): 448.3 (M+H)

The compounds of Examples 54 to 56 can be produced using the corresponding boronic acid as a material by the same method as in Example 53, by a method similar thereto or by combining such methods with a conventional method.

Example 54 trans-5'-(Pyridin-4-yl)-3'-oxo-N-methyl-N-(2-piperidin-1-ylethyl)-spiro[cyclohexane-1,1'-(3'H)-isobenzofuran]-4-carboxamide

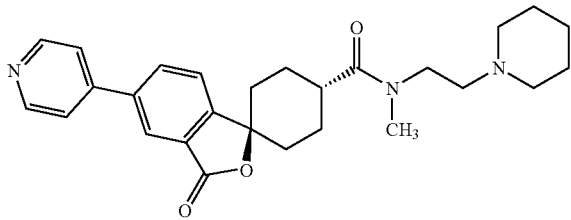

A method according to Example 53 was carried out to produce the title compound using trans-{[(trifluoromethyl)sulfonyl]-oxy}-3'-oxo-N-methyl-N-(2-piperidin-1-ylethyl)-spiro[cyclohexane-1,1'(3H)-isobenzofuran]-4-carboxamide produced in Example 51 and pyridin-4-ylboronic acid as materials.

$^1$HNMR (400 MHz, CDCl$_3$, δ): 1.40-1.51 (2H, m), 1.54-1.66 (4H, m), 1.82-1.96 (2H, m), 2.00-2.17 (4H, m), 2.29-2.60 (8H, m), 2.93-3.01 (1H, m), 3.00 (3H×½, s), 3.14 (3H×½, s), 3.48 (2H×½, t, J=7.1 Hz), 3.58 (2H×½, t, J=7.1 Hz), 7.51-7.56 (2H, m), 7.82 (1H×½, d, J=8.3 Hz), 7.86 (1H×½, d, J=8.3 Hz), 7.89-7.96 (1H, m), 8.11-8.17 (1H, m), 8.67-8.75 (2H, m); mass spectrum (ESI): 448.3 (M+H)

Example 55 trans-5'-(Pyrimidin-5-yl)-3'-oxo-N-methyl-N-(2-piperidin-1-ylethyl)-spiro[cyclohexane-1,1'-(3'H)-isobenzofuran]-4-carboxamide

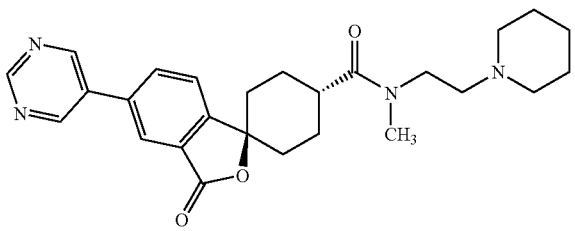

A method according to Example 53 was carried out to produce the title compound using trans-{[(trifluoromethyl)sulfonyl]-oxy}-3'-oxo-N-methyl-N-(2-piperidin-1-ylethyl)-spiro[cyclohexane-1,1'(3H)-isobenzofuran]-4-carboxamide produced in Example 51 and pyrimidin-5-ylboronic acid as materials.

$^1$HNMR (400 MHz, CDCl$_3$, δ): 1.39-1.50 (2H, m), 1.53-1.64 (4H, m), 1.83-1.97 (2H, m), 2.03-2.15 (4H, m), 2.31-2.56 (8H, m), 2.93-3.04 (1H, m), 3.00 (3H×½, s), 3.14 (3H×½, s), 3.48 (2H×½, t, J=6.8 Hz), 3.57 (2H×½, t, J=6.8 Hz), 7.82-7.93 (2H, m), 8.09 (1H, s), 8.99 (2H, s), 9.27 (1H, s); mass spectrum (ESI): 449.3 (M+H)

Example 56 trans-5'-(2-Methoxypyrimidin-5-yl)-3'-oxo-N-methyl-N-(2-pyrrolidin-1-ylethyl)-spiro[cyclohexane-1,1'-(3'H)-isobenzofuran]-4-carboxamide

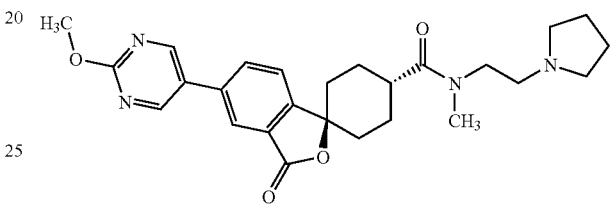

A method according to Example 53 was carried out to produce the title compound using trans-5'-{[(trifluoromethyl)sulfonyl]-oxy}-3'-oxo-N-methyl-N-(2-pyrrolidin-1-ylethyl)-spiro[cyclo-hexane-1,1'-(3'H)-isobenzofuran]-4-carboxamide produced in Example 52 and 2-methoxypyrimidin-5-ylboronic acid as materials.

$^1$HNMR (400 MHz, CDCl$_3$, δ): 1.73-1.97 (6H, m), 2.00-2.16 (4H, m), 2.28-2.43 (2H, m), 2.51-2.77 (6H, m), 2.90-3.03 (1H, m), 3.01 (3H×½, s), 3.14 (3H×½, s), 3.51 (2H×½, t, J=7.4 Hz), 3.58 (2H×½, t, J=7.4 Hz), 4.09 (3H, s), 7.75-7.88 (2H, m), 8.00-8.04 (1H, m), 8.75 (2H, s); mass spectrum (ESI): 465.3 (M+H)

Example 57 trans-5'-(Pyrazin-2-yl)-3'-oxo-N-methyl-N-(2-piperidin-1-ylethyl)-spiro[cyclohexane-1,1'-(3'H)-isobenzofuran]-4-carboxamide

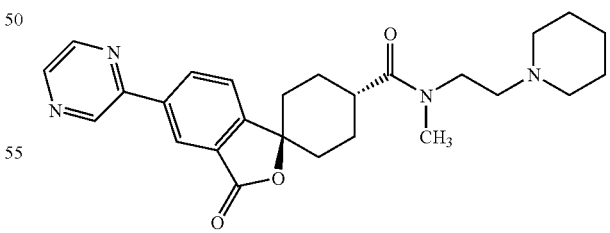

Tetrakistriphenylphosphine palladium (44.6 mg), 2-(tri-n-butyl tin)pyrazine (85.4 mg) and lithium chloride (24.5 mg) were successively added at room temperature to a solution of trans-5'-{[(trifluoromethyl)sulfonyl]oxy}-3'-oxo-N-methyl-N-(2-piperidin-1-ylethyl)-spiro[cyclohexane-1,1'-(3'H)-isobenzofuran]-4-carboxamide (100 mg) produced in Example 51 in N,N-dimethylformamide (3.0 mL) and stirred at 100° C. throughout the night. The reaction solution was diluted with ethyl acetate and washed with a saturated saline solution. The organic layer was dried over sodium sulfate, filtered and concentrated in vacuo. The residue was purified by a silica gel column chromatography (Biotage Column NH, hexane/ethyl acetate=0% to 80%, gradient) and then further purified by a silica gel column chromatography (Biotage Column, chloroform/methanol=0% to 20%, gradient) to give the title compound (35.8 mg, 41%) as a light yellow oily substance.

$^1$HNMR (400 MHz, CDCl$_3$, δ): 1.39-1.50 (2H, m), 1.53-1.63 (4H, m), 1.83-1.95 (2H, m), 2.02-2.16 (4H, m), 2.31-2.56 (8H, m), 2.93-3.03 (1H, m), 3.00 (3H×½, s), 3.14 (3H×½, s), 3.48 (2H×½, t, J=7.1 Hz), 3.57 (2H×½, t, J=7.1 Hz), 7.82 (1H×½, d, J=8.3 Hz), 7.87 (1H×½, d, J=7.8 Hz), 8.33-8.39 (1H, m), 8.50 (1H, s), 8.57-8.61 (1H, m), 8.66-8.70 (1H, m), 9.07-9.12 (1H, m); mass spectrum (ESI): 449.2 (M+H)

The compounds of Examples 58 to 60 can be produced using the corresponding tin reagent as a material by the same method as in Example 57, by a method similar thereto or by combining such methods with a conventional method.

Example 58 trans-5'-(Pyridin-2-yl)-3'-oxo-N-methyl-N-(2-piperidin-1-ylethyl)-spiro[cyclohexane-1,1'-(3'H)-isobenzofuran]-4-carboxamide

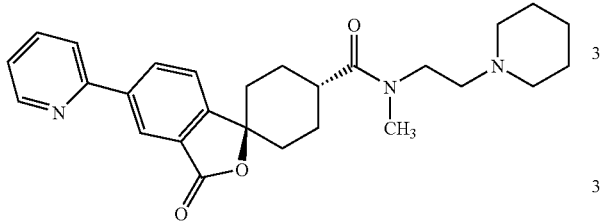

A method according to Example 57 was carried out to produce the title compound using trans-5'-{{(trifluoromethyl)-sulfonyl}oxy}-3'-oxo-N-methyl-N-(2-piperidin-1-ylethyl)-spiro[cyclohexane-1,1'-(3'H)-isobenzofuran]-4-carboxamide produced in Example 51 and 2-(tri-n-butyl tin) pyridine as materials.

$^1$HNMR (400 MHz, CDCl$_3$, δ): 1.39-1.50 (2H, m), 1.53-1.65 (4H, m), 1.80-1.94 (2H, m), 1.99-2.15 (4H, m), 2.28-2.59 (8H, m), 2.91-2.99 (1H, m), 2.99 (3H×½, s), 3.13 (3H×½, s), 3.47 (2H×½, t, J=6.8 Hz), 3.57 (2H×½, t, J=7.1 Hz), 7.27-7.33 (1H, m), 7.71-7.85 (3H, m), 8.35-8.40 (1H, m), 8.40-8.45 (1H, m), 8.68-8.76 (1H, m); mass spectrum (ESI): 448.2 (M+H)

Example 59 trans-5'-(Pyrazin-2-yl)-3'-oxo-N-methyl-N-(2-pyrrolidin-1-ylethyl)-spiro[cyclohexane-1,1'-(3'H)-isobenzofuran]-4-carboxamide

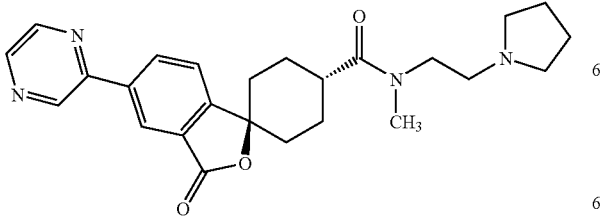

A method according to Example 57 was carried out to produce the title compound using trans-5'-{{(trifluoromethyl)-sulfonyl}-oxy}-3'-oxo-N-methyl-N-(2-pyrrolidin-1-ylethyl)-spiro[cyclohexane-1,1'(3H)-isobenzofuran]-4-carboxamide produced in Example 52 and 2-(tri-n-butyl tin) pyridine as materials.

$^1$HNMR (400 MHz, CDCl$_3$, δ): 1.77-1.95 (6H, m), 2.00-2.16 (4H, m), 2.31-2.43 (2H, m), 2.55-2.78 (6H, m), 2.93-3.00 (1H, m), 3.01 (3H×½, s), 3.15 (3H×½, s), 3.47-3.66 (2H, m), 7.82 (1H×½, d, J=8.3 Hz), 7.86 (1H×½, d, J=8.3 Hz), 8.34-8.39 (1H, m), 8.49-8.51 (1H, m), 8.58-8.60 (1H, m), 8.67-8.69 (1H, m), 9.08-9.10 (1H, m); mass spectrum (ESI): 435.3 (M+H)

Example 60 trans-5'-Pyridin-2-yl-3'-oxo-N-methyl-N-(2-pyrrolidin-1-ylethyl)-spiro[cyclohexane-1,1'-(3'H)-isobenzofuran]-4-carboxamide

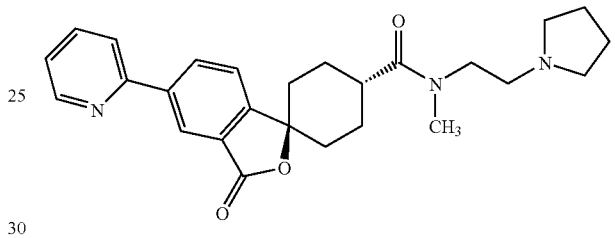

A method according to Example 57 was carried out to produce the title compound using trans-5'-{[(trifluoromethyl)sulfonyl}oxy}-3'-oxo-N-methyl-N-(2-pyrrolidin-1-ylethyl)-spiro[cyclohexane-1,1'-(3H)-isobenzofuran]-4-carboxamide produced in Example 52 and 2-(tri-n-butyl tin) pyridine as materials.

$^1$HNMR (400 MHz, CDCl$_3$, δ): 1.76-1.94 (6H, m), 2.00-2.14 (4H, m), 2.28-2.41 (2H, m), 2.54-2.75 (6H, m), 2.91-3.02 (1H, m), 3.01 (3H×½, s), 3.14 (3H×½, s), 3.51 (2H×½, t, J=7.6 Hz), 3.61 (2H×½, t, J=7.3 Hz), 7.27-7.34 (1H, m), 7.74-7.85 (3H, m), 8.34-8.45 (2H, m), 8.69-8.75 (1H, m); mass spectrum (ESI): 434.3 (M+H)

Example 61 trans-5'-Cyclopropyl-3'-oxo-N-methyl-N-(2-pyrolidin-1-ylethyl)-spiro[cyclohexane-1,1'-(3'H)-isobenzofuran]-4-carboxamide

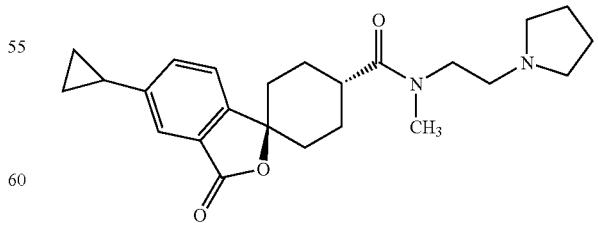

Cyclopropylboronic acid (10.2 mg), palladium acetate (2.2 mg), tricyclohexylphosphine (5.6 mg), potassium phosphate (73.6 mg) and water (0.050 mL) were successively added at room temperature to a solution of trans-5'-{[(trifluoromethyl)-sulfonyl]oxy}-3'-oxo-N-methyl-N-(2-pyrrolidin-1-ylethyl)-spiro[cyclohexane-1,1'-(3'H)-isobenzofuran]-4-carboxamide (50 mg) prepared in Example 52 in toluene (1.0 mL) and stirred at 100° C. throughout the night. The reaction solution was diluted with ethyl acetate and washed with a saturated saline solution. The organic layer was dried over sodium sulfate, filtered and concentrated in vacuo. The residue was purified by a reversed phase HPLC (0.1% TFA acetonitrile:$H_2O$=10% to 70%, gradient) to give the title compound (7.2 mg, 18%) as a colorless oily substance.

$^1$HNMR (400 MHz, $CDCl_3$, δ): 0.72-0.78 (2H, m), 1.01-1.08 (2H, m), 1.73-1.91 (6H, m), 1.94-2.13 (5H, m), 2.16-2.29 (2H, m), 2.52-2.73 (6H, m), 2.85-2.96 (1H, m), 2.99 (3H×½, s), 3.12 (3H×½, s), 3.49 (2H×½, t, J=7.6 Hz), 3.57 (2H×½, t, J=7.3 Hz), 7.36-7.42 (1H, m), 7.51 (1H, s), 7.55 (1H×½, d, J=7.8 Hz), 7.60 (1H×½, d, J=7.8 Hz); mass spectrum (ESI): 397.4 (M+H)

Example 62 trans-5'-Vinyl-3'-oxo-N-methyl-N-(2-pyrrolidin-1-ylethyl)-spiro[cyclohexane-1,1'-(3'H)-isobenzofuran]-4-carboxamide

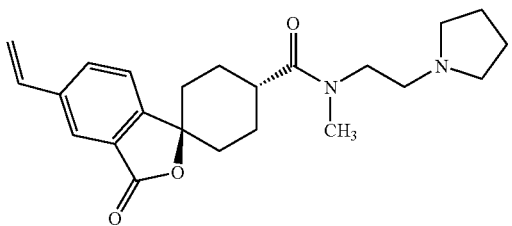

[1,1'-Bis(diphenylphosphino)ferrocene]dichloro palladium (II) (29.0 mg), potassium vinyl trifluoroborate (31.9 mg) and triethylamine (0.028 mL) were successively added at room temperature to a solution of trans-5'-{[(trifluoromethyl)-sulfonyl]oxy}-3'-oxo-N-methyl-N-(2-pyrrolidin-1-ylethyl)-spiro[cyclohexane-1,1'-(3'H)-isobenzofuran]-4-carboxamide (100 mg) prepared in Example 52 in n-propanol (1 mL) and stirred at 100° C. for 3 hours. The reaction solution was diluted with ethyl acetate and washed with a saturated saline solution. The organic layer was dried over sodium sulfate, filtered and concentrated in vacuo. The residue was purified by a silica gel column chromatography (Biotage Column NH, hexane/ethyl acetate=0% to 80%, gradient) to give the title compound (50.2 mg, 66%) as a light yellow oily substance.

$^1$HNMR (400 MHz, $CDCl_3$, δ): 1.74-1.91 (6H, m), 1.98-2.13 (4H, m), 2.21-2.33 (2H, m), 2.52-2.74 (6H, m), 2.87-2.98 (1H, m), 3.00 (3H×½, s), 3.13 (3H×½, s), 3.50 (2H×½, t, J=7.6 Hz), 3.57 (2H×½, t, J=7.3 Hz), 5.37 (1H, d, J=11.2 Hz), 5.85 (1H, d, J=17.6 Hz), 6.78 (1H, dd, J=17.6, 11.2 Hz), 7.58-7.72 (2H, m), 7.90 (1H, s); mass spectrum (ESI): 383.3 (M+H)

Example 63 trans-5'-Ethyl-3'-oxo-N-methyl-N-(2-pyrrolidin-1-ylethyl)-spiro[cyclohexane-1,1'-(3'H)-isobenzofuran]-4-carboxamide

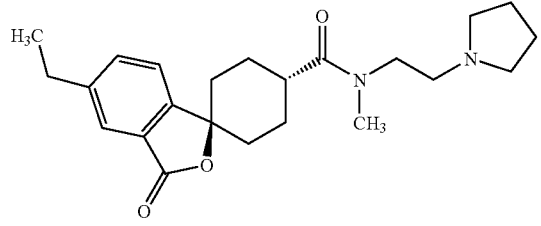

A 10% palladium-carbon (10 mg) as a catalyst was added to a solution of trans-5'-vinyl-3'-oxo-N-methyl-N-(2-pyrrolidin-1-ylethyl)-spiro[cyclohexane-1,1'-(3'H)-isobenzofuran]-4-carboxamide (49.0 mg) prepared in Example 62 in ethanol (5.0 mL) and stirred in a hydrogen atmosphere at room temperature throughout the night. After filtering off the catalyst, the solvent was evaporated in vacuo and the resulting residue was purified by a silica gel column chromatography (Biotage Column, chloroform/methanol=0% to 80%, gradient) to give the title compound (27.8 mg, 57%) as a colorless oily substance.

$^1$HNMR (400 MHz, $CDCl_3$, δ): 1.28 (3H, t, J=7.6 Hz), 1.76-1.92 (6H, m), 1.96-2.11 (4H, m), 2.18-2.29 (2H, m), 2.52-2.80 (8H, m), 2.86-2.96 (1H, m), 3.00 (3H×½, s), 3.14 (3H×½, s), 3.50 (2H×½, t, J=7.3 Hz), 3.60 (2H×½, t, J=7.3 Hz), 7.44-7.51 (1H, m), 7.58 (1H×½, d, J=7.8 Hz), 7.63 (1H×½, d, J=7.8 Hz), 7.70 (1H, s); mass spectrum (ESI): 385.4 (M+H)

Example 64 trans-5'-Ethoxy-3'-oxo-N-methyl-N-(2-pyrrolidin-1-ylethyl)-spiro[cyclohexane-1,1'-(3'H)-isobenzofuran]-4-carboxamide

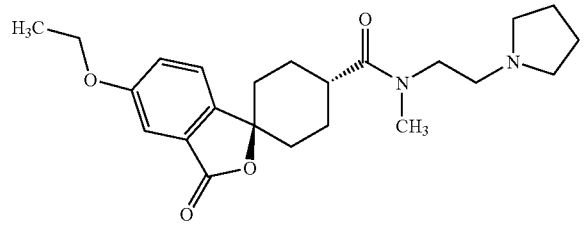

Ethyl iodide (0.022 mL) and cesium carbonate (175 mg) were successively added at room temperature to a solution of trans-5'-hydroxy-3'-oxo-N-methyl-N-(2-pyrrolidin-1-ylethyl)-spiro[cyclohexane-1,1'-(3'H)-isobenzofuran]-4-carboxamide (100 mg) prepared in Example 20 in N,N-dimethylformamide (2 mL) and stirred at 50° C. for 3 hours. The reaction solution was diluted with ethyl acetate and washed with a saturated sodium bicarbonate solution. The organic solvent was dried over sodium sulfate, filtered and concentrated in vacuo. The residue was purified by a silica gel column chromatography (Biotage Column, chloroform/methanol=0% to 5%, gradient) to give the title compound (91.3 mg, 85%) as a colorless oily substance.

$^1$HNMR (400 MHz, $CDCl_3$, δ): 1.44 (3H, t, J=7.1 Hz), 1.75-1.91 (6H, m), 1.97-2.09 (4H, m), 2.15-2.26 (2H, m), 2.53-2.74 (6H, m), 2.85-2.94 (1H, m), 2.99 (3H×½, s), 3.13 (3H×½, s), 3.46-3.53 (2H×½, m), 3.53-3.62 (2H×½, m), 4.08

(2H, q, J=7.1 Hz), 7.16-7.21 (1H, m), 7.28-7.30 (1H, m), 7.57 (1H×½, d, J=8.3 Hz), 7.61 (1H×½, d, J=8.3 Hz); mass spectrum (ESI): 401.3 (M+H)

Example 65 trans-5'-Isopropoxy-3'-oxo-N-methyl-N-(2-pyrrolidin-1-ylethyl)-spiro[cyclohexane-1,1'-(3'H)-isobenzofuran]-4-carboxamide

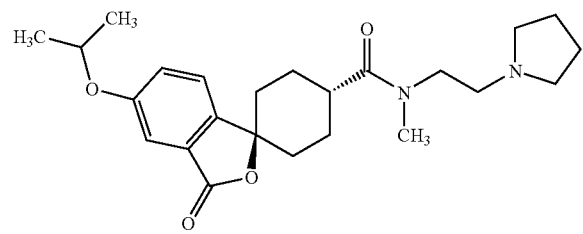

A method according to Example 64 was carried out to produce the title compound using trans-5'-hydroxy-3'-oxo-N-methyl-N-(2-pyrrolidin-1-ylethyl)-spiro[cyclohexane-1,1'-(3H)-iso-benzofuran]-4-carboxamide produced in Example 20 and 2-iodopropane as materials.

¹HNMR (400 MHz, CDCl₃, δ): 1.35 (6H, d, J=5.9 Hz), 1.72-1.92 (6H, m), 1.94-2.11 (4H, m), 2.13-2.25 (2H, m), 2.51-2.71 (6H, m), 2.82-2.94 (1H, m), 2.98 (3H×½, s), 3.12 (3H×½, s), 3.44-3.62 (2H, m), 4.53-4.63 (1H, m), 7.12-7.18 (1H, m), 7.26-7.31 (1H, m), 7.55 (1H×½, d, J=8.3 Hz), 7.60 (1H×½, d, J=8.3 Hz); mass spectrum (ESI): 415.3 (M+H)

Example 66 trans-5'-[2-Fluoro-1-(fluoromethyl)ethoxy]-3'-oxo-N-methyl-N-(2-piperidin-1-ylethyl)-spiro[cyclohexane-1,1'-(3'H)-isobenzofuran]-4-carboxamide

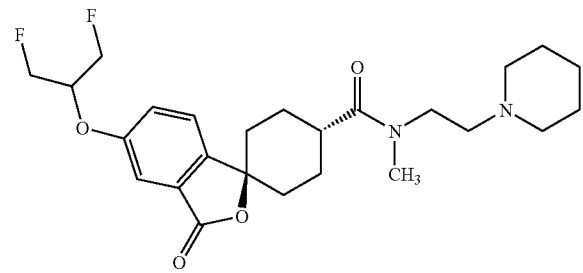

1,3-Difluoropropan-2-ol (0.075 mL) was dissolved in ethyl acetate (2 mL) and then triethylamine (0.12 mL) and methanesulfonyl chloride (0.062 mL) were successively added at room temperature thereto. After the mixture was stirred at room temperature for 10 minutes and the solid separated out therefrom was filtered. The filtrate was concentrated, the residue was dissolved in N-methyl-2-pyrrolidone (2 mL) and then trans-5'-hydroxy-3'-oxo-N-methyl-N-(2-piperidin-1-ylethyl)-spiro[cyclohexane-1,1'-(3'H)-isobenzofuran]-4-carboxamide (200 mg) prepared in Example 23 and cesium carbonate (506 mg) were successively added thereto at room temperature. After the mixture was stirred at 100° C. throughout the night, the reaction solution was diluted with ethyl acetate and washed with a saturated saline solution. The organic layer was dried over sodium sulfate, filtered and concentrated in vacuo. The residue was purified by a silica gel column chromatography (Biotage Column, chloroform/methanol=0% to 20%, gradient) and then further purified by a silica gel column chromatography (Biotage Column NH, hexane/ethyl acetate=0% to 80%, gradient) to give the title compound (36.5 mg, 15%) as a colorless oily substance.

¹HNMR (400 MHz, CDCl₃, δ): 1.38-1.50 (2H, m), 1.52-1.64 (4H, m), 1.78-1.92 (2H, m), 1.96-2.11 (4H, m), 2.17-2.30 (2H, m), 2.38-2.53 (6H, m), 2.85-2.97 (1H, m), 2.98 (3H×½, s), 3.12 (3H×½, s), 3.46 (2H×½, t, J=7.1 Hz), 3.55 (2H×½, t, J=7.1 Hz), 4.57-4.84 (5H, m), 7.26-7.33 (1H, m), 7.39 (1H, s), 7.61 (1H×½, d, J=8.3 Hz), 7.66 (1H×½, d, J=8.8 Hz); mass spectrum (ESI): 465.3 (M+H)

Example 67 trans-5'-[2-Fluoro-1-(fluoromethyl)ethoxy]-3'-oxo-N-methyl-N-(2-pyrrolidin-1-ylethyl)-spiro[cyclohexane-1,1'-(3'H)-isobenzofuran]-4-carboxamide

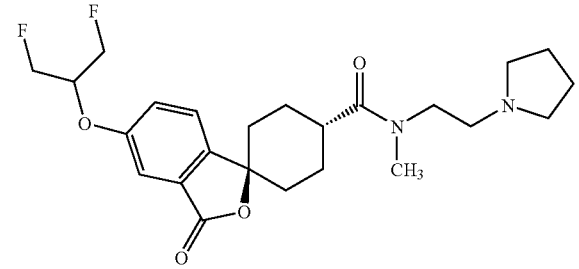

A method according to Example 66 was carried out to produce the title compound using trans-5'-hydroxy-3'-oxo-N-methyl-N-(2-pyrrolidin-1-ylethyl)-spiro[cyclohexane-1,1' (3H)-iso-benzofuran]-4-carboxamide produced in Example 20 and 1,3-difluoropropan-2-ol as materials.

¹HNMR (400 MHz, CDCl₃, δ): 1.73-1.90 (6H, m), 1.97-2.11 (4H, m), 2.17-2.30 (2H, m), 2.51-2.72 (6H, m), 2.86-2.98 (1H, m), 2.99 (3H×½, s), 3.12 (3H×½, s), 3.49 (2H×½, t, J=7.6 Hz), 3.57 (2H×½, t, J=7.3 Hz), 4.56-4.85 (5H, m), 7.26-7.34 (1H, m), 7.36-7.41 (1H, m), 7.61 (1H×½, d, J=8.3 Hz), 7.65 (1H×½, d, J=8.3 Hz); mass spectrum (ESI): 451.4 (M+H)

Example 68 trans-5'-(Pyridin-2-yloxy)-3'-oxo-N-methyl-N-(2-piperidin-1-ylethyl)-spiro[cyclohexane-1,1'-(3'H)-iso-benzofuran]-4-carboxamide

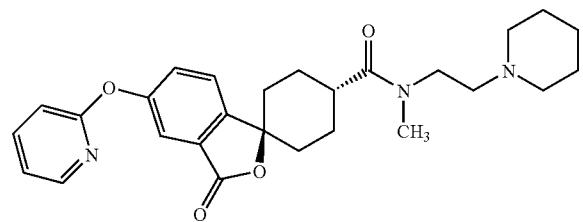

2-Fluoropyridine (377 mg) and cesium carbonate (759 mg) were successively added at room temperature to a solution of trans-5'-hydroxy-3'-oxo-N-methyl-N-(2-piperidin-1-yl-ethyl)-spiro[cyclohexane-1,1'-(3'H)-isobenzofuran]-4-carboxamide (300 mg) prepared in Example 23 in N-methyl-2-pyrrolidone (6.0 mL) and stirred at 120° C. for 11 hours. The reaction solution was diluted with ethyl acetate and washed with water. The organic layer was dried over sodium sulfate, filtered and concentrated in vacuo. The residue was purified by a silica gel column chromatography (Biotage Column, chloroform/methanol=0% to 20%, gradient) to give the title compound (185 mg, 51%) as a light yellow oily substance.

$^1$HNMR (400 MHz, CDCl$_3$, δ): 1.37-1.50 (2H, m), 1.51-1.64 (4H, m), 1.81-1.95 (2H, m), 1.97-2.11 (4H, m), 2.24-2.35 (2H, m), 2.39-2.54 (6H, m), 2.88-2.98 (1H, m), 2.98 (3H×½, s), 3.12 (3H×½, s), 3.46 (2H×½, t, J=7.1 Hz), 3.55 (2H×½, t, J=7.1 Hz), 6.98-7.09 (2H, m), 7.40-7.47 (1H, m), 7.61 (1H, s), 7.66-7.79 (2H, m), 8.16-8.22 (1H, m); mass spectrum (ESI): 464.3 (M+H)

Example 69 trans-5'-(Pyrimidin-2-yloxy)-3'-oxo-N-methyl-N-(2-piperidin-1-ylethyl)-spiro[cyclohexane-1,1'-(3'H)-isobenzofuran]-4-carboxamide

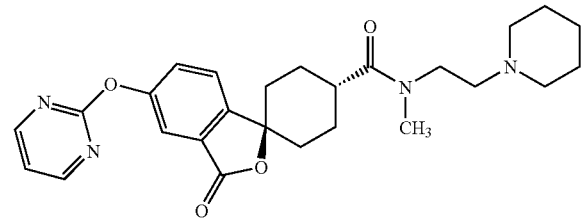

A method according to Example 68 was carried out to produce the title compound using trans-5'-hydroxy-3'-oxo-N-methyl-N-(2-piperidin-1-ylethyl)-spiro[cyclohexane-1,1'-(3H)-iso-benzofuran]-4-carboxamide produced in Example 23 and 2-chloropyrimidine as materials.

$^1$HNMR (400 MHz, CDCl$_3$, δ): 1.38-1.51 (2H, m), 1.53-1.63 (4H, m), 1.82-1.97 (2H, m), 1.99-2.11 (4H, m), 2.26-2.37 (2H, m), 2.38-2.55 (6H, m), 2.88-2.98 (1H, m), 2.98 (3H×½, s), 3.13 (3H×½, s), 3.47 (2H×½, t, J=7.1 Hz), 3.55 (2H×½, t, J=7.1 Hz), 7.11 (1H, t, J=4.9 Hz), 7.46-7.52 (1H, m), 7.69-7.80 (2H, m), 8.57-8.62 (2H, m); mass spectrum (ESI): 465.3 (M+H)

Example 70 trans-5'-(Pyrazin-2-yloxy)-3'-oxo-N-methyl-N-(2-piperidin-1-ylethyl]-spiro[cyclohexane-1,1'-(3'H)-iso-benzofuran]-4-carboxamide

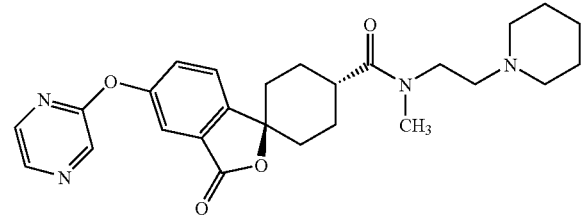

A method according to Example 68 was carried out to produce the title compound using trans-5'-hydroxy-3'-oxo-N-methyl-N-(2-piperidin-1-ylethyl)-spiro[cyclohexane-1,1'-(3H)-iso-benzofuran]-4-carboxamide produced in Example 23 and 2-chloropyrazine as materials.

$^1$HNMR (400 MHz, CDCl$_3$, δ): 1.39-1.51 (2H, m), 1.53-1.64 (4H, m), 1.82-1.95 (2H, m), 2.00-2.12 (4H, m), 2.25-2.37 (2H, m), 2.40-2.54 (6H, m), 2.90-2.98 (1H, m), 2.99 (3H×½, s), 3.13 (3H×½, s), 3.47 (2H×½, t, J=6.8 Hz), 3.56 (2H×½, t, J=7.1 Hz), 7.45 (1H×½, t, J=2.2 Hz), 7.47 (1H×½, t, J=2.2 Hz), 7.65-7.69 (1H, m), 7.74 (1H×½, d, J=8.3 Hz), 7.78 (1H×½, d, J=8.3 Hz), 8.09-8.14 (1H, m), 8.32-8.36 (1H, m), 8.49-8.53 (1H, m); mass spectrum (ESI): 465.3 (M+H)

Example 71 trans-5'-(Pyrimidin-2-yloxy)-3'-oxo-N-methyl-N-(2-pyrrolidin-1-ylethyl)-spiro[cyclohexane-1,1'-(3'H)-isobenzofuran]-4-carboxamide

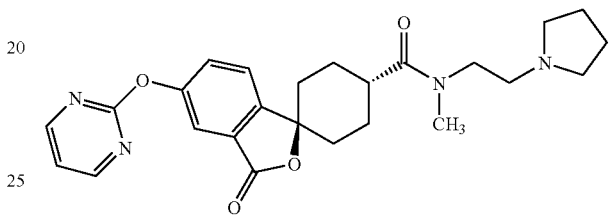

A method according to Example 68 was carried out to produce the title compound using trans-5'-hydroxy-3'-oxo-N-methyl-N-(2-pyrrolidin-1-ylethyl)-spiro[cyclohexane-1,1'-(3H)-iso-benzofuran]-4-carboxamide produced in Example 20 and 2-chloropyrimidine as materials.

$^1$HNMR (400 MHz, CDCl$_3$, δ): 1.76-1.96 (6H, m), 1.99-2.39 (6H, m), 2.54-2.75 (6H, m), 2.88-2.99 (1H, m), 3.00 (3H×½, s), 3.14 (3H×½, s), 3.51 (2H×½, t, J=7.3 Hz), 3.60 (2H×½, t, J=7.3 Hz), 7.11 (1H, t, J=4.9 Hz), 7.46-7.53 (1H, m), 7.69-7.81 (2H, m), 8.60 (2H, d, J=4.9 Hz); mass spectrum (ESI): 451.2 (M+H)

Example 72 trans-5'-[(4-Methoxypyrimidin-2-yl)oxy]-3'-oxo-N-methyl-N-(2-pyrrolidin-1-ylethyl)-spiro[cyclohexane-1,1'-(3'H)-isobenzofuran]-4-carboxamide

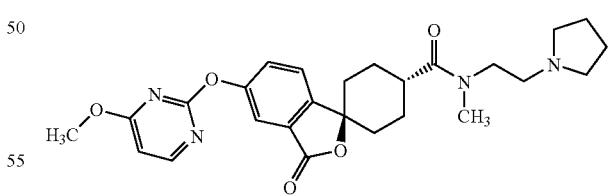

A method according to Example 68 was carried out to produce the title compound using trans-5'-hydroxy-3'-oxo-N-methyl-N-(2-pyrrolidin-1-ylethyl)-spiro[cyclohexane-1,1'-(3H)-iso-benzofuran]-4-carboxamide produced in Example 20 and 2-chloro-2-methoxypyrimidine as materials.

$^1$HNMR (400 MHz, CDCl$_3$, δ): 1.74-2.11 (10H, m), 2.24-2.35 (2H, m), 2.54-2.72 (6H, m), 2.86-2.99 (1H, m), 3.00 (3H×½, s), 3.13 (3H×½, s), 3.51 (2H×½, t, J=7.3 Hz), 3.58 (2H×½, t, J=7.3 Hz), 3.98 (3H, s), 6.51 (1H, d, J=5.4 Hz), 7.47-7.52 (1H, m), 7.70-7.78 (2H, m), 8.19 (1H, d, J=5.4 Hz); mass spectrum (ESI): 481.2 (M+H)

Example 73 trans-5'-(Pyrazin-2-yloxy)-3'-oxo-N-methyl-N-(2-pyrrolidin-1-ylethyl)-spiro[cyclohexane-1,1'-(3'H)-iso-benzofuran]-4-carboxamide

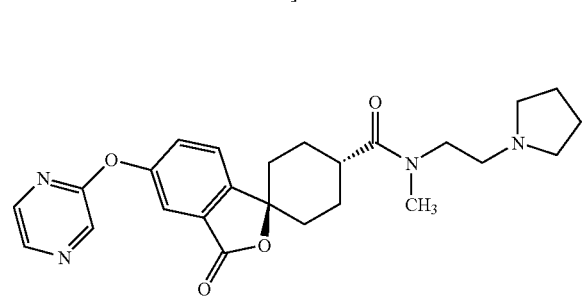

A method according to Example 68 was carried out to produce the title compound using trans-5'-hydroxy-3'-oxo-N-methyl-N-(2-pyrrolidin-1-ylethyl)-spiro[cyclohexane-1,1' (3H)-iso-benzofuran]-4-carboxamide produced in Example 20 and 2-chloropyrazine as materials.

$^1$HNMR (400 MHz, CDCl$_3$, δ): 1.72-1.94 (6H, m), 1.97-2.13 (4H, m), 2.25-2.37 (2H, m), 2.53-2.72 (6H, m), 2.89-2.99 (1H, m), 3.00 (3H×½, s), 3.13 (3H×½, s), 3.51 (2H×½, t, J=7.3 Hz), 3.57 (2H×½, t, J=7.3 Hz), 7.43-7.49 (1H, m), 7.65-7.69 (1H, m), 7.74 (1H×½, d, J=8.3 Hz), 7.78 (1H×½, d, J=8.3 Hz), 8.09-8.13 (1H, m), 8.32-8.35 (1H, m), 8.50-8.53 (1H, m); mass spectrum (ESI): 451.2 (M+H)

Example 74 trans-5'-[(2-Cyanopyrimidin-5-yl)oxy]-3'-oxo-N-methyl-N-(2-pyrrolidin-1-ylethyl)-spiro[cyclohexane-1,1'-(3'H)-isobenzofuran]-4-carboxamide

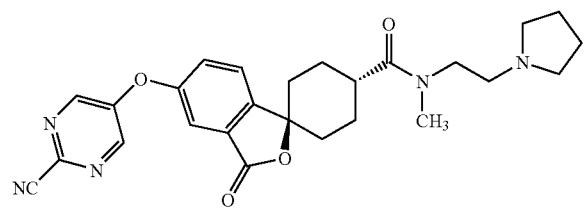

A method according to Example 68 was carried out to produce the title compound using trans-5'-hydroxy-3'-oxo-N-methyl-N-(2-pyrrolidin-1-ylethyl)-spiro[cyclohexane-1,1' (3H)-iso-benzofuran]-4-carboxamide produced in Example 20 and 5-bromopyrimidine-2-carbonitrile as materials.

$^1$HNMR (400 MHz, CDCl$_3$, δ): 1.73-1.94 (6H, m), 1.98-2.15 (4H, m), 2.28-2.42 (2H, m), 2.54-2.73 (6H, m), 2.93-3.01 (1H, m), 3.00 (3H×½, s), 3.14 (3H×½, s), 3.51 (2H×½, t, J=7.3 Hz), 3.58 (2H×½, t, J=7.3 Hz), 7.42 (1H×½, t, J=2.4 Hz), 7.44 (1H×½, t, J=2.4 Hz), 7.56-7.58 (1H, m), 7.79 (1H×½, d, J=8.3 Hz), 7.84 (1H×½, d, J=8.3 Hz), 8.55 (2H, s); mass spectrum (ESI): 476.2 (M+H)

Example 75 trans-5'-[(5-Fluoropyrimidin-2-yl)oxy]-3'-oxo-N-methyl-N-(2-pyrrolidin-1-ylethyl)-spiro[cyclohexane-1,1'-(3'H)-isobenzofuran]-4-carboxamide

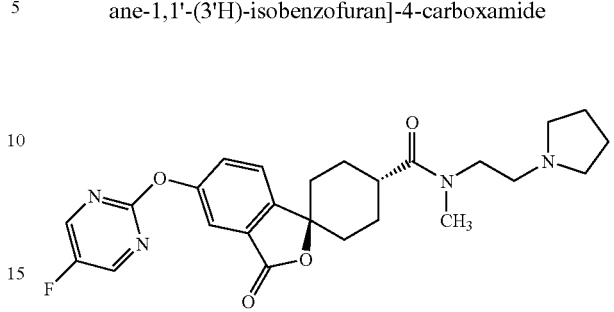

A method according to Example 68 was carried out to produce the title compound using trans-5'-hydroxy-3'-oxo-N-methyl-N-(2-pyrrolidin-1-ylethyl)-spiro[cyclohexane-1,1'-(3H)-iso-benzofuran]-4-carboxamide produced in Example 20 and 2-chloro-5-fluoropyrimidine as materials.

$^1$HNMR (400 MHz, CDCl$_3$, δ): 1.75-1.94 (6H, m), 1.99-2.12 (4H, m), 2.24-2.38 (2H, m), 2.54-2.75 (6H, m), 2.89-2.99 (1H, m), 3.00 (3H×½, s), 3.14 (3H×½, s), 3.51 (2H×½, t, J=7.6 Hz), 3.60 (2H×½, t, J=7.3 Hz), 7.44-7.50 (1H, m), 7.67-7.70 (1H, m), 7.73 (1H×½, d, J=8.3 Hz), 7.78 (1H×½, d, J=8.3 Hz), 8.44 (2H, s); mass spectrum (ESI): 469.3 (M+H)

Example 76 trans-5'-(Piperidin-4-yloxy)-3'-oxo-N-methyl-N-(2-piperidin-1-ylethyl)-spiro[cyclohexane-1,1'-(3'H)-isobenzofuran]-4-carboxamide

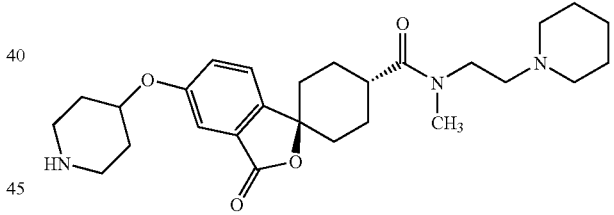

Triethylamine (0.29 mL) and methanesulfonyl chloride (0.20 mL) were successively added at room temperature to a solution of tert-butyl 4-hydroxypiperidine-1-carboxylate (391 mg) in ethyl acetate (5 mL). After the mixture was stirred at room temperature for 15 minutes, the solid separated out therefrom was filtered. The filtrate was concentrated, the resulting residue was dissolved in N,N-dimethylformamide (5.0 mL) and then trans-5'-hydroxy-3'-oxo-N-methyl-N-(2-piperidin-1-ylethyl)-spiro[cyclohexane-1,1'-(3'H)-iso-benzofuran]-4-carboxamide (500 mg) produced in Example 23 and potassium carbonate (536 mg) were successively added thereto. After the reaction solution was stirred at 80° C. throughout one night, water was added to the reaction solution followed by extracting with ethyl acetate. The organic layer was dried over sodium sulfate, filtered and concentrated in vacuo. The residue was purified by a silica gel column chromatography (Biotage Column, chloroform/methanol=0% to 20%, gradient). The resulting compound (512 mg) was dissolved in a 4N hydrogen chloride solution in ethyl acetate (10 mL) and the reaction solution was stirred at room temperature for 1 hour. The reaction solution was concentrated in vacuo to give a dihydrochloride (490 mg, 70%) of the title compound. The resulting dihydrochloride (20 mg) of the title compound was purified by a preparative thin layer chromatography (chloroform/methanol=10/1) to give the title compound (8 mg, 47%) as a light yellow oily substance.

$^1$HNMR (400 MHz, CDCl$_3$, δ): 1.38-1.49 (2H, m), 1.52-1.62 (4H, m), 1.63-1.76 (2H, m), 1.81-1.94 (4H, m), 1.96-2.13 (4H, m), 2.16-2.27 (2H, m), 2.38-2.53 (6H, m), 2.70-2.82 (2H, m), 2.85-2.96 (1H, m), 2.98 (3H×½, s), 3.10-3.21 (2H, m), 3.12 (3H×½, s), 3.46 (2H×½, t, J=7.3 Hz), 3.54 (2H×½, t, J=7.1 Hz), 4.37-4.50 (1H, m), 7.17-7.23 (1H, m), 7.29-7.33 (1H, m), 7.57 (1H×½, d, J=8.3 Hz), 7.62 (1H×½, d, J=8.3 Hz); mass spectrum (ESI): 470.2 (M+H)

Example 77 trans-5'-[(1-Acetylpiperidin-4-yl)oxy]-3'-oxo-N-methyl-N-(2-piperidin-1-ylethyl)-spiro[cyclohexane-1,1'-(3'H)-isobenzofuran]-4-carboxamide

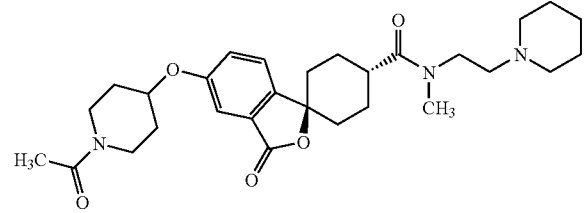

Acetic anhydride (0.50 mL) was added to a solution of trans-5'-(piperidin-4-yloxy)-3'-oxo-N-methyl-N-(2-piperidin-1-ylethyl)-spiro[cyclohexane-1,1'-(3'H)-isobenzofuran]-4-carboxamide dihydrochloride (148 mg) produced in Example 76 in pyridine (0.50 mL) and the reaction solution was stirred at room temperature for 1 hour. Toluene was added to the reaction solution, the solvent was evaporated in vacuo and the resulting residue was purified by a silica gel column chromatography (Biotage Column, chloroform/methanol=0% to 10%, gradient) to give the title compound (79.6 mg, 57%) as a colorless oily substance.

$^1$HNMR (400 MHz, CDCl$_3$, δ): 1.39-1.51 (2H, m), 1.52-1.65 (4H, m), 1.73-2.09 (10H, m), 2.13 (3H, s), 2.16-2.27 (2H, m), 2.37-2.58 (6H, m), 2.86-2.97 (1H, m), 2.98 (3H×½, s), 3.12 (3H×½, s), 3.33-3.87 (6H, m), 4.55-4.65 (1H, m), 7.17-7.23 (1H, m), 7.29-7.33 (1H, m), 7.59 (1H×½, d, J=8.3 Hz), 7.64 (1H×½, d, J=8.3 Hz); mass spectrum (ESI): 512.3 (M+H)

Example 78 trans-5'-[(1-Acetylpyrrolidin-3-yl)oxy]-3'-oxo-N-methyl-N-(2-piperidin-1-ylethyl)-spiro[cyclohexane-1,1'-(3'H)-isobenzofuran]-4-carboxamide

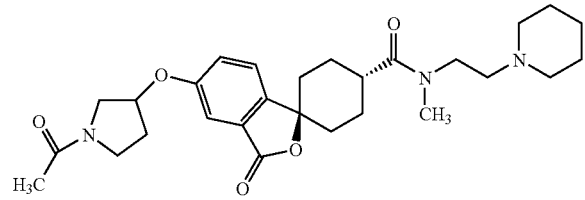

A method according to Examples 76 and 77 was carried out to produce the title compound using trans-5'-hydroxy-3'-oxo-N-methyl-N-(2-piperidin-1-ylethyl)-spiro[cyclohexane-1,1'-(3H)-isobenzofuran]-4-carboxamide produced in Example 23 and tert-butyl 2-hydroxypyrrolidine-1-carboxylate as materials.

$^1$HNMR (400 MHz, CDCl$_3$, δ): 1.38-1.65 (6H, m), 1.75-2.38 (10H, m), 2.06 (3H×½, s), 2.10 (3H×½, s), 2.38-2.55 (6H, m), 2.85-2.97 (1H, m), 2.98 (3H×½, s), 3.12 (3H×½, s), 3.39-3.96 (6H, m), 4.95-5.08 (1H, m), 7.14-7.22 (1H, m), 7.24-7.30 (1H, m), 7.55-7.70 (1H, m); mass spectrum (ESI): 498.4 (M+H)

Example 79 trans-5'-[(1-Acetylpiperidin-4-yl)oxy]-3'-oxo-N-methyl-N-(2-pyrrolidin-1-ylethyl)-spiro[cyclohexane-1,1'-(3'H)-isobenzofuran]-4-carboxamide

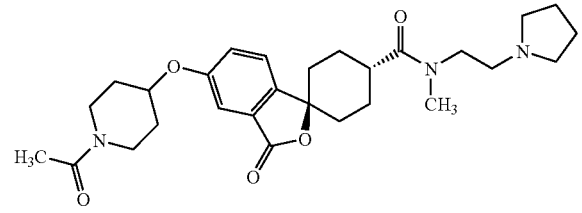

A method according to Examples 76 and 77 was carried out to produce the title compound using trans-5'-hydroxy-3'-oxo-N-methyl-N-(2-pyrrolidin-1-ylethyl)-spiro[cyclohexane-1,1'(3H)-isobenzofuran]-4-carboxamide produced in Example 20 and tert-butyl 4-hydroxypiperidine-1-carboxylate as materials.

$^1$HNMR (400 MHz, CDCl$_3$, δ): 1.74-2.10 (14H, m), 2.13 (3H, s), 2.17-2.29 (2H, m), 2.54-2.71 (6H, m), 2.86-2.97 (1H, m), 2.99 (3H×½, s), 3.13 (3H×½, s), 3.38-3.86 (6H, m), 4.56-4.63 (1H, m), 7.19 (1H×½, t, J=2.4 Hz), 7.22 (1H×½, t, J=2.4 Hz), 7.29-7.33 (1H, m), 7.59 (1H×½, d, J=8.3 Hz), 7.64 (1H×½, d, J=8.3 Hz); mass spectrum (ESI): 498.3 (M+H)

Example 80 trans-5'-[(1-Acetylpyrrolidin-3-yl)oxy]-3'-oxo-N-methyl-N-(2-pyrrolidin-1-ylethyl)-spiro[cyclohexane-1,1'-(3'H)-isobenzofuran]-4-carboxamide

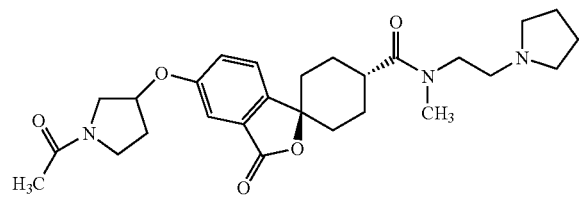

A method according to Examples 76 and 77 was carried out to produce the title compound using trans-5'-hydroxy-3'-oxo-N-methyl-N-(2-pyrrolidin-1-ylethyl)-spiro[cyclohexane-1,1'(3H)-isobenzofuran]-4-carboxamide produced in Example 20 and tert-butyl 2-hydroxypyrrolidine-1-carboxylate as materials.

$^1$HNMR (400 MHz, CDCl$_3$, δ): 1.76-1.91 (6H, m), 1.97-2.38 (8H, m), 2.06 (3H×½, s), 2.10 (3H×½, s), 2.52-2.73 (6H, m), 2.85-2.97 (1H, m), 2.99 (3H×½, s), 3.13 (3H×½, s), 3.46-3.89 (6H, m), 4.96-5.06 (1H, m), 7.13-7.22 (1H, m), 7.24-7.29 (1H, m), 7.56-7.68 (1H, m); mass spectrum (ESI): 484.4 (M+H)

Example 81 trans-5'-4-{[1-(Diphenylmethyl)azetidin-3-yl]oxy}-3'-oxo-N-methyl-N-(2-piperidin-1-ylethyl)-spiro[cyclohexane-1,1'-(3'H)-isobenzofuran]-4-carboxamide

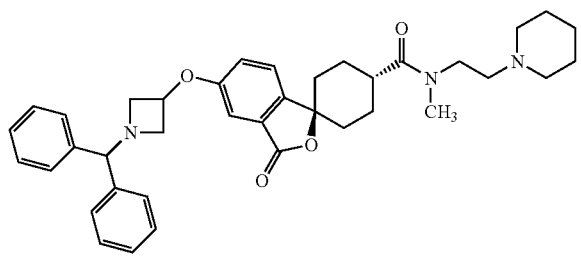

1-(Diphenylmethyl)azetidin-3-ol (556 mg) was dissolved in ethyl acetate (10 mL) and triethylamine (0.35 mL) and methanesulfonyl chloride (0.19 mL) were successively added at room temperature thereto. After the mixture was stirred at room temperature for 10 minutes, the solid separated out therefrom was filtered. The filtrate was concentrated, the resulting residue was dissolved in N-methyl-2-pyrrolidone (10 mL) and then trans-5'-hydroxy-3'-oxo-N-methyl-N-(2-piperidin-1-ylethyl)-spiro[cyclohexane-1,1'-(3'H)-isobenzofuran]-4-carboxamide (406 mg) produced in Example 23 and cesium carbonate (1.51 g) were successively added thereto. After the mixture was stirred at 80° C. throughout the night, the reaction solution was diluted with ethyl acetate and washed with a saturated saline solution. The organic layer was dried over sodium sulfate, filtered and concentrated in vacuo. The residue was purified by a silica gel column chromatography (Biotage Column NH, hexane/ethyl acetate=0% to 80%, gradient) to give the title compound (701 mg, 75%) as a colorless oily substance.

$^1$HNMR (400 MHz, CDCl$_3$, δ): 1.36-1.48 (2H, m), 1.51-1.63 (4H, m), 1.75-1.89 (2H, m), 1.95-2.06 (4H, m), 2.13-2.25 (2H, m), 2.36-2.52 (6H, m), 2.84-2.92 (2H, m), 2.97 (3H×½, s), 3.08-3.17 (1H, m), 3.10 (3H×½, s), 3.44 (1H, t, J=7.1 Hz), 3.49-3.58 (2H, m), 3.69-3.79 (2H, m), 4.77-4.89 (1H, m), 7.07 (1H, brs), 7.09-7.14 (1H, m), 7.15-7.46 (10H, m), 7.52-7.62 (1H, m)

Example 82 trans-5'-(Azetidin-3-yloxy)-3'-oxo-N-methyl-N-(2-piperidin-1-ylethyl)-spiro[cyclohexane-1,1'-(3'H)-isobenzofuran]-4-carboxamide

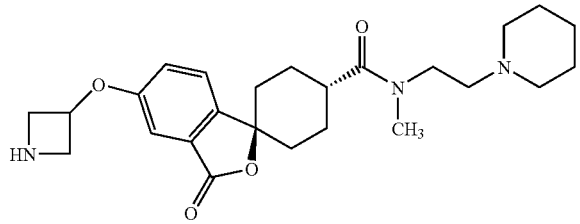

A 20% by weight palladium hydroxide catalyst (200 mg) was added to a solution of trans-5'-4-{[1-(diphenylmethyl)-azetidin-3-yl]oxy}-3'-oxo-N-methyl-N-(2-piperidin-1-ylethyl)-spiro[cyclohexane-1,1'-(3'H)-isobenzofuran]-4-carboxamide (501 mg) produced in Example 81 in ethanol (5.0 mL) and stirred in a 60 psi hydrogen atmosphere at room temperature throughout the night. After the catalyst was filtered, the solvent was evaporated in vacuo and the resulting residue was purified by a silica gel column chromatography (Biotage Column NH, hexane/ethyl acetate=0% to 80%, gradient) to give the title compound (319 mg, 88%) as a light yellow oily substance.

$^1$HNMR (400 MHz, CDCl$_3$, δ): 1.39-1.49 (2H, m), 1.53-1.62 (4H, m), 1.79-1.90 (2H, m), 1.98-2.10 (4H, m), 2.15-2.27 (2H, m), 2.38-2.52 (6H, m), 2.85-2.96 (1H, m), 2.98 (3H×½, s), 3.11 (3H×½, s), 3.45 (2H×½, t, J=7.1 Hz), 3.54 (2H×½, t, J=7.1 Hz), 3.75-3.83 (2H, m), 3.94-4.02 (2H, m), 4.99-5.07 (1H, m), 7.05-7.08 (1H, m), 7.11-7.16 (1H, m), 7.59 (1H×½, d, J=8.8 Hz), 7.64 (1H×½, d, J=8.3 Hz); mass spectrum (ESI): 442.2 (M+H)

Example 83 trans-5'-[(1-Acetylazetidin-3-yl)oxy]-3'-oxo-N-methyl-N-(2-piperidin-1-ylethyl)-spiro[cyclohexane-1,1'-(3'H)-isobenzofuran]-4-carboxamide

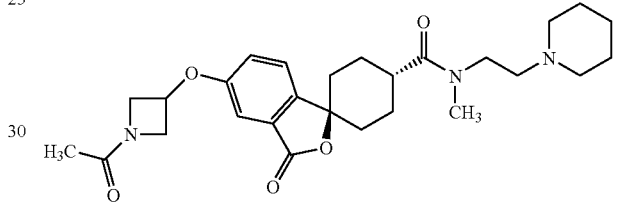

A method according to Example 77 was carried out using trans-5'-(Azetidin-3-yloxy)-3'-oxo-N-methyl-N-(2-piperidin-1-ylethyl)-spiro[cyclohexane-1,1'-(3'H)-isobenzofuran]-4-carboxamide produced in Example 82 as materials to produce the title compound.

$^1$HNMR (400 MHz, CDCl$_3$, δ): 1.38-1.51 (2H, m), 1.51-1.65 (4H, m), 1.78-1.91 (2H, m), 1.92 (3H, s), 1.97-2.13 (4H, m), 2.16-2.30 (2H, m), 2.38-2.56 (6H, m), 2.85-2.97 (1H, m), 2.98 (3H×½, s), 3.12 (3H×½, s), 3.46 (2H×½, t, J=7.1 Hz), 3.55 (2H×½, t, J=7.1 Hz), 4.04-4.12 (2H×½, m), 4.14-4.21 (2H×½, m), 4.38-4.46 (2H×½, m), 4.51-4.60 (2H×½, m), 4.93-5.04 (1H, m), 7.03-7.08 (1H, m), 7.13-7.19 (1H, m), 7.62 (1H×½, d, J=8.8 Hz), 7.68 (1H×½, d, J=8.3 Hz); mass spectrum (ESI): 484.3 (M+H)

Example 84 trans-5'-[(1-Methylsulfonyl)piperidin-4-yloxy]-3'-oxo-N-methyl-N-(2-piperidin-1-ylethyl)-spiro[cyclohexane-1,1'-(3'H)-isobenzofuran]-4-carboxamide

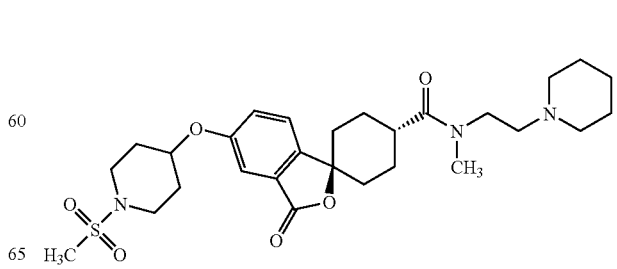

Triethylamine (0.027 mL) and methanesulfonyl chloride (0.012 mL) were successively added to a solution of trans-5'-(piperidin-4-yloxy)-3'-oxo-N-methyl-N-(2-piperidin-1-yl-ethyl)-spiro[cyclohexane-1,1'-(3'H)-isobenzofuran]-4-carboxamide dihydrochloride (59.7 mg) produced in Example 76 in ethyl acetate (3.0 mL) and stirred at room temperature throughout the night. After the reaction solution was diluted with ethyl acetate, it was washed with a saturated saline solution. The organic layer was dried over sodium sulfate, filtered and concentrated in vacuo. The resulting residue was purified by a preparative thin layer chromatography (chloroform/methanol=10/1) to give 17.0 mg (28%) of the title compound as a colorless oily substance.

$^1$HNMR (400 MHz, CDCl$_3$, δ): 1.40-1.50 (2H, m), 1.54-1.66 (4H, m), 1.79-1.92 (2H, m), 1.95-2.13 (8H, m), 2.15-2.30 (2H, m), 2.38-2.60 (6H, m), 2.83 (3H, s), 2.86-2.96 (1H, m), 2.98 (3H×½, s), 3.12 (3H×½, s), 3.32-3.42 (4H, m), 3.46 (2H×½, t, J=7.1 Hz), 3.57 (2H×½, t, J=7.1 Hz), 4.54-4.64 (1H, m), 7.16-7.24 (1H, m), 7.28-7.34 (1H, m), 7.60 (1H×½, d, J=8.3 Hz), 7.65 (1H×½, d, J=8.3 Hz); mass spectrum (ESI): 548.3 (M+H)

Example 85 trans-5'-[(1-Methylsulfonyl)pyrrolidin-3-yloxy]-3'-oxo-N-methyl-N-(2-piperidin-1-ylethyl]-spiro[cyclohexane-1,1'-(3'H)-isobenzofuran]-4-carboxamide

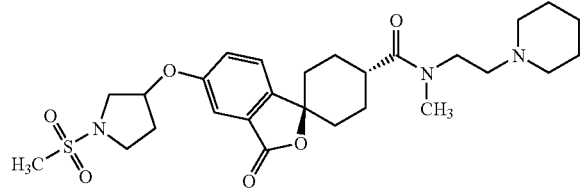

A method according to Examples 76 and 84 was carried out using trans-5'-hydroxy-3'-oxo-N-methyl-N-(2-piperidin-1-ylethyl)-spiro[cyclohexane-1,1'-(3'H)-isobenzofuran]-4-carboxamide produced in Example 23 and tert-butyl 2-hydroxy-pyrrolidine-1-carboxylate as materials to produce the title compound.

$^1$HNMR (400 MHz, CDCl$_3$, δ): 1.35-1.74 (6H, m), 1.75-1.94 (2H, m), 1.95-2.13 (4H, m), 2.14-2.37 (4H, m), 2.37-2.56 (6H, m), 2.86 (3H, s), 2.87-2.96 (1H, m), 2.98 (3H×½, s), 3.12 (3H×½, s), 3.40-3.76 (6H, m), 4.96-5.03 (1H, m), 7.14 (1H×½, t, J=2.3 Hz), 7.16 (1H×½, t, J=2.3 Hz), 7.23-7.28 (1H, m), 7.61 (1H×½, d, J=8.3 Hz), 7.66 (1H×½, d, J=8.3 Hz); mass spectrum (ESI): 534.3 (M+H)

Example 86 trans-5'-{[1-(Methylsulfonyl)pyrrolidin-3-yl]oxy}-3'-oxo-N-methyl-N-(2-pyrrolidin-1-ylethyl)-spiro[cyclohexane-1,1'-(3'H)-isobenzofuran]-4-carboxamide

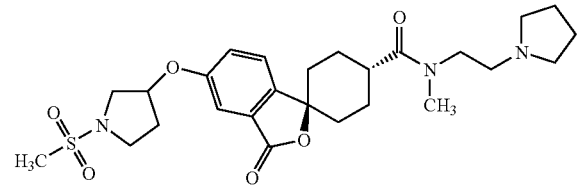

A method according to Examples 76 and 84 was carried out using trans-5'-hydroxy-3'-oxo-N-methyl-N-(2-pyrrolidin-1-ylethyl)-spiro[cyclohexane-1,1'-(3'H)-isobenzofuran]-4-carboxamide produced in Example 20 and tert-butyl 2-hydroxy-pyrrolidine-1-carboxylate as materials to produce the title compound.

$^1$HNMR (400 MHz, CDCl$_3$, δ): 1.78-1.90 (4H, m), 1.98-2.11 (6H, m), 2.19-2.36 (4H, m), 2.54-2.72 (6H, m), 2.86 (3H×½, s), 2.86-2.98 (1H, m), 2.87 (3H×½, s), 2.99 (3H×½, s), 3.13 (3H×½, s), 3.42-3.73 (6H, m), 4.96-5.03 (1H, m), 7.12-7.19 (1H, m), 7.23-7.27 (1H, m), 7.61 (1H×½, d, J=8.8 Hz), 7.66 (1H×½, d, J=8.8 Hz); mass spectrum (ESI): 520.4 (M+H)

Example 87 trans-5'-{[1-(Methylsulfonyl)azetidin-3-yl]oxy}-3'-oxo-N-methyl-N-(2-piperidin-1-ylethyl)-spiro[cyclohexane-1,1'-(3'H)-isobenzofuran]-4-carboxamide

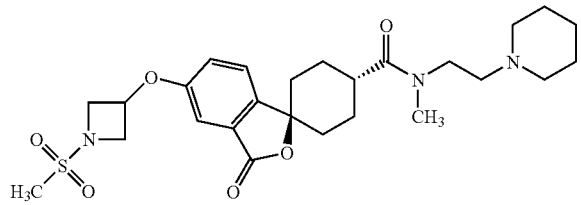

A method according to Example 84 was carried out using trans-5'-(azetidin-3-yloxy)-3'-oxo-N-methyl-N-(2-piperidin-1-ylethyl)-spiro[cyclohexane-1,1'-(3'H)-isobenzofuran]-4-carboxamide produced in Example 82 as a material to produce the title compound.

$^1$HNMR (400 MHz, CDCl$_3$, δ): 1.37-1.50 (2H, m), 1.51-1.64 (4H, m), 1.76-1.91 (2H, m), 1.95-2.12 (4H, m), 2.17-2.30 (2H, m), 2.36-2.56 (6H, m), 2.85-2.98 (1H, m), 2.94 (3H, s), 2.98 (3H×½, s), 3.12 (3H×½, s), 3.46 (2H×½, t, J=7.1 Hz), 3.55 (2H×½, t, J=7.1 Hz), 4.05-4.10 (2H, m), 4.32-4.38 (2H, m), 4.94-5.01 (1H, m), 7.04-7.08 (1H, m), 7.13-7.18 (1H, m), 7.62 (1H×½, d, J=8.8 Hz), 7.67 (1H×½, d, J=8.8 Hz); mass spectrum (ESI): 520.3 (M+H)

Example 88 trans-5'-[(1-Formylazetidin-3-yl)oxy]-3'-oxo-N-methyl-N-(2-piperidin-1-ylethyl)-spiro[cyclohexane-1,1'-(3'H)-isobenzofuran]-4-carboxamide

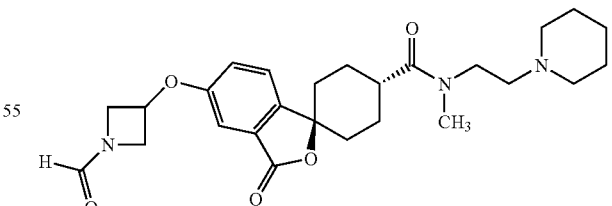

Formic acid (0.27 mL) and acetic anhydride (0.22 mL) were mixed at room temperature and stirred at room temperature for 10 minutes. To this solution was added trans-5'-(azetidin-3-yl)oxy-3'-oxo-N-methyl-N-(2-piperidin-1-ylethyl)-spiro[cyclohexane-1,1'-(3'H)-isobenzofuran]-4-carboxamide (52.1 mg) produced in Example 82 followed by stirring at room temperature for 20 minutes. Toluene was added to the reaction solution, the mixture was concentrated in vacuo and the resulting residue was purified by a reversed phase HPLC (0.1% TFA acetonitrile:H₂O=110% to 70%, gradient). It was further purified by a preparative thin layer chromatography (chloroform/methanol=10/1) to give the title compound (23.0 mg, 42%) as a colorless oily substance.

¹HNMR (400 MHz, CDCl₃, δ): 1.39-1.50 (2H, m), 1.52-1.65 (4H, m), 1.78-1.91 (2H, m), 1.95-2.12 (4H, m), 2.15-2.33 (2H, m), 2.35-2.60 (6H, m), 2.86-2.97 (1H, m), 2.98 (3H×½, s), 3.12 (3H×½, s), 3.46 (2H×½, t, J=7.1 Hz), 3.57 (2H×½, t, J=7.1 Hz), 4.04-4.15 (2H×½, m), 4.17-4.26 (2H×½, m), 4.40-4.53 (2H×½, m), 4.56-4.66 (2H×½, m), 5.03-5.14 (1H, m), 7.03-7.09 (1H, m), 7.13-7.20 (1H, m), 7.63 (1H×½, d, J=8.3 Hz), 7.68 (1H×½, d, J=8.3 Hz), 8.09 (1H, s); mass spectrum (ESI): 470.3 (M+H)

Example 89 trans-5'-[(1-Methoxycarbonylazetizin-3-yl)oxy]-3'-oxo-N-methyl-N-(2-piperidin-1-ylethyl)-spiro[cyclohexane-1,1'-(3'H)-isobenzofuran]-4-carboxamide

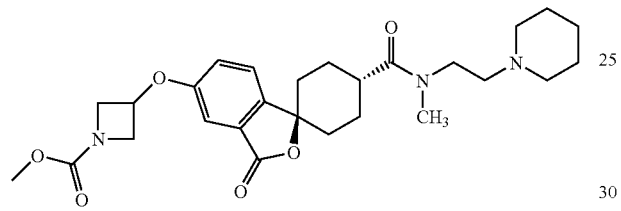

Methyl chloroformate (0.013 mL) and N,N-diisopropylethylamine (0.037 mL) were successively added to a solution of trans-5'-(azetidin-3-yloxy)-3'-oxo-N-methyl-N-(2-piperidin-1-ylethyl)-spiro[cyclohexane-1,1'-(3'H)-isobenzofuran]-4-carboxamide (46.5 mg) produced in Example 82 in tetrahydrofuran (1.0 mL) followed by stirring at room temperature for 1 hour. The solvent of the reaction solution was evaporated in vacuo and the resulting residue was purified by a silica gel column chromatography (Biotage Column NH, hexane/ethyl acetate=0% to 80%, gradient) to give the title compound (27.5 mg, 52%) as a colorless oily substance.

¹HNMR (400 MHz, CDCl₃, δ): 1.38-1.50 (2H, m), 1.53-1.63 (4H, m), 1.79-2.10 (6H, m), 2.17-2.29 (2H, m), 2.38-2.54 (6H, m), 2.85-2.97 (1H, m), 2.98 (3H×½, s), 3.12 (3H×½, s), 3.46 (2H×½, t, J=7.1 Hz), 3.55 (2H×½, t, J=7.1 Hz), 3.70 (3H, s), 4.03-4.10 (2H, m), 4.37-4.45 (2H, m), 4.91-5.00 (1H, m), 7.02-7.06 (1H, m), 7.12-7.17 (1H, m), 7.61 (1H×½, d, J=8.3 Hz), 7.66 (1H×½, d, J=8.3 Hz); mass spectrum (ESI): 500.3 (M+H)

Example 90 trans-5'-[(1-Propionylazetizin-3-yl)oxy]-3'-oxo-N-methyl-N-(2-piperidin-1-ylethyl)-spiro[cyclohexane-1,1'-(3'H)-isobenzofuran]-4-carboxamide

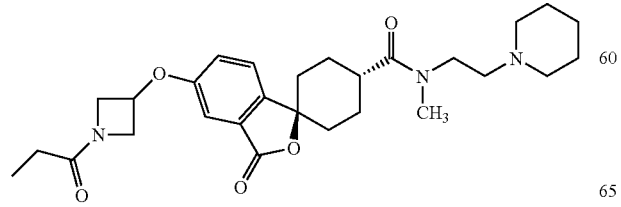

Propionyl chloride (0.018 mL) and N,N-diisopropylethylamine (0.055 mL) were successively added to a solution of trans-5'-(azetidin-3-yloxy)-3'-oxo-N-methyl-N-(2-piperidin-1-ylethyl)-spiro[cyclohexane-1,1'-(3'H)-isobenzofuran]-4-carboxamide (68.5 mg) produced in Example 82 in tetrahydrofuran (1.0 mL) followed by stirring at room temperature for 1 hour. The solvent of the reaction solution was evaporated in vacuo and the resulting residue was purified by a silica gel column chromatography (Biotage Column NH, chloroform/methanol=0% to 5%, gradient) to give 76.7 mg (99%) of the title compound as a colorless oily substance.

¹HNMR (400 MHz, CDCl₃, δ): 1.14 (3H, t, J=7.6 Hz), 1.38-1.50 (2H, m), 1.52-1.70 (4H, m), 1.78-1.91 (2H, m), 1.95-2.09 (4H, m), 2.15 (2H, q, J=7.6 Hz), 2.19-2.30 (2H, m), 2.36-2.64 (6H, m), 2.85-2.97 (1H, m), 2.98 (3H×½, s), 3.13 (3H×½, s), 3.39-3.51 (2H×½, m), 3.53-3.65 (2H×½, m), 4.02-4.12 (2H×½, m), 4.12-4.21 (2H×½, m), 4.36-4.48 (2H×½, m), 4.48-4.60 (2H×½, m), 4.92-5.05 (1H, m), 7.03-7.08 (1H, m), 7.12-7.19 (1H, m), 7.61 (1H×½, d, J=8.3 Hz), 7.67 (1H×½, d, J=8.3 Hz); mass spectrum (ESI): 498.3 (M+H)

Reference Example 1-1

Production of trans-5-(2-fluoroethoxy)-3-oxo-3H-spiro-[2-benzofuran-1,1'-cyclohexane]-4'-carboxylic acid

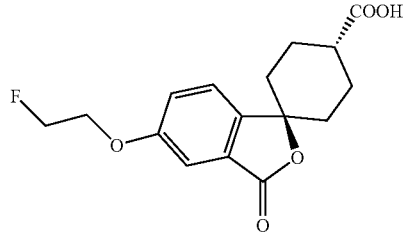

(1) Production of methyl 2-bromo-5-hydroxybenzoate

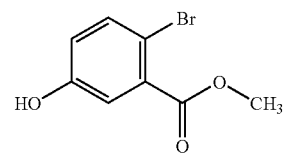

Bromine (6.74 mL) was added to a solution of methyl 3-hydroxybenzoate (20.0 g) in dichloromethane (200 mL) and stirred at room temperature for 4 hours. The reaction solution was concentrated, diisopropyl ether (40 mL) was added and the solid separated out therefrom was filtered to give the aimed compound (28.3 g, 93%) as a colorless solid.

¹HNMR (400 MHz, CDCl₃, δ): 3.93 (3H, s), 6.86 (1H, dd, J=8.6 Hz, 3.1 Hz), 7.31 (1H, d, J=3.1 Hz), 7.49 (1H, d, J=8.6 Hz)

(2) Production of 2-bromo-5-(2-fluoroethoxy)benzoic acid

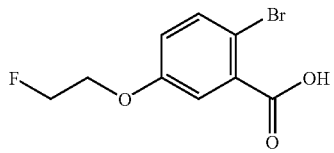

Calcium carbonate (12.0 g) and 2-fluoroethyl 4-methylbenzenesulfonate (9.45 g) were added to a solution of methyl 2-bromo-5-hydroxybenzoate (10.0 g) produced in the above (1) in acetone (100 mL), stirred at room temperature for 13 hours and then stirred at 70° C. for three days. Water was added to the reaction solution followed by extracting with ethyl acetate. The resulting organic layer was washed with a saturated saline solution, dried over sodium sulfate, filtered and concentrated in vacuo. The resulting residue was dissolved in methanol (200 mL), a 4N aqueous solution of sodium hydroxide (15.0 mL) was added thereto, the mixture was stirred at room temperature for 13 hours, a 4N aqueous solution of sodium hydroxide (10.0 mL) was further added thereto and the mixture was stirred at room temperature for 9 hours. To the reaction solution was added 6N hydrochloric acid (20 mL) and the solid separated out therefrom was filtered to give the aimed compound (8.89 g, 78%) as a colorless solid.

$^1$HNMR (400 MHz, DMSO-d$_6$, δ): 4.20-4.46 (2H, m), 4.64-4.82 (2H, m), 7.05 (1H, dd, J=9.0 Hz, 3.1 Hz), 7.28 (1H, d, J=3.1 Hz), 7.76 (1H, d, J=9.0 Hz), 13.41 (1H, brs)

(3) Production of 5-(2-fluoroethoxy)-3H,4'H-spiro-[2-benzofuran-1,1'-cyclohexane]-3,4'-dione

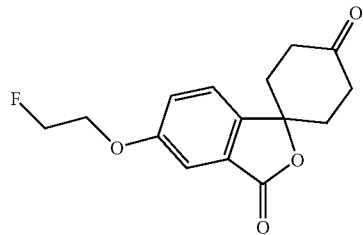

A 1.59 M solution of n-butyl lithium in hexane (26.3 mL) was dropped at −78° C. into a solution of 2-bromo-5-(2-fluoroethoxy)benzoic acid (5.00 g) produced in the above (2) in THF (100 mL) and, after that, the mixture was stirred at −78° C. for 30 minutes. A solution of 1,4-cyclohexanedione monoethyleneacetal (3.27 g) in THF (30 mL) was added to the reaction solution and stirred at room temperature for 21 hours. Water (200 mL) was added to the reaction solution and the mixture was extracted with diethyl ether. To an aqueous layer was added concentrated sulfuric acid (20 mL) followed by stirring at 80° C. for 6 hours. After THF was evaporated, extraction with ethyl acetate was conducted. The organic layer was successively washed with a saturated sodium hydrogen carbonate solution and a saturated saline solution, dried over sodium sulfate, filtered and concentrated in vacuo to give the aimed product (3.04 g, 57%) as a light yellow solid.

$^1$HNMR (400 MHz, CDCl$_3$, δ): 2.06-2.16 (2H, m), 2.33-2.45 (2H, m), 2.47-2.56 (2H, m), 2.90-3.02 (2H, m), 4.23-4.35 (2H, m), 4.72-4.88 (2H, m), 7.30-7.33 (2H, m), 7.36 (1H, t, J=1.4 Hz)

(4) Production of trans-5-(2-fluoroethoxy)-3-oxo-3H-spiro[2-benzofuran-1,1'-cyclohexane]-4'-carbonitrile

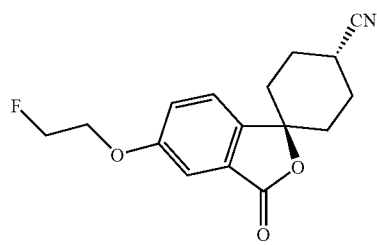

Sodium borohydride (852 mg) was added at 0° C. to a solution of 5-(2-fluoroethoxy)-3H,4'H-spiro[2-benzofuran-1,1'-cyclohexane]-3,4'-dione (3.04 g) produced in the above (3) in THF (50 mL) and water (5.0 mL) and, after that, the mixture was stirred at 0° C. for 5 hours. To the reaction solution was added a saturated aqueous solution of ammonium chloride followed by extracting with ethyl acetate. The organic layer was washed with a saturated saline solution, dried over sodium sulfate, filtered and concentrated in vacuo. The resulting residue was dissolved in THF (50 mL) and then chloroform (30 mL), triethylamine (2.26 mL) and methanesulfonyl chloride (1.00 mL) were added thereto at 0° C. and, after that, the mixture was stirred at 0° C. for 30 minutes. Water was added to the reaction solution followed by extracting with ethyl acetate. The organic layer was washed with a saturated saline solution, dried over sodium sulfate, filtered and concentrated in vacuo. The resulting residue was dissolved in N,N-dimethylformamide (50 mL) and, after addition of tetraethylammonium cyanide (5.00 g) thereto, the mixture was stirred at 80° C. for 3 days. Water was added to the reaction solution followed by extracting with ethyl acetate. The organic layer was washed with a saturated saline solution, dried over sodium sulfate, filtered and concentrated in vacuo. The resulting solid was suspended in diethyl ether and filtered to give the aimed product (1.59 g, 50%) as a colorless solid.

$^1$HNMR (400 MHz, CDCl$_3$, δ): 1.72-1.82 (2H, m), 2.02-2.34 (6H, m), 3.10-3.18 (1H, m), 4.22-4.34 (2H, m), 4.71-4.88 (2H, m), 7.28-7.44 (3H, m)

(5) Production of trans-5-(2-fluoroethoxy)-3-oxo-3H-spiro[2-benzofuran-1,1'-cyclohexane]-4'-carboxylic acid

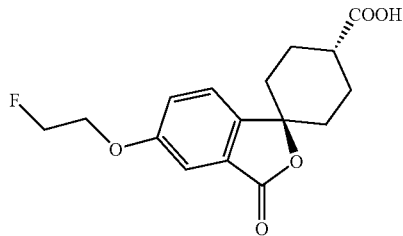

A 30% aqueous solution of sulfuric acid (5.0 mL) was added to a solution of 5-(2-fluoroethoxy)-3-oxo-3H-spiro[2-benzofuran-1,1'-cyclohexane]-4'-carbonitrile (700 mg) produced in the above (4) in 1,4-dioxane (5.0 mL) and, after that, the mixture was stirred at 100° C. for 2 days. To the reaction solution was added a 4N aqueous solution of sodium hydroxide at 0° C. to adjust to pH ca. 3 followed by extracting with ethyl acetate. The organic layer was washed with a saturated saline solution, dried over sodium sulfate, filtered and concentrated in vacuo. The resulting solid was suspended in diethyl ether and filtered and the filtrate was concentrated in vacuo. The resulting residue was purified by a silica gel column chromatography (chloroform/methanol=100/1) to give the title compound (409 mg, 55%) as a colorless solid.

$^1$HNMR (400 MHz, CDCl$_3$, δ): 1.68-1.80 (2H, m), 2.04-2.28 (6H, m), 2.85-2.93 (1H, m), 4.22-4.36 (2H, m), 4.70-4.86 (2H, m), 7.24-7.38 (3H, m)

Reference Example 1-2

Production of trans-3-oxo-3H-spiro[2-benzofuran-1,1'-cyclohexane]-4'-carboxylic acid

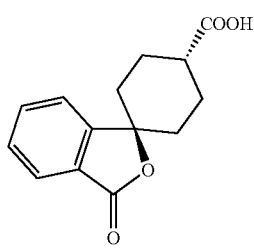

The title compound was produced by the same method as Reference Example 1-1, by a method similar thereto or by a combination thereof with a common method using 2-bromobenzoic acid as a material.

$^1$HNMR (400 MHz, CDCl$_3$, δ): 1.72-1.83 (2H, m), 2.09-2.29 (6H, m), 2.88-2.95 (1H, m), 7.46 (1H, d, J=7.6 Hz), 7.51-7.56 (1H, m), 7.63-7.69 (1H, m), 7.86-7.94 (1H, m)

Reference Example 1-3

Production of trans-5-methoxy-3-oxo-3H-spiro[2-benzofuran-1,1'-cyclohexane]-4'-carboxylic acid

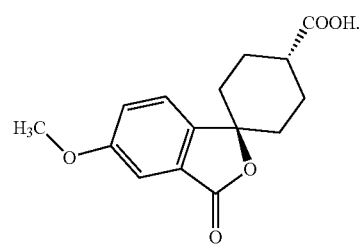

The title compound was produced by the same method as Reference Example 1-1, by a method similar thereto or by a combination thereof with a common method using 2-bromo-5-methoxybenzoic acid as a material.

$^1$HNMR (400 MHz, CDCl$_3$, δ): 1.70-1.80 (2H, m), 2.04-2.27 (6H, m), 2.85-2.92 (1H, m), 3.87 (3H, s), 7.21 (1H, dd, J=8.3 Hz, 2.4 Hz), 7.32-7.38 (2H, m)

Reference Example 1-4

Production of trans-5-fluoro-3-oxo-3H-spiro[2-benzofuran-1,1'-cyclohexane]-4'-carboxylic acid

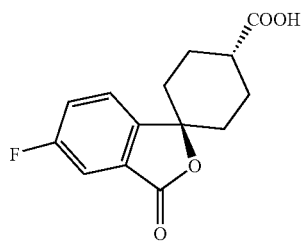

The title compound was produced by the same method as Reference Example 1-1, by a method similar thereto or by a combination thereof with a common method using 2-bromo-5-fluorobenzoic acid as a material.

$^1$HNMR (400 MHz, CDCl$_3$, δ): 1.68-1.82 (2H, m), 2.05-2.30 (6H, m), 2.87-2.95 (1H, m), 7.32-7.44 (2H, m), 7.50-7.58 (1H, m)

Reference Example 2-1

Production of trans-7-methoxy-3-oxo-3H-spiro[2-benzofuran-1,1'-cyclohexane]-4'-carboxylic acid

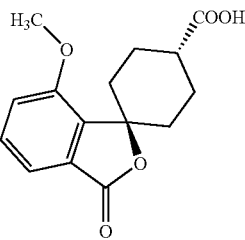

(1) Production of 2-(3-methoxyphenyl)-4,4-dimethyl-2-oxazoline

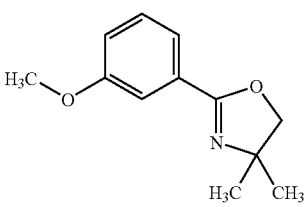

Triethylamine (23.0 mL) was added to a solution of 2-amino-2-methyl-1-propanol (14.4 g) in THF (200 mL), 3-methoxybenzoyl chloride (25.0 g) was dropped thereinto at 0° C. and the mixture was stirred at room temperature for 1 day. After water was added to the reaction solution, the mixture was extracted with ethyl acetate. The organic layer was washed with a saturated saline solution, dried over sodium sulfate, filtered and concentrated in vacuo. Thionyl chloride (25 mL) was dropped into the resulting residue at 0° C. and stirred at room temperature for 3 hours. An aqueous solution of sodium hydroxide was added to the reaction solution and extracted with ethyl acetate. The organic layer was washed with a saturated saline solution, dried over magnesium sulfate, filtered and concentrated in vacuo. The resulting residue was evaporated in vacuo to give the aimed compound (22.0 g, 81%) as a colorless oily substance.

$^1$HNMR (300 MHz, CDCl$_3$, δ): 1.39 (6H, s), 3.85 (3H, s), 4.10 (2H, s), 6.98-7.05 (1H, m), 7.26-7.34 (1H, m), 7.44-7.55 (2H, m)

(2) Production of 2-[(7-methoxy-3H-dispiro[2-benzofuran-1,1'-cyclohexane-4',2"-[1,3]dioxoran]-3-ylidene)-amino]-2-methyl-1-propanol

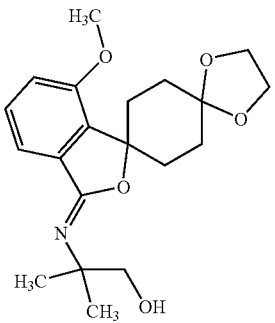

A 2.66M n-butyl lithium solution in hexane (11.0 mL) was added at −78° C. to a solution of 2-(3-methoxyphenyl)-4,4-dimethyl-2-oxazoline (5.00 g) produced in the above (1) in THF (50 mL) and, after that, the mixture was stirred at room temperature for 1 hour. To the reaction solution was added a solution of 1,4-cyclohexanedione monoethyleneacetal (3.80 g) in THF (30 mL) followed by stirring at room temperature for 2 hours. To the reaction solution was added at 0° C. a saturated aqueous solution of ammonium chloride and the mixture was extracted with ethyl acetate. The organic layer was washed with a saturated saline solution, dried over sodium sulfate, filtered and concentrated in vacuo. The resulting residue was purified by a silica gel column chromatography (hexane/ethyl acetate=3/1→1/1→1/2) to give the aimed compound (4.11 g, 47%) as a colorless solid.

$^1$HNMR (400 MHz, CDCl$_3$, δ): 1.36 (6H, s), 1.56-1.68 (2H, m), 1.72-1.88 (2H, m), 2.04-2.18 (2H, m), 2.54-2.68 (2H, m), 3.40 (2H, s), 3.89 (3H, s), 4.04 (4H, s), 6.92-6.96 (1H, m), 7.28-7.40 (2H, m)

(3) Production of 7-methoxy-3H,4'H-spiro[2-benzofuran-1,1'-cyclohexane]-3,4'-dione

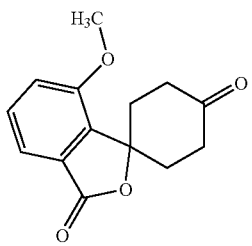

A 2N aqueous solution of sulfuric acid (10 mL) was added to a solution of 2-[(7-methoxy-3H-dispiro[2-benzofuran-1,1'-cyclohexane-4',2"-[1,3]dioxoran]-3-ylidene)-amino]-2-methyl-1-propanol produced in the above (2) in acetone (40 mL) and, after that, the mixture was stirred at 50° C. for 22 hours and then at 80° C. for 19 hours. After a saturated aqueous solution of sodium hydrogen carbonate was added thereto, the mixture was extracted with ethyl acetate. The organic layer was washed with a saturated saline solution, dried over sodium sulfate, filtered and concentrated in vacuo. The resulting solid was suspended in diethyl ether and filtered to give the aimed compound (2.06 g, 74%) as a light pink solid.

$^1$HNMR (400 MHz, CDCl$_3$, δ): 1.95-2.05 (2H, m), 2.43-2.52 (2H, m), 2.76-2.87 (2H, m), 2.89-3.01 (2H, m), 3.92 (3H, s), 7.10-7.18 (1H, m), 7.48-7, 56 (2H, m)

(4) Production of trans-7-methoxy-3-oxo-3H-spiro[2-benzofuran-1,1'-cyclohexane]-4'-carboxylic acid

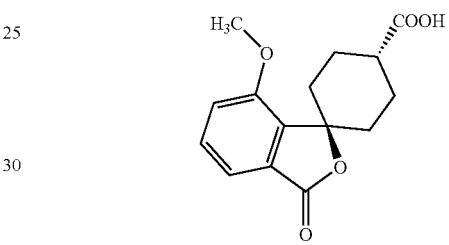

The same method as in Reference Example 1, a method similar to that or a combination thereof with a conventional method was carried out using 7-methoxy-3H,4'H-spiro[2-benzofuran-1,1'-cyclohexane]-3,4'-dione produced in the above (3) as a material to give the title compound.

$^1$HNMR (400 MHz, CDCl$_3$, δ): 1.52-1.60 (2H, m), 2.06-2.28 (4H, m), 2.52-2.64 (2H, m), 2.90-2.96 (1H, m), 3.88 (3H, s), 7.04-7.14 (1H, m), 7.42-7.50 (2H, m)

Reference Example 2-2

Production of trans-6-methoxy-3-oxo-3H-spiro[2-benzofuran-1,1'-cyclohexane]-4'-carboxylic acid

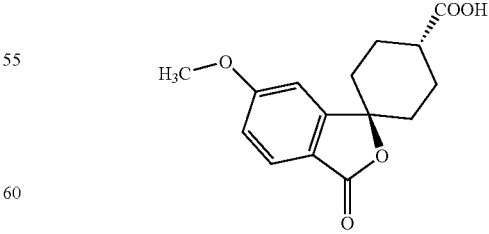

The same method as in Reference Examples 2-1 and 1-1, a method similar thereto or a combination thereof with a conventional method was carried out using 4-methoxybenzoyl chloride as a material to give the title compound.

¹HNMR (400 MHz, DMSO-d₆, δ): 1.54-1.66 (2H, m), 1.83-2.13 (6H, m), 2.68-2.76 (1H, m), 3.88 (3H, s), 7.04-7.16 (2H, m), 7.71 (1H, d, J=8.2 Hz), 12.30 (1H, s)

Reference Example 3

Production of trans-5-hydroxy-3-oxo-3H-spiro[2-benzofuran-1,1'-cyclohexane]-4'-carboxylic acid

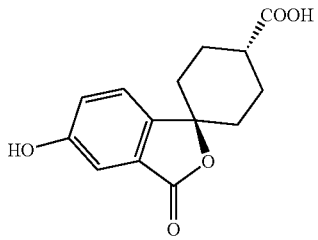

Boron trifluoride (10.3 mL) was dropped into a solution of trans-5-methoxy-3-oxo-3H-spiro[2-benzofuran-1,1'-cyclohexane]-4'-carboxylic acid (10.3 mL) produced in Reference Example 1-3 in methylene chloride (100 mL) under cooling with ice. After the mixture was raised up to room temperature, it was stirred throughout one night at room temperature. The reaction solution was poured into ice water and extracted with ethyl acetate and the extract was washed with a saturated saline solution. The organic layer was dried over sodium sulfate, filtered and concentrated in vacuo to give the title compound (6.11 g, 64%) as a white solid.

¹HNMR (400 MHz, DMSO-d₆, δ): 1.58-1.70 (2H, m), 1.84-1.95 (4H, m), 1.95-2.06 (2H, m), 2.62-2.70 (1H, m), 7.05 (1H, d, J=2.2 Hz), 7.12-7.14 (1H, m), 7.40 (1H, d, J=8.2 Hz)

Reference Example 4

Production of trans-2'-methyl-3'-oxo-2',3'-dihydro-spiro-[cyclohexane-1,1'-isoindole]-4-carboxylic acid and cis-2'-methyl-3'-oxo-2',3'-dihydrospiro-[cyclohexane-1,1'-isoindole]-4-carboxylic acid

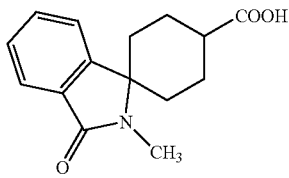

(1) Production of ethyl 2'-methyl-3'-oxo-2',3'-dihydro-spiro-[cyclohex-3-ene-1,1'-isoindole]-4-carboxylate

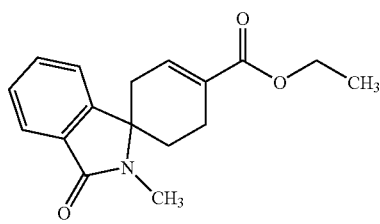

A 40% methanolic solution (20.0 mL) of methylamine was added to a solution of ethyl 4-oxocyclohexanecarboxylate (10.0 g) in diethyl ether (100 mL) and stirred at room temperature for 5.5 hours. Drylite (10.0 g) was added thereto followed by stirring at room temperature for 18 hours. After it was filtered, the filtrate was concentrated. The resulting residue was dissolved in toluene (100 mL), then triethylamine (8.20 mL) and 2-iodobenzoyl chloride (10.97 g) were added thereto and the mixture was stirred for 2 days at 80° C. in a nitrogen atmosphere. A saturated sodium bicarbonate solution was added to the reaction solution and the mixture was extracted with ethyl acetate. The organic layer was washed with a saturated saline solution, dried over sodium sulfate, filtered and concentrated in vacuo. It was purified by a silica gel column chromatography (hexane/ethyl acetate=9/1→3/1). The resulting residue was dissolved in acetonitrile (200 mL), then potassium carbonate (10.70 g), tetraethylammonium chloride (6.42 g), triphenylphosphine (2.03 g) and palladium acetate (869 mg) were added thereto and the mixture was stirred for 17 hours at 80° C. in a nitrogen atmosphere. Water was added to the reaction solution and the mixture was extracted with ethyl acetate. The organic layer was washed with a saturated saline solution, dried over sodium sulfate, filtered and concentrated in vacuo. It was purified by a silica gel column chromatography (hexane/ethyl acetate=3/1→3/2). The resulting solid was suspended in diisopropyl ether and filtered to give the aimed compound (7.36 g, 44%) as a light yellow solid.

¹HNMR (400 MHz, CDCl₃, δ): 1.36 (3H, t, J=7.1 Hz), 1.50-1.60 (1H, m), 2.14-2.26 (2H, m), 2.60-2.74 (1H, m), 2.76-2.88 (2H, m), 3.05 (3H, s), 4.28 (2H, q, J=7.1 Hz), 7.13-7.18 (1H, m), 7.30-7.35 (1H, m), 7.43-7.71 (2H, m), 7.84-7.90 (1H, m)

(2) Production of trans-2'-methyl-3'-oxo-2',3'-dihydrospiro[cyclohexane-1,1'-isoindole]-4-carboxylic acid and cis-2'-methyl-3'-oxo-2',3'-dihydrospiro-[cyclohexane-1,1'-isoindole]-4-carboxylic acid

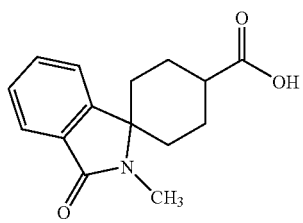

A 5% palladium carbon (400 mg) was added to a solution of ethyl 2'-methyl-3'-oxo-2',3'-dihydrospiro[cyclohex-3-ene-1,1'-isoindole]-4-carboxylate (2.00 g) prepared in the above (1) in ethanol (30 mL) and the mixture was stirred at room temperature for 3 days in a hydrogen atmosphere. After the reaction solution was filtered, the filtrate was concentrated. The resulting residue was purified by a silica gel column chromatography (hexane:ethyl acetate=3/1→1/1) to give a cis compound (1.65 g) as a colorless oily substance and a trans compound as a mixture (832 mg, as a colorless oily substance) with a cis compound in a ratio of about 3:1. The resulting trans-cis mixture in about 3:1 (831 mg) was dissolved in methanol (15 mL), a 2N aqueous solution of sodium hydroxide (4.34 mL) was added thereto and the mixture was stirred at room temperature for one day. The reaction solution was adjusted to pH 2 using a 2N hydrochloric acid, concentrated in vacuo and extracted with ethyl acetate. The organic layer was washed with a saturated saline solution, dried over sodium sulfate, filtered and concentrated in vacuo. The resulting residue was purified by a reversed phase HPLC (0.1%

TFA acetonitrile:H₂O=5% to 75%, gradient) to give a trans compound (369 mg) as a colorless solid and a cis compound (146 mg) as a colorless solid.

trans-2'-methyl-3'-oxo-2',3'-dihydrospiro-[cyclohexane-1,1'-isoindole]-4-carboxylic acid ¹HNMR (400 MHz, CDCl₃, δ): 1.46-1.58 (2H, m), 2.17-2.44 (6H, m), 2.92-3.00 (1H, m), 3.11 (3H, s), 7.47-7.58 (2H, m), 7.72 (1H, d, J=7.6 Hz), 7.89-7.94 (1H, m), 10.68 (1H, brs)

cis-2'-methyl-3'-oxo-2',3'-dihydrospiro[cyclohexane-1,1'-isoindole]-4-carboxylic acid ¹HNMR (400 MHz, CDCl₃, δ): 1.54-1.62 (2H, m), 2.00-2.14 (2H, m), 2.17-2.32 (4H, m), 2.52-2.65 (1H, m), 3.09 (3H, s), 7.49-7.61 (2H, m), 7.83 (1H, d, J=7.4 Hz), 7.90-7.96 (1H, m), 9.76 (1H, brs)

Reference Example 5

Production of trans-5-methoxy-3-oxo-3H-spiro-[2-benzofuran-1,1'-cyclohexane]-4'-methyl-4'-carboxylic acid

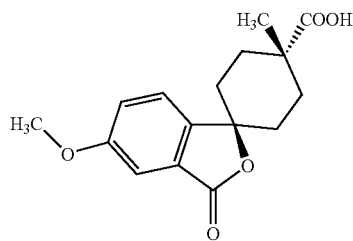

(1) Production of methyl trans-5-methoxy-3-oxo-3H-spiro-[2-benzofuran-1,1'-cyclohexane]-4'-carboxylate

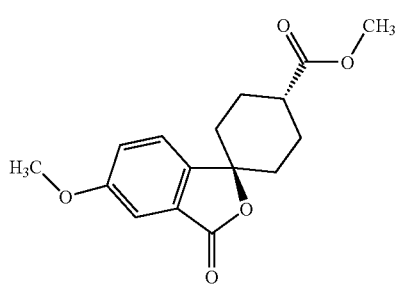

Concentrated sulfuric acid (0.5 mL) was added, under cooling with ice, to a solution of trans-5-methoxy-3-oxo-3H-spiro[2-benzofuran-1,1'-cyclohexane]-4'-carboxylic acid (1.00 g) prepared in Reference Example 1-3 in methanol (20 mL). The reaction solution was stirred for 5 hours under heating to reflux. After the reaction solution was cooled down to room temperature, a saturated aqueous solution of sodium bicarbonate was added thereto followed by extracting with ethyl acetate. The organic layer was dried over sodium sulfate, filtered and concentrated in vacuo. The residue was purified by a silica gel column chromatography (Biotage Column, hexane/ethyl acetate=0% to 60%, gradient) to give the title compound (940 mg, 87%) as a white solid.

¹HNMR (400 MHz, CDCl₃, δ): 1.67-1.77 (2H, m), 2.01-2.19 (6H, m), 2.80 (1H, t, J=4.4 Hz), 3.76 (3H, s), 3.86 (3H, s), 7.20 (1H, dd, J=8.3, 2.2 Hz), 7.31 (1H, d, J=2.2 Hz), 7.33 (1H, d, J=8.3 Hz); mass spectrum (ESI): 291.2 (M+H)

(2) Production of methyl trans-5-methoxy-3-oxo-3H-spiro-[2-benzofuran-1,1'-cyclohexane]-4'-methyl-4'-carboxylate

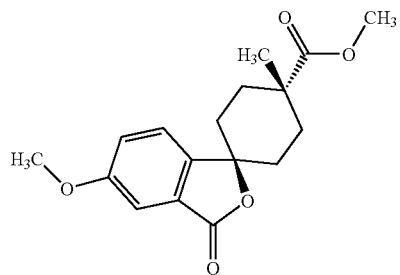

n-Butyl lithium (1.6M solution in hexane) (1.40 mL) was added, at −78° C., to a solution of diisopropylamine (0.31 mL) in tetrahydrofuran (10 mL) and the mixture was stirred at −78° C. for 30 minutes. To the reaction solution was added, at −78° C., a solution of methyl trans-5-methoxy-3-oxo-3H-spiro[2-benzofuran-1,1'-cyclohexane]-4'-carboxylate (500 mg) prepared in the above (1) in tetrahydrofuran (10 mL) followed by stirring at −78° C. for 1 hour. After methyl iodide (0.16 mL) was added at −78° C. thereto, temperature of the reaction solution was raised to room temperature followed by stirring throughout the night. The reaction solution was made acidic by addition of a 2M aqueous solution of hydrochloric acid, a saturated saline solution was added thereto and the mixture was extracted with ethyl acetate. The organic layer was dried over sodium sulfate, filtered and concentrated in vacuo. The residue was purified by a silica gel column chromatography (Biotage Column, hexane/ethyl acetate=0% to 50%, gradient) to give the title compound (405 mg, 77%) as a white solid.

¹HNMR (400 MHz, CDCl₃, δ): 1.28 (3H, s), 1.61-1.69 (2H, m), 1.75-1.84 (2H, m), 1.92-2.02 (2H, m), 2.19-2.26 (2H, m), 3.77 (3H, s), 3.86 (3H, s), 7.16-7.24 (2H, m), 7.28-7.30 (1H, m); mass spectrum (ESI): 305.3 (M+H)

(3) Production of trans-5-methoxy-3-oxo-3H-spiro-[2-benzofuran-1,1'-cyclohexane]-4'-methyl-4'-carboxylic acid

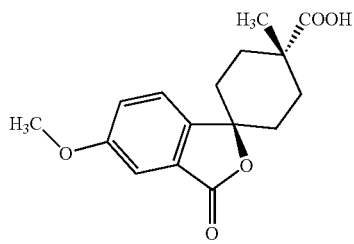

Water (1.0 mL) and lithium hydroxide (1.0 g) were added to a solution of methyl trans-5-methoxy-3-oxo-3H-spiro-[2- benzofuran-1,1'-cyclohexane]-4'-methyl-4'-carboxylate (200 mg) produced in the above (2) in methanol (10 mL) followed by stirring throughout a night under heating to reflux. The reaction solution was made acidic by addition of a 1N aqueous solution of hydrochloric acid and extracted with ethyl acetate. The organic layer was dried over sodium sulfate, filtered and concentrated in vacuo. The residue was purified by a silica gel column chromatography (Biotage Column, chloroform/methanol=10% to 20%, gradient) to give the title compound (191 mg, 100%) as a white solid.

$^1$HNMR (400 MHz, CDCl$_3$, δ): 1.38 (3H, s), 1.70 (2H, d, J=13.7 Hz), 1.86 (2H, td, J=13.7, 3.6 Hz), 2.08 (2H, td, J=13.7, 3.6 Hz), 2.26 (2H, d, J=13.7 Hz), 3.87 (3H, s), 7.19-7.24 (1H, m), 7.26-7.35 (2H, m); mass spectrum (ESI): 291.2 (M+H)

Usefulness of the compound represented by the formula (I), (I-1), (I-2), (I-3), (14), (I-5), (I-6), (I-7), (I-8), (I-9) or (I-10) or a pharmaceutically acceptable salt thereof can be proved by, for example, the following Pharmacological Test Example.

Pharmacological Test Example where the compounds of Examples 10, 14, 58 and 68 were used as test compounds will be shown below.

Pharmacological Test Example 1

Test for Inhibition of Bonding of Histamine Analog

A cDNA sequence coding for human histamine H3 receptor [refer to WO 00/39164] was cloned to an expression vector pCR2.1, pEF1× (manufactured by Invitrogen) and pCI-neo (manufactured by Promega). The resulting expression vector was transfected to host cells HEK293 and CHO-K1 (American Type Culture Collection) by a cationic lipid method [refer to Proceedings of the National Academy of Sciences, the United States of America, volume 84, page 7413 (1987)] to give histamine H3 receptor-expressed cells.

A membrane specimen prepared from the cells where histamine H3 receptor was expressed was incubated at 25° C. for 2 hours in an assay buffer (50 mM Tris buffer, pH 7.4) together with a test compound (the compound of Example 1) and 20,000 cpm of [3H]N-α-methylhistamine (manufactured by NEN) and then filtered using a glass filter GF/C. After washing with a 50 mM Tris buffer of pH 7.4, radiation activity on the glass filter was determined. Non-specific bond was measured in the presence of a 10 μM thioperamide (manufactured by Sigam) to determine a 50% inhibition concentration (IC$_{50}$ value) of the test compound to a specific N-alpha-methylhistamine bond [refer to Molecular Pharmacology, volume 55, page 1101 (1999)]. As a result, the IC$_{50}$ value of the compound of Example 10 was 4 nM, that of the compound of Example 14 was 9 nM, that of the compound of Example 58 was 0.08 nM and that of the compound of Example 68 was 0.67 nM.

As mentioned above, the compounds of Examples 10, 14, 58 and 68 strongly inhibited the bond of N-alpha-methylhistamine (histamine analog) to a histamine H3 receptor.

INDUSTRIAL APPLICABILITY

In accordance with the present invention, there is provided a novel substance having an antagonistic action against a histamine H3 receptor (an action which inhibits the bonding of histamine to histamine H3 receptor) or an inverse agonistic action against the same (an action which suppresses a homeostatic activity of histamine H3 receptor) or, in other words, a novel substance acting as a histamine H3 receptor agonist or antagonist in living body.

The carbamoyl-substituted spiro derivative represented by the formula (I) or a pharmaceutically acceptable salt thereof provided by the present invention has a strong histamine H3 receptor antagonistic action or inverse agonistic action and is useful for prevention or treatment of metabolic diseases such as obesity, diabetes, dysendocrinism, hyperlipemia, gout and fatty liver; circulatory disease such as stenocardia, acute congestive cardiac insufficiency, myocardial infarction, coronary sclerosis, hypertension, renal disease and electrolyte imbalance; or central and peripheral neural diseases such as sleep disorder, disease accompanied by sleep disorder (e.g., idiopathic hypersomnia, repetitive hypersomnia, true hypersomnia, narcolepsy, sleep periodic limb movement disorder, sleep apnea syndrome, circadian rhythm disorder, chronic fatigue syndrome, REM sleep disorder, senile insomnia, sleep unwholesomeness of night-work laborers, idiopathic insomnia, repetitive insomnia, true insomnia, depression, anxiety and schizophrenia), hyperphagia, emotional disturbance, epilepsy, delirium, dementia, attention deficit/hyperactivity disorder, memory disorder, Alzheimer's disease, Parkinson's disease, recognition disorder, motion disorder, paresthesia, dysosmia, resistance to morphine, narcotic dependence, alcoholic dependence and tremor.

The invention claimed is:
1. A compound of the formula (I):

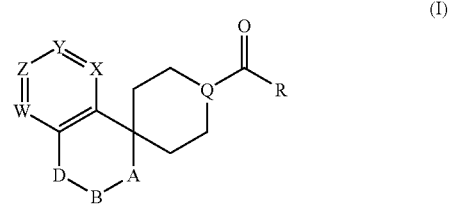

wherein,
X, Y, Z and W each independently represent a methine group optionally having a substituent(s) selected from the group α,
A represents —O— or N(R$^5$)—,
B represents —C(O)—,
D represents a bond,
Q represents a methine group or a nitrogen atom,
R$^5$ represents a hydrogen atom, a lower alkyl group, an aralkyl group or an aryl group,
R represents a group of the following formula (II) which may have a substituent selected from the group consisting of a lower alkyl group (said lower alkyl group may be substituted with a halogen atom, an oxo group or an alkoxy group), a cycloalkyl group, a hydroxy group, an alkoxy group (said alkoxy group may be substituted with a halogen atom) and a halogen atom;

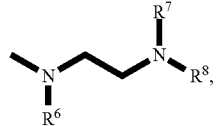

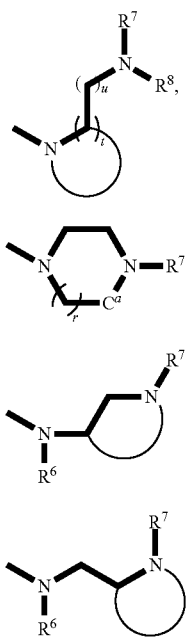

(II-2)

(II-3)

(II-4)

(II-5)

wherein, $R^6$ represents a hydrogen atom or a lower alkyl group, $R^7$ and $R^8$ each independently represent a lower alkyl group, a cycloalkyl group, an aralkyl group, a heteroaryl alkyl group or $R^7$ and $R^8$ together with the nitrogen atom to which they bond form a four- to eight-membered nitrogen-containing aliphatic heterocyclic group; or when R is the above formula (II-3), $C^a$ and $R^7$ together with the nitrogen atom to which bond form a four- to eight-membered nitrogen-containing aliphatic heterocyclic group; and the formula

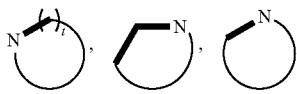

wherein (II-2), (II-4) and (II-5) represent a four- to eight-membered nitrogen-containing aliphatic heterocyclic group), m1 and m2 each independently indicate 0 or 1, r indicates an integer of 0 to 2, t indicates 1 or 2;

u indicates 0 or 1 (with a proviso that t+u is 2);

the group α is selected from: a halogen atom, a hydroxyl group, a lower alkyl group (said group may be substituted with a halogen atom, a hydroxyl group or an alkoxy group), a cycloalkyl group (said group may be substituted with a halogen atom, a hydroxyl group or an alkoxy group), an alkoxy group (said group may be substituted with a halogen atom or a hydroxyl group), an amino group, a cyano group, a mono- or di-(lower alkyl) amino group, a formyl group, an alkanoyl group, a mono- or di-lower alkylcarbamoyl group, an arylcarbamoyl group, a heteroarylcarbamoyl group, an aralkylcarbamoyl group, a heteroarylalkylcarbamoyl group, a lower alkylsulfonyl group, a lower alkylthio group, an aryloxycarbonylamino group, an arylalkyloxycarbonylamino group, an alkoxycarbonylamino group, an alkanoylamino group, an arylcarbonylamino group, an arylalkylcarbonyl group, a lower alkylsulfonylamino group, an arylsulfonylamino group, a lower alkylsulfamoyl group, an arylsulfamoyl group, an aryl group, an aryloxy group, a heteroaryl group and an aralkyl group;

or a pharmaceutically acceptable salt thereof.

2. The compound of claim 1, wherein Q is a methine group.

3. The compound of claim 1, wherein Q is a nitrogen atom.

4. A compound which is selected from the group consisting of:

trans-5'-(2-fluoroethoxy)-3'-oxo-N-methyl-N-(2-piperidin-1-ylethyl)-spiro[cyclohexane-1,1'-(3'H)-isobenzofuran]-4-carboxamide hydrochloride, trans-3'-oxo-N-methyl-N-(2-piperidin-1-ylethyl)-spiro[cyclohexane-1,1'-(3'H)-isobenzofuran]-4-carboxamide hydrochloride, trans-3'-oxo-N-methyl-N-(2-pyrrolidin-1-ylethyl)-spiro[cyclohexane-1,1'-(3'H)-isobenzofuran]-4-carboxamide hydrochloride, trans-3'-oxo-N-(2-piperidin-1-ylethyl)-spiro[cyclohexane-1,1'-(3'H)-isobenzofuran]-4-carboxamide, trans-3'-oxo-N-(2-pyrrolidin-1-ylethyl)-spiro[cyclohexane-1,1'-(3'H)-isobenzofuran]-4-carboxamide, trans-4-ethylpiperazinyl-(2S)-methyl-3'-oxospiro[cyclohexane-1,1'-(3'H)-isobenzofuran]-4-carboxamide, trans-4-(hexahydropyrrolo[1,2-a]pyrazinyl)-3'-oxospiro[cyclohexane-1,1'-(3'H)-isobenzofuran]-4-carboxamide, trans-3'-oxo-N-methyl-N-(1-cyclopentylpyrrolidin-3-yl)-spiro[cyclohexane-1,1'-(3'H)-isobenzofuran]-4-carboxamide, trans-5'-methoxy-3'-oxo-N-methyl-N-(2-piperidin-1-ylethyl)-spiro[cyclohexane-1,1'-(3'H)-isobenzofuran]-4-carboxamide hydrochloride, trans-5'-fluoro-3'-oxo-N-methyl-N-(2-piperidin-1-ylethyl)-spiro[cyclohexane-1,1'-(3'H)-isobenzofuran]-4-carboxamide hydrochloride, trans-5'-fluoro-2-pyrrolidin-1-ylmethylpyrrolidinyl-3'-oxospiro[cyclohexane-1,1'-(3'H)-isobenzofuran]-4-carboxamide hydrochloride, trans-7'-methoxy-3'-oxo-N-methyl-N-(2-piperidin-1-ylethyl)-spiro[cyclohexane-1,1'-(3'H)-isobenzofuran]-4-carboxamide hydrochloride, trans-7'-methoxy-3'-oxo-N-methyl-N-(2-pyrrolidin-1-ylethyl)-spiro[cyclohexane-1,1'-(3'H)-isobenzofuran]-4-carboxamide hydrochloride, trans-6'-methoxy-3'-oxo-N-methyl-N-(2-pyrrolidin-1-ylethyl)-spiro[cyclohexane-1,1'-(3'H)-isobenzofuran]-4-carboxamide, cis-N,2'-dimethyl-3'-oxo-N-(2-piperidin-1-ylethyl)-2',3'-dihydrospiro[cyclohexane-1,1'-isoindole]-4-carboxamide, trans-5'-methoxy-3'-oxo-N-methyl-N-(2-pyrrolidin-1-ylethyl)-spiro[cyclohexane-1,1'-(3'H)-isobenzofuran]-4-carboxamide, trans-5'-fluoro-3'-oxo-N-methyl-N-(2-pyrrolidin-1-ylethyl)-spiro[cyclohexane-1,1'-(3'H)-isobenzofuran]-4-carboxamide, trans-5'-hydroxy-3'-oxo-N-methyl-N-(2-pyrrolidin-1-ylethyl)-spiro[cyclohexane-1,1'-(3'H)-isobenzofuran]-4-carboxamide, 1'-(4-piperidin-1-ylbutanoyl)-3H-spiro[2-benzofuran-1,4'-piperidine]-3-one, trans-5'-methoxy-3'-oxo-N,4-dimethyl-N-(2-pyrrolidin-1-ylethyl)-spiro[cyclohexane-1,1'-(3'H)-isobenzofuran]-4-carboxamide, trans-5'-hydroxy-3'-oxo-(N-methyl-N-(2-piperidin-1-ylethyl)-spiro[cyclohexane-1,1'-(3'H)-isobenzofuran]-4-carboxamide, trans-3'-oxo-N-ethyl-N-(2-piperidin-1-ylethyl)-spiro[cyclohexane-1,1'-(3'H)-isobenzofuran]-4-carboxamide hydrochloride,
trans-4-cyclopentylpiperazinyl-3'-oxospiro[cyclohexane-1,1'-(3'H)-isobenzofuran]-4-carboxamide,
trans-4-cyclohexylpiperazinyl-3'-oxospiro[cyclohexane-1,1'-(3'H)-isobenzofuran]-4-carboxamide,
trans-4-butylpiperazinyl-3'-oxospiro[cyclohexane-1,1'-(3'H)-isobenzofuran]-4-carboxamide,
trans-4-(1-ethylpropyl)piperazinyl-3'-oxospiro[cyclohexane-1,1'-(3'H)-isobenzofuran]-4-carboxamide,
trans-4-(1-methylpropyl)piperazinyl-3'-oxospiro[cyclohexane-1,1'-(3'H)-isobenzofuran]-4-carboxamide,
trans-4-isopropylpiperazinyl-3'-oxospiro[cyclohexane-1,1'-(3'H)-isobenzofuran]-4-carboxamide,
trans-4-propylpiperazinyl-3'-oxospiro[cyclohexane-1,1'-(3'H)-isobenzofuran]-4-carboxamide,
trans-5'-fluoromethoxy-3'-oxo[N-methyl-N-(2-piperidin-1-ylethyl)-spiro[cyclohexane-1,1'-(3'H)-iso-benzofuran]-4-carboxamide hydrochloride,
N-methyl-3-oxo-N-(2-piperidin-1-ylethyl)-1'H,3H-spiro[2-benzofuran-1,4'-piperidine]-1'-carboxamide hydrochloride,
N-methyl-N-(2-piperidin-1-ylethyl)-1'H,3H-spiro[2-benzofuran-1,4'-piperidine]-1'-carboxamide hydrochloride,
4-fluoro-N-methyl-3-oxo-N-(2-piperidin-1-ylethyl)-1'H,3H-spiro[2-benzofuran-1,4'-piperidine]-1'-carboxamide,
N,2-dimethyl-3-oxo-N-(2-piperidin-1-ylethyl)-2,3-dihydro-1'H-spiro[isoindole-1,4'-piperidine]-1'-carboxamide,
N-methyl-3-oxo-N-(2-piperidin-1-ylethyl)-2,3-dihydro-1'H-spiro[isoindole-1,4'-piperidine]-1'-carboxamide,
trans-5'-methoxy-3'-oxo-N-methyl-N-{2-[(3S)-3-methylpiperidin-1-yl]ethyl}-spiro[cyclohexane-1,1'-(3'H)-isobenzofuran]-4-carboxamide,
trans-5'-methoxy-3'-oxo-N-methyl-N-[2-(dimethylamino)ethyl]-spiro[cyclohexane-1,1'-(3'H)-isobenzofuran]-4-carboxamide,
trans-5'-methoxy-3'-oxo-N-methyl-N-[2-azetidin-1-ylethyl]-spiro[cyclohexane-1,1'-(3'H)-isobenzofuran]-4-carboxamide,
trans-5'-methoxy-3'-oxo-N-methyl-N-{2-[(2R)-2-methylpyrrolidin-1-yl]ethyl}-spiro[cyclohexane-1,1'-(3'H)-isobenzofuran]-4-carboxamide,
trans-5'-methoxy-3'-oxo-N-methyl-N-[2-(2-methylpiperidin-1-yl)ethyl]-spiro[cyclohexane-1,1'-(3'H)-isobenzofuran]-4-carboxamide,
trans-5'-methoxy-3'-oxo-N-methyl-N-(2-azepan-1-ylethyl)-spiro[cyclohexane-1,1'-(3'H)-isobenzofuran]-4-carboxamide,
trans-5'-methoxy-3'-oxo-N-methyl-N-(2-azocan-1-ylethyl)-spiro[cyclohexane-1,1'-(3'H)-isobenzofuran]-4-carboxamide,
2-piperidin-1-ylethyl-3-oxo-1'H,3H-spiro[2-benzofuran-1,4'-piperidine]-1'-carboxylate,
trans-5'-{[(trifluoromethyl)sulfonyl]oxy}-3'-oxo-N-methyl-N-(2-piperidin-1-ylethyl)-spiro[cyclohexane-1,1'-(3'H)-isobenzofuran]-4-carboxamide,
trans-5'-{[(trifluoromethyl)sulfonyl]oxy}-3'-oxo-N-methyl-N-(2-pyrrolidin-1-ylethyl)-spiro[cyclohexane-1,1'-(3'H)-isobenzofuran]-4-carboxamide,
trans-5'-(pyridin-3-yl)-3'-oxo-N-methyl-N-(2-piperidin-1-ylethyl)-spiro[cyclohexane-1,1'-(3'H)-isobenzofuran]-4-carboxamide,
trans-5'-(pyridin-4-yl)-3'-oxo-N-methyl-N-(2-piperidin-1-ylethyl)-spiro[cyclohexane-1,1'-(3'H)-isobenzofuran]-4-carboxamide,
trans-5'-(pyrimidin-5-yl)-3'-oxo-N-methyl-N-(2-piperidin-1-ylethyl)-spiro[cyclohexane-1,1'-(3'H)-isobenzofuran]-4-carboxamide,
trans-5'-(2-methoxypyrimidin-5-yl)-3'-oxo-N-methyl-N-(2-pyrrolidin-1-ylethyl)-spiro[cyclohexane-1,1'-(3'H)-isobenzofuran]-4-carboxamide,
trans-5'-(pyrazin-2-yl)-3'-oxo-N-methyl-N-(2-piperidin-1-ylethyl)-spiro[cyclohexane-1,1'-(3'H)-isobenzofuran]-4-carboxamide,
trans-5'-(pyridin-2-yl)-3'-oxo-N-methyl-N-(2-piperidin-1-ylethyl)-spiro[cyclohexane-1,1'-(3'H)-isobenzofuran]-4-carboxamide,
trans-5'-(pyrazin-2-yl)-3'-oxo-N-methyl-N-(2-pyrrolidin-1-ylethyl)-spiro[cyclohexane-1,1'-(3'H)-isobenzofuran]-4-carboxamide,
trans-5'-pyridin-2-yl-3'-oxo-N-methyl-N-(2-pyrrolidin-1-ylethyl)-spiro[cyclohexane-1,1'-(3'H)-isobenzofuran]-4-carboxamide,
trans-5'-cyclopropyl-3'-oxo-N-methyl-N-(2-pyrrolidin-1-ylethyl)-spiro[cyclohexane-1,1'-(3'H)-isobenzofuran]-4-carboxamide,
trans-5'-vinyl-3'-oxo-N-methyl-N-(2-pyrrolidin-1-ylethyl)-spiro[cyclohexane-1,1'-(3'H)-isobenzofuran]-4-carboxamide,
trans-5'-ethyl-3'-oxo-N-methyl-N-(2-pyrrolidin-1-ylethyl)-spiro[cyclohexane-1,1'-(3'H)-isobenzofuran]-4-carboxamide,
trans-5'-ethoxy-3'-oxo-N-methyl-N-(2-pyrrolidin-1-ylethyl)-spiro[cyclohexane-1,1'-(3'H)-isobenzofuran]-4-carboxamide,
trans-5'-isopropoxy-3'-oxo-N-methyl-N-(2-pyrrolidin-1-ylethyl)-spiro[cyclohexane-1,1'-(3'H)-isobenzofuran]-4-carboxamide,
trans-5'-[2-fluoro-1-(fluoromethyl)ethoxy]-3'-oxo-N-methyl-N-(2-piperidin-1-ylethyl)-spiro[cyclohexane-1,1'-(3'H)-isobenzofuran]-4-carboxamide,
trans-5'-[2-fluoro-1-(fluoromethyl)ethoxy]-3'-oxo-N-methyl-N-(2-pyrrolidin-1-ylethyl)-spiro[cyclohexane-1,1'-(3'H)-isobenzofuran]-4-carboxamide,
trans-5'-(pyridin-2-yloxy)-3'-oxo-N-methyl-N-(2-piperidin-1-ylethyl)-spiro[cyclohexane-1,1'-(3'H)-isobenzofuran]-4-carboxamide,
trans-5'-(pyrimidin-2-yloxy)-3'-oxo-N-methyl-N-(2-piperidin-1-ylethyl)-spiro[cyclohexane-1,1'-(3'H)-isobenzofuran]-4-carboxamide,
trans-5'-(pyrazin-2-yloxy)-3'-oxo-N-methyl-N-(2-piperidin-1-ylethyl)-spiro[cyclohexane-1,1'-(3'H)-isobenzofuran]-4-carboxamide,
trans-5'-(pyrimidin-2-yloxy)-3'-oxo-N-methyl-N-(2-pyrrolidin-1-ylethyl)-spiro[cyclohexane-1,1'-(3'H)-isobenzofuran]-4-carboxamide,
trans-5'-[(4-methoxypyrimidin-2-yl)oxy]-3'-oxo-N-methyl-N-(2-pyrrolidin-1-ylethyl)-spiro[cyclohexane-1,1'-(3'H)-isobenzofuran]-4-carboxamide,
trans-5'-(pyrazin-2-yloxy)-3'-oxo-N-methyl-N-(2-pyrrolidin-1-ylethyl)-spiro[cyclohexane-1,1'-(3'H)-isobenzofuran]-4-carboxamide,
trans-5'-[(2-cyanopyrimidin-5-yl)oxy]-3'-oxo-N-methyl-N-(2-pyrrolidin-1-ylethyl)-spiro[cyclohexane-1,1'-(3'H)-isobenzofuran]-4-carboxamide,
trans-5'-[(5-fluoropyrimidin-2-yl)oxy]-3'-oxo-N-methyl-N-(2-pyrrolidin-1-ylethyl)-spiro[cyclohexane-1,1'-(3'H)-isobenzofuran]-4-carboxamide, trans-5'-(piperidin-4-yloxy)-3'-oxo-N-methyl-N-(2-piperidin-1-ylethyl)-spiro[cyclohexane-1,1'-(3'H)-isobenzofuran]-4-carboxamide, trans-5'-[(1-acetylpiperidin-4-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-acetylpyrrolidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-acetylpiperidin-4-yl)oxy]-3'-oxo-N-methyl-N-(2-pyrrolidin-1-ylethyl)-spiro[cyclohexane-1,1'-(3'H)-isobenzofuran]-4-carboxamide, trans-5'-[(1-acetylpyrrolidin-3-yl)oxy]-3'-oxo-N-methyl-N-(2-pyrrolidin-1-ylethyl)-spiro[cyclohexane-1,1'-(3'H)-isobenzofuran]-4-carboxamide, trans-5'-4-{[1-(diphenylmethyl)azetidin-3-yl]oxy]-3'-oxo-N-methyl-N-(2-piperidin-1-ylethyl)-spiro[cyclohexane-1,1'-(3'H)-isobenzofuran]-4-carboxamide, trans-5'-(azetidin-3-yloxy)-3'-oxo-N-methyl-N-(2-piperidin-1-ylethyl)-spiro[cyclohexane-1,1'-(3'H)-isobenzofuran]-4-carboxamide, trans-5'-[(1-acetylazetidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-methylsulfonyl)piperidin-4-yl]oxy]-3-oxo-N-methyl-N-(2-piperidin-1-ylethyl)-spiro[cyclohexane-1,1'-(3'H)-isobenzofuran]-4-carboxamide, trans-5'-[(1-methylsulfonyl)-pyrrolidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-methylsulfonyl)-pyrrolidin-3-yl)oxy]-3'-oxo-N-methyl-N-(2-pyrrolidin-1-ylethyl)-spiro[cyclohexane-1,1'-(3'H)-isobenzofuran]-4-carboxamide, trans-5'-[(1-methylsulfonyl)-azetidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-formylazetidin-3-yl)oxy]-3'-oxo-N-methyl-N-(2-piperidin-1-ylethyl)-spiro[cyclohexane-1,1'-(3'H)-isobenzofuran]-4-carboxamide, trans-5'-[(1-methoxycarbonylazetidin-3-yl)oxy]-3'-oxo-N-methyl-N-(2-piperidin-1-ylethyl)-spiro[cyclohexane-1,1'-(3'H)-isobenzofuran]-4-carboxamide and trans-5'-[(1-propionylazetidin-3-yl)oxy]-3'-oxo-N-methyl-N-(2-piperidin-1-ylethyl)-spiro[cyclohexane-1,1'-(3'H)-isobenzofuran]-4-carboxamide, or a pharmaceutically acceptable thereof.

5. A compound which is selected from the group consisting of:

trans-5-(2-fluoroethoxy)-3-oxo-3H-spiro[2-benzofuran-1,1'-cyclohexane]-4'-carboxylic acid, trans-5-methoxy-3-oxo-3H-spiro[2-benzofuran-1,1'-cyclohexane]-4'-carboxylic acid, trans-6-methoxy-3-oxo-3H-spiro[2-benzofuran-1,1'-cyclohexane]-4'-carboxylic acid, trans-7-methoxy-3-oxo-3H-spiro[2-benzofuran-1,1'-cyclohexane]-4'-carboxylic acid, trans-5-fluoro-3-oxo-3H-spiro[2-benzofuran-1,1'-cyclohexane]-4'-carboxylic acid, trans-5-hydroxy-3-oxo-3H-spiro[2-benzofuran-1,1'-cyclohexane]-4'-carboxylic acid, trans-2'-methyl-3'-oxo-2',3'-dihydrospiro-[cyclohexane-1,1'-isoindole]-4'-carboxylic acid, cis-2'-methyl-3'-oxo-2',3'-dihydrospiro-[cyclohexane-1,1'-isoindole]-4'-carboxylic acid, trans-5-methoxy-3-oxo-3H-spiro[2-benzofuran-1,1'-cyclohexane]-4'-methyl-4-carboxylic acid, or a pharmaceutically-acceptable salt thereof.

6. A compound which is:

trans-5'-methoxy-3'-oxo-N-methyl-N-(2-piperidin-1-ylethyl)-spiro[cyclohexane-1,1'-(3'H)-isobenzofuran]-4-carboxamide, or a pharmaceutically-acceptable salt thereof.

7. A pharmaceutical composition which comprises an inert carrier and the compound of claim 1 or a pharmaceutically acceptable salt thereof.

8. A pharmaceutical composition which comprises an inert carrier and the compound of claim 4 or a pharmaceutically acceptable salt thereof.

9. A pharmaceutical composition which comprises an inert carrier and the compound of claim 5 or a pharmaceutically acceptable salt thereof.

10. A pharmaceutical composition which comprises an inert carrier and the compound of claim 6 or a pharmaceutically acceptable salt thereof.

* * * * *